United States Patent
Meyer et al.

(10) Patent No.: US 12,227,485 B2
(45) Date of Patent: Feb. 18, 2025

(54) **COMPOUNDS USEFUL FOR THE TREATMENT OF INFECTION WITH *MANNHEIMIA HAEMOLYTICA* OR *HISTOPHILUS SOMNI***

(71) Applicant: Intervet Inc., Madison, NJ (US)

(72) Inventors: Thorsten Meyer, Wiesbaden (DE); Michael Berger, Wiesbaden (DE); Ralf Warrass, Alzey (DE); Joachim Ullrich, Stadecken-Elsheim (DE)

(73) Assignee: Intervet Inc., Rahway, NJ (US)

( * ) Notice: Subject to any disclaimer, the term of this patent is extended or adjusted under 35 U.S.C. 154(b) by 1083 days.

(21) Appl. No.: 17/253,346

(22) PCT Filed: Jun. 24, 2019

(86) PCT No.: PCT/EP2019/066667
§ 371 (c)(1),
(2) Date: Dec. 17, 2020

(87) PCT Pub. No.: WO2020/002234
PCT Pub. Date: Jan. 2, 2020

(65) Prior Publication Data
US 2021/0292284 A1    Sep. 23, 2021

(30) Foreign Application Priority Data
Jun. 25, 2018  (EP) ..................... 18179616

(51) Int. Cl.
*C07D 239/94* (2006.01)
*A61P 11/00* (2006.01)
*A61P 31/04* (2006.01)
*C07D 217/22* (2006.01)
*C07D 275/04* (2006.01)

(52) U.S. Cl.
CPC ............ *C07D 239/94* (2013.01); *A61P 11/00* (2018.01); *A61P 31/04* (2018.01); *C07D 217/22* (2013.01); *C07D 275/04* (2013.01)

(58) Field of Classification Search
CPC ........ A61P 11/00; A61P 31/04; C07D 217/22; C07D 239/94; C07D 275/04
See application file for complete search history.

(56) References Cited

U.S. PATENT DOCUMENTS

| 2003/0181398 | A1 | 9/2003 | Brown | |
| 2012/0077764 | A1* | 3/2012 | Freehauf | A61K 31/16 |
| | | | | 514/630 |

FOREIGN PATENT DOCUMENTS

CN          105777464 A       7/2016

OTHER PUBLICATIONS

Sun et al., Classification of scaffold-hopping approaches, Drug Discovery Today, Nov. 2011 (Year: 2011).*
Extended European Search report for U.S. Appl. No. 18/179,616..0 mailed on Aug. 17, 2018.
Jing Zhang et al, Structure-based discovery of LpxC inhibitors, Bioorganic & Medicinal Chemistry Letters, 2017, pp. 1670-1680, vol. 27, Elsevier.

* cited by examiner

*Primary Examiner* — Sarah Pihonak
*Assistant Examiner* — Padmaja S Rao
(74) *Attorney, Agent, or Firm* — David J. Kerwick; Jenny Cromsigt

(57) ABSTRACT

The present invention discloses compounds that are useful in the treatment of respiratory diseases of animals, especially Bovine or Swine Respiratory disease (BRD and SRD).

5 Claims, No Drawings

COMPOUNDS USEFUL FOR THE TREATMENT OF INFECTION WITH *MANNHEIMIA HAEMOLYTICA* OR *HISTOPHILUS SOMNI*

CROSS-REFERENCE TO RELATED APPLICATIONS

This application is a national stage entry under 35 U.S.C. § 371 of PCT/EP2019/066667, filed on Jun. 24, 2019, which claims priority to EP application Ser. No. 18/179,616.0, filed on Jun. 25, 2018; the content of EP18179616.0, is hereby incorporated by reference in its entirety.

The present invention relates to the field of compounds for the treatment of respiratory diseases of animals, especially of Bovine or Swine Respiratory disease (BRD or SRD).

BACKGROUND

Bovine respiratory disease (BRD) is the most common and costly disease affecting beef cattle in the world. It is a complex, bacterial infection that causes pneumonia in calves and can possibly be fatal. The infection is usually a sum of three codependent factors: Stress, an underlying viral infection, and a new bacterial infection. The diagnosis of the disease is complex since there are multiple possible causes. The disease manifests itself most often in calves within four weeks of weaning, when calves are sorted and often sold to different farms. This gives it a common nickname, "Shipping Fever."

BRD is of major economic importance to the North American and the global cattle industries. The United States feedlot industry estimates an annual loss as high as 1 billion dollars due to loss of production, increased labor expenses, drug costs, and death because of bovine respiratory disease (BRD). *Mannheimia haemolytica, Pasteurella multocida, Histophilus somni,* and *Mycoplasma bovis* are the bacterial agents that have been most consistently implicated in BRD Viral agents include Bovine Viral Diarrhea (BVD), Infectious Bovine Rhinotracheitis (IBR), Bovine Respiratory Synctial Virus (BRSV), and Parainfluenza Type-3 Virus (PI-3).

*Pasteurella* is a genus of Gram-negative, facultatively anaerobic bacteria *Pasteurella multocida* is the cause of a range of diseases in mammals and birds, including fowl cholera in poultry, atrophic rhinitis in pigs, and bovine hemorrhagic septicemia in cattle and buffalo.

*Histophilus somni* is also known as *Haemophilus agni, Histophilus ovis Haemophilus somnus,* and *Haemophilus somnifer.*

*Histophilus somni* is a bacterium that lives in the nasal passages of cattle. Generally speaking, *H. somni* infects vascular tissue (blood vessels) and endothelium of organs, causing inflammation, thrombosis (formation of a vascular obstruction) that interrupts the blood supply, and causes local cellular death.

*H. somni* typically colonize in the respiratory tract, reproductive tract, and circulatory system of many herd animals such as cattle, sheep, and American bison. If *H. somni* infects the lungs, pneumonia can result in rapid death. If *H. somni* gains access to the bloodstream, it spreads throughout the body, a condition known as septicemia.

*Mannheimia haemolytica* is a species of the *Mannheimia* genus. *Mannheimia haemolytica* is a gram-negative bacterium normally found in the upper respiratory tract of healthy cattle, sheep and wild sheep.

*Mannheimia haemolytica* was formerly known as: *Pasteurella haemolytica. M. haemolytica* descends into the lungs when cattle experience stress such as shipping, weaning, overcrowding, or viral infections and causes fibrinous and necrotizing bronchopneumonia, a chief component of the bovine respiratory disease (BRD). *M. haemolytica* is the bacterium most commonly isolated from the lungs of cattle affected with BRD in the United States.

Vaccinations exist for several biological BRD precursors, but the multitude of possible precursors complicates the process of choosing a vaccine regime. Bacteria may be treated with common antibiotics.

Fear of antibiotic resistance caution the use of broad spectrum antibiotics and instead prefer compounds that selectively kill bacteria.

There exists a need for such compounds that treat bovine respiratory disease (BRD) associated with *Mannheimia haemolytica, Pasteurella multocida* and *Histophilus somni.*

Preferably these compounds are active against the bacterial causes of BRD. Preferably the compounds are active against *Mannheimia haemolytica, Pasteurella multocida* and *Histophilus somni.* Preferably the compounds are also active against resistant (e.g. macrolide) strains of these bacteria.

Respiratory disease in swine is arguably the most important health concern for swine producers today. As with respiratory disease in humans and other species, respiratory disease in swine is often the result of a combination of primary and opportunistic infectious agents. In addition, adverse environmental and management conditions play an important role in the multifactorial nature of respiratory disease in pigs.

The term swine respiratory disease (SRD) was used to describe pneumonia of multiple etiology causing clinical disease and failure to gain weight later in the finishing process (15 to 20 weeks of age). *Actinobacillus pleuropneumoniae* is a gram-negative bacterium which is the most common cause of pleuropneumonia in pigs. Outbreaks of *A. pleuropneumoniae* are usually precipitated by stress, environmental changes, or viral or mycoplasmal infection. The disease may present clinically as a peracute form with sudden death; an acute form with clinical signs characterized by fever, lethargy, dyspnea, cyanosis, recumbency, and froth from the nose; or a subacute/chronic form which develops after disappearance of acute signs with intermittent cough, slow growth, and exercise intolerance. *P. multocida* is a gram-negative bacterium which is a cause of atrophic rhinitis and pneumonia in pigs. *Bordetella bronchiseptica* is a gram-negative bacterium that causes rhinitis and mild to moderate turbinate atrophy and predisposes to infection with toxigenic strains of *P. multocida* which causes the progressive form of atrophic rhinitis.

*Mycoplasma hyopneumoniae* is the primary pathogen associated with enzootic pneumonia, which occurs when *M. hyopneumoniae* is combined with opportunistic bacteria such as *P. multocida.*

*Haemophilus parasuis* is a gram-negative bacterium which causes polyserositis (Glässer's disease) and pneumonia in swine. Clinical signs include fever, anorexia, swollen joints with lameness, dyspnea, and central nervous system signs. Because of the incomplete efficacy of vaccines, antibacterials are needed to treat *H. parasuis* infections.

Consequently, there is a need for compounds for the treatment and control of swine respiratory disease (SRD) especially when associated with *Pasteurella multocida, Actinobacillus pleuropneumoniae, Bordetella bronchiseptica* or *Haemophilus parasuis.* Preferably these compounds are active against the bacterial causes of SRD. Preferably the compounds are active against *Pasteurella multocida* and *Actinobacillus pleuropneumoniae*. Preferably the compounds are also active against *Bordetella bronchiseptica*. In one embodiment they are active against *Mycoplasma* spp. It is therefore desirable, that such antibacterial compounds have an effect on such bacterial pathogens involved in BRD and/or SRD but are not active against pathogens (especially multiresistant) that are important in human health, such as *Straphylococcus* spp. and *Streptrococcus* spp., *Acinetobacter* species, especially *Acinetobacter baumanii*.

SUMMARY OF THE INVENTION

Surprisingly it was found that at least one of the objects can be met by providing a compound according to the formula (I):

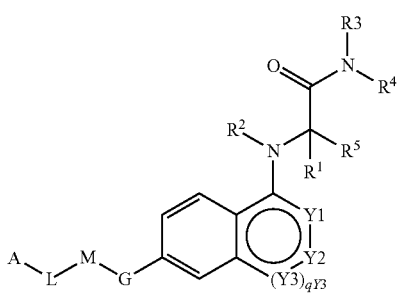

or a stereoisomer, pharmaceutically acceptable salt, ester, solvate, or prodrug thereof, wherein A is selected from the group consisting of
$NR^{A1}R^{A2}$ and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl and $C_1$-$C_6$-alkyl substituted with heterocyclyl,
or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$—, carbonyl, —C(=O)—$OR^{A5}$—, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$—, —$SO_2R^{A5}$—, $SO_2NR^{A3}R^{A4}$, —C(=O)$NR^{A3}R_{A4}$—, $C_{1-6}$-alkyl substituted with hydroxy;
wherein
$R^{A3}$, $R^{A4}$, $R^{A5}$ are independently chosen from H or $C_{1-6}$-alkyl;

L is absent or selected from the group consisting of
$C_{1-6}$-alkyl, $C_{2-6}$-alkenyl, $C_{2-6}$-alkynyl, $C_{3-10}$-cycloalkyl, aryl, heterocyclyl, heteroaryl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—$(CR^{L1}R^{L2})$—$NR^{L3}C(=O)$—, —C(=O)$NR^{L3}$—, —$NR^{L3}C(=O)$—, —$SO_2NR^{L3}$—, and $NR^{L3}$—C(=O)—$NR^{L3}$—
wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$-alkenyl, $C_{2-4}$-alkynyl, —C($R^{M1}$)=C($R^{M1}$)—C≡C—, and —C($R^{M1}$)=C($R^{M1}$)—,
wherein each cycloalkyl, aryl, heterocyclyl, or heteroaryl is optionally substituted with a substituent selected from the group consisting of
$C_{1-6}$-alkyl, $C_{3-8}$-cycloalky, $C_{1-6}$-alkyloxy, $NR^{M2}R^{M3}$, carbonyl, —C(=O)—$OR^{M2}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, —C(=O)$NR^{M2}R^{M3}$—, and hydroxy-$C_{1-6}$-alkyl;
wherein $R^{M1}$ is selected from the group consisting of H, $C_{1-6}$-alkyl, halo, hydroxyl, and amino;
wherein $R^{M2}$, $R^{M3}$ are independently selected from the group consisting of H, and $C_{1-6}$-alkyl;
wherein $R^{M4}$ is selected from the group consisting of H, $C_{1-6}$-alkyl, and amino;
G is selected from the group consisting of
—$(C(R^{G2}R^{G3})_{0-4}$—O—$(C(R^{G2}R^{G3})_{0-4}$—, —$(C(R^{G2}R^{G3})_{0-4}$—S—$(C(R^{G2}R^{G3})_{0-4}$—, —$(C(R^{G2}R^{G3})_{0-4}$—$NR^{G1}$—$(C(R^{G2}R^{G3})_{0-4}$—, —C(=O)—, —$NR^{G1}$C(=O)—, —C(=O)$NR^{G1}$—, —$(C(R^{G2}R^{G3})_{0-4}$—$NR^{G1}$—C($R^{G2}R^{G3}$)—C(=O)$NR^{G1}$—, —$CR^{G2}$=$CR^{G2}$—, —$CR^{G2}$=$CR^{G2}$—$CR^{G2}$=$CR^{G2}$—, —$CR^{G2}$=$CR^{G2}$—C≡C—, —C≡C—$CR^{G2}$=$CR^{G2}$, —C(=O)—C≡C—, —C≡C—C(=O)—$SO_2$—, —S(=O)—, —S(=O)C($R^{G2}R^{G3}$)—, —C($R^{G2}R^{G3}$)S(=O)—, —C($R^{G2}R^{G3}$)—$SO_2$—, and —$SO_2$C($R^{G2}R^{G3}$)—;
wherein
$R^{G1}$ is H or $C_{1-6}$-alkyl
each $R^{G2}$, $R^{G3}$ is independently selected from the group consisting of
H, halogen atom, or $C_{1-6}$-alkyl;
$R^1$ is selected from the group consisting of
H, $C_{2-6}$-alkenyl, $C_{2-6}$-alkynyl, $C_{3-10}$-cycloalkyl, C(=O)$R^9$, C(=N—$OR^8$)$R^8$, aryl, heterocyclyl, heteroaryl, $C_1$-$C_6$-alkyl substituted with aryl, $C_1$-$C_6$-alkyl substituted with heteroaryl, and $C_1$-$C_6$-alkyl substituted with heterocyclyl;
wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalky, $C_{1-6}$-alkyloxy, $NR^6R^7$, carbonyl, nitro, C(=O)$OR^8$, halogen, halo-$C_{1-6}$-alkyl, $C_{1-6}$- alkyloxy-$C_1$-$C_6$-alkyl, cyano, hydroxy, —$SO_2R^8$, $SO_2NR^6R^7$, —C(=O)$NR^6R^7$;

$R^2$, $R^3$ are independently selected from the group consisting of

H, substituted $C_{1-6}$-alkyl, and un-substituted $C_{1-6}$-alkyl;
wherein the substituents on the substituted $C_{1-6}$-alkyl may be selected from the group consisting of halogen, hydroxyl, alkoxy, aryloxy, thiol, $C_{1-6}$-alkyl, carbonyl, —$SR^8$, —$SO_2R^8$, $SO_2NR^6R^7$, —C(=O)$NR^6R^7$, cyano, —$NR^6R^7$, —C(=O)—$OR^6$, aryl, heteroaryl, heterocycle, $C_{3-8}$-cycloalkyl;

$R^4$ is selected from the group consisting of

H, $C_{2-6}$-alkenyl, $C_{2-6}$-alkynyl, $C_{3-10}$-cycloalkyl, C(=O)$OR^8$, C(=O)$R^8$, aryl, heterocyclyl, heteroaryl, $C_1$-$C_6$-alkyl substituted with aryl, $C_1$-$C_6$-alkyl substituted with heteroaryl, and $C_1$-$C_6$-alkyl substituted with heterocyclyl;

wherein each alkyl, alkenyl, alkynyl, cycloalkyl, aryl, heterocyclyl, heteroaryl, is optionally substituted with a substituent selected from the group consisting of $C_{1-6}$-alkyl, $C_{3-8}$-cycloalky, $C_{1-6}$-alkyloxy, $NR^6R^7$, carbonyl, nitro, C(=O)$OR^8$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, and —C(=O)$NR^6R^7$;

$R^5$ is selected from the group consisting of H and $C_{1-6}$-alkyl;

$R^6$, $R^7$, $R^8$ are independently selected from the group consisting of H and $C_{1-6}$-alkyl;

wherein $R^9$ is selected from the group consisting of H, hydroxyl and $C_{1-6}$-alkyl, wherein Y1, Y2, Y3 are each independently $CR^{10}$, N, O or S, and at least one of Y1, Y2, Y3 is a heteroatom selected from the group consisting of N, O, S, wherein $R^{10}$ is selected from the group consisting of H, $C_{2-6}$-alkenyl, $C_{2-6}$-alkynyl, $C_{3-10}$-cycloalkyl, C(=O)$OR^8$, C(=O)$R^8$, aryl, heterocyclyl, heteroaryl, $C_1$-$C_6$-alkyl substituted with aryl, $C_1$-$C_6$-alkyl substituted with heteroaryl, and $C_1$-$C_6$-alkyl substituted with heterocyclyl;

wherein each alkyl, alkenyl, alkynyl, cycloalkyl, aryl, heterocyclyl, heteroaryl, is optionally substituted with a substituent selected from the group consisting of $C_{1-6}$-alkyl, $C_{3-8}$-cycloalky, $C_{1-6}$-alkyloxy, $NR^6R^7$, carbonyl, nitro, C(=O)$OR^8$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, and —C(=O)$NR^6R^7$; and qY3 is 0 or 1.

Suitably, in an embodiment of the invention and/or embodiments thereof, A is defined as described herein.

In yet another embodiment of the invention and/or embodiments thereof, A is selected from the group consisting of $NR^{A1}R^{A2}$ and $NO_2$,
wherein $R^{A1}$, $R^{A2}$ are independently selected from the group consisting of H, $C_{2-6}$-alkenyl, $C_{2-6}$-alkynyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl and $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S and O.

In yet another embodiment of the invention and/or embodiments thereof, A is selected from the group consisting of $NR^{A1}R^{A2}$ and $NO_2$,
wherein $R^{A1}$, $R^{A2}$ are independently selected from the group consisting of H, $C_{2-6}$-alkenyl, $C_{2-6}$-alkynyl, $C_{3-10}$-cycloalkyl, $C_{1-6}$-alkyloxy-$C_1$-$C_6$-alkyl, $C_1$-$C_6$-alkyl substituted with aryl, and $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S and O.

In yet another embodiment of the invention and/or embodiments thereof L is defined as described herein.

In yet another embodiment of the invention and/or embodiments thereof L is selected from the group consisting of $C_{1-6}$-alkyl, $C_{2-6}$-alkenyl, $C_{2-6}$-alkynyl, $C_{3-10}$-cycloalkyl,
wherein $R^{L3}$, is selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.

Suitably L is selected from the group consisting of $C_{1-6}$-alkyl, or $C_{2-6}$-alkenyl. Preferably L is $CH_2$—, —$CH_2CH_2$—, —$CH_2CH_2CH_2$—, or $CH_2CH_2CH_2CH_2$—, more preferably L is $CH_2$—, —$CH_2CH_2$—, or —$CH_2CH_2CH_2$—, more preferably L is $CH_2$—, or —$CH_2CH_2$—, in particular —$CH_2$—.

In another embodiment of the invention and/or embodiments thereof, M is defined as described herein.

Suitably M is selected from the group consisting of $C_{3-10}$-cycloalkyl, aryl, heterocyclyl, heteroaryl, $C_{2-4}$ alkenyl, $C_{2-4}$alkynyl, —C($R^{M1}$)=C($R^{M1}$)—C≡C—, —C($R^{M1}$)=C($R^{M1}$).

wherein $R^{M1}$ is selected from the group consisting of H, $C_{1-6}$-alkyl, halo, hydroxyl, and amino More suitably M is selected from the group consisting of aryl, heterocyclyl, heteroaryl, —C($R^{M1}$)=C($R^{M1}$)—C≡C—, —C($R^{M1}$)=C($R^{M1}$)—. More suitably M is selected from the group consisting of aryl, heteroaryl, —C($R^{M1}$)=C($R^{M1}$)—C≡C—, —C($R^{M1}$)=C($R^{M1}$)—. More preferably M is selected form the group consisting of aryl and heretoaryl. Particularly preferred M is phenyl.

In another embodiment of the invention and/or embodiments thereof, G is defined as described herein.

In suitable embodiments, G is selected from the group consisting of —(C($R^{G2}R^{G3}$))$_{0-4}$—O—(C($R^{G2}R^{G3}$))$_{0-4}$—, —(C($R^{G2}R^{G3}$))$_{0-4}$—S—(C($R^{G2}R^{G3}$))$_{0-4}$—, —(C($R^{G2}R^{G3}$))$_{0-4}$—$NR^{G1}$—(C($R^{G2}R^{G3}$))$_{0-4}$—, —C(=O)—, —$NR^{G1}$C(=O)—, —C(=O)$NR^{G1}$—, —(C($R^{G2}R^{G3}$))$_{0-4}$—$NR^{G1}$—C($R^{G2}R^{G3}$)—C(=O)$NR^{G1}$—, —$CR^{G2}$=$CR^{G2}$—, —C≡C—, —C≡C—C≡C—, —C≡C—C(=O)—, $SO_2$—, —S(=O)—, —S(=O)C($R^{G2}R^{G3}$)—, —C($R^{G2}R^{G3}$)S(=O)—, —C($R^{G2}R^{G3}$)—$SO_2$—, —$SO_2$C($R^{G2}R^{G3}$)—;
wherein $R^{G1}$ is H or $C_{1-6}$-alkyl each $R^{G2}$, $R^{G3}$ is independently selected from the group consisting of H, halogen atom, or $C_{1-6}$-alkyl.

In suitable embodiments, G is selected from the group consisting of —C≡C—, —C≡C—C≡C—, —CR$^{G2}$=CR$^{G2}$—C≡C—, —C≡C—CR$^{G2}$=CR$^{G2}$,
wherein R$^{G2}$ is selected from the group consisting of H, halogen atom, or C$_{1-6}$-alkyl.

In another suitable embodiments, G is selected from the group consisting of CR$^{G2}$=CR$^{G2}$—, —C≡C—, —C≡C—C≡C—, —C≡C—C(=O)—.
wherein
R$^{G2}$ is selected from the group consisting of
H, halogen atom, or C$_{1-6}$-alkyl.

In another embodiment G is selected from the group consisting of —CH=CH— and —C≡C—, in particular —C≡C—.

In some embodiments of the invention and/or embodiments thereof the compound is a compound according to formula (II)

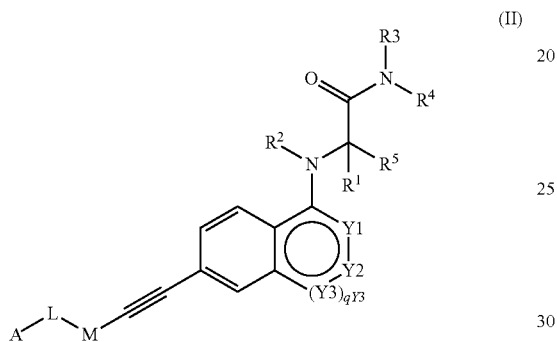

(II)

or a stereoisomer, pharmaceutically acceptable salt, ester, solvate, or prodrug thereof, wherein A, L, M, R$^1$, R$^2$, R$^3$, R$^4$, R$^5$, Y1, Y2, Y3 and qY3 are defined as in any of the embodiments described herein.

In another embodiment of the invention and/or embodiments thereof, Y1, Y2 and Y3 and qY3 are defined as described herein.

In suitable embodiments Y1 is CR$^{10}$, N, O or S, wherein R$^{10}$ is selected from the group consisting of
H, C$_{1-6}$-alkyl, C$_{2-6}$-alkenyl, C$_{2-6}$-alkynyl, C$_{3-10}$-cycloalkyl, —OR$^8$, C(=O)OR$^8$, C(=O)R$^8$, aryl, heterocyclyl, heteroaryl, C$_1$-C$_6$-alkyl substituted with aryl, C$_1$-C$_6$-alkyl substituted with heteroaryl, and C$_1$-C$_6$-alkyl substituted with heterocyclyl;
wherein each alkyl, alkenyl, alkynyl, cycloalkyl, aryl, heterocyclyl, heteroaryl, is optionally substituted with a substituent selected from the group consisting of
C$_{1-6}$-alkyl, C$_{3-8}$-cycloalky, C$_{1-6}$-alkyloxy, NR$^6$R$^7$, carbonyl, nitro, C(=O)OR$^8$, halogen, halo-C$_{1-6}$-alkyl, C$_{1-6}$-alkyloxy-C$_1$-C$_6$-alkyl, cyano, hydroxy, —SR$^8$, —SO$_2$R$^8$, SO$_2$NR$^6$R$^7$, and —C(=O)NR$^6$R$^7$.

In more suitable embodiments Y1 is CR$^{10}$ or N, wherein R$^{10}$ is selected from the group consisting of H, C$_{1-6}$-alkyl, C$_{2-6}$-alkenyl, C$_{3-10}$-cycloalkyl, —OR$^8$, C(=O)OR$^8$, C(=O)R$^8$, aryl, heteroaryl;
wherein each alkyl, alkenyl, cycloalkyl, aryl, heteroaryl, is optionally substituted with a substituent selected from the group consisting of
C$_{1-6}$-alkyl, C$_{3-8}$-cycloalky, C$_{1-6}$-alkyloxy, NR$^6$R$^7$, carbonyl, nitro, C(=O)OR$^8$, halogen, halo-C$_{1-6}$-alkyl, C$_{1-6}$-alkyloxy-C$_1$-C$_6$-alkyl, cyano, hydroxy, —SR$^8$, —SO$_2$R$^8$, SO$_2$NR$^6$R$^7$, and —C(=O)NR$^6$R$^7$ More preferably Y1 is CR$^{10}$ or N, wherein R$^{10}$ is selected from the group consisting of H, C$_{1-6}$-alkyl, OR$^8$,
wherein each alkyl is optionally substituted with a substituent selected from the group consisting of
C$_{1-6}$-alkyl, NR$^6$R$^7$, halogen, cyano, hydroxy, and —C(=O)NR$^6$R$^7$.

In a particularly preferred embodiment Y1 is N or CH, especially N.

In some embodiments of the invention and/or embodiments thereof the compound is a compound according to formula (III)

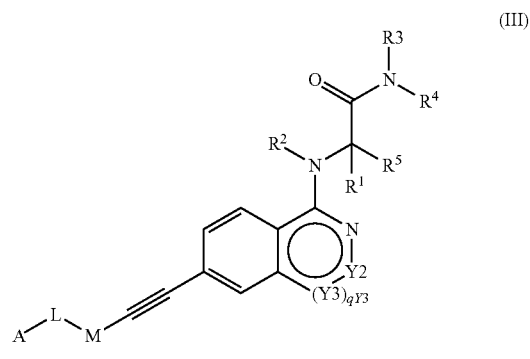

(III)

or a stereoisomer, pharmaceutically acceptable salt, ester, solvate, or prodrug thereof, wherein A, L, M, R$^1$, R$^2$, R$^3$, R$^4$, R$^5$, Y2, Y3 and qY3 are defined as in any of the embodiments described herein.

In some embodiments Y2 is CR$^{10}$, N, O, or S, wherein R$^{10}$ is defined as in the embodiments described herein.

In some embodiment when qY3 is 0, Y2 is CR$^{10}$, N, O, or S, wherein R$^{10}$ is selected from the group consisting of
H, C$_{1-6}$-alkyl, OR$^8$,
wherein each alkyl is optionally substituted with a substituent selected from the group consisting of
C$_{1-6}$-alkyl, NR$^6$R$^7$, halogen, cyano, hydroxy, and —C(=O)NR$^6$R$^7$ In some embodiment, when qY3 is 0, Y2 is CH, N or S, preferably CH or S.

In some embodiment when qY3 is 1, Y2 is CR$^{10}$, N, O, or S, wherein R$^{10}$ is selected from the group consisting of
H, C$_{1-6}$-alkyl, OR$^8$,
wherein each alkyl is optionally substituted with a substituent selected from the group consisting of
C$_{1-6}$-alkyl, NR$^6$R$^7$, halogen, cyano, hydroxy, and —C(=O)NR$^6$R$^7$.

In some embodiment, when qY3 is 1, Y2 is N or CR$^{10}$, wherein R$^{10}$ is selected from the group consisting of
H, C$_{1-6}$-alkyl, OR$^8$,
wherein each alkyl is optionally substituted with a substituent selected from the group consisting of
C$_{1-6}$-alkyl, NR$^6$R$^7$, halogen, cyano, hydroxy, and —C(=O)NR$^6$R$^7$, preferably CH or N.

In a particularly preferred embodiment, when qY3 is 1, Y2 is CR$^{10}$, especially CH.

In an alternative, particularly preferred embodiment, when qY3 is 1, Y2 is N.

In some embodiment Y3 is CR$^{10}$, N, O, or S, wherein R$^{10}$ is selected from the group consisting of
H, C$_{1-6}$-alkyl, OR$^8$,
wherein each alkyl is optionally substituted with a substituent selected from the group consisting of
C$_{1-6}$-alkyl, NR$^6$R$^7$, halogen, cyano, hydroxy, and —C(=O)NR$^6$R$^7$ In some embodiment, Y3 is N or $CR^{10}$, wherein $R^{10}$ is selected from the group consisting of H, $C_{1-6}$-alkyl, $OR^8$, wherein each alkyl is optionally substituted with a substituent selected from the group consisting of $C_{1-6}$-alkyl, $NR^6R^7$, halogen, cyano, hydroxy, and —C(=O)$NR^6R^7$, preferably CH or N.

In a particularly preferred embodiment, Y3 is $CR^{10}$, especially CH.

In an alternative, particularly preferred embodiment, Y3 is N.

In a particularly preferred embodiment, when qY3 is 1, Y2 is CH and Y3 is N.

In embodiments of the invention and/or embodiments thereof $R^1$ is defined as described herein.

Suitably $R^1$ is selected from the group consisting of H, $C(R^{11}R^{12}R^{13})$ $C(=O)R^{11}$, —C(=$NR^{14}$)$R^{11}$;

$R^{11}$ is selected from the group consisting of H, and $C_{1-6}$-alkyl;

$R^{12}$ is selected from the group consisting of
H, $C_{1-6}$-alkyl, and $C_{1-6}$-alkyl substituted with a substituent from the group consisting of —$SR^8$, —$OR^8$, —C(=O)$OR^8$, —$NR^6R^7$, —$SO_2NR^6R^7$, —$SO_2R^8$;

$R^{13}$ is selected from the group consisting of
H, $C_{1-6}$-alkyl, aryl, —$SR^8$, —$OR^8$, —$NR^6R^7$, —$SO_2R^8$, nitro, —C(=O)$NR^6R^7$, and $C_{1-6}$-alkyl substituted with a substituent selected from the group consisting of —$SR^8$, —C(=O)$NR^6R^7$, —$SO_2R^8$, —$SO_2NR^6R^7$, nitro, cyano, —$OR^8$, —C(=O)$OR^8$, —$NR^8C$(=$NR^{14}$)$NR^6R^7$;

or $R^{13}$ and $R^2$ together with the N atom which $R^2$ is attached to, form a saturated or unsaturated heterocycle having 3 to 6 ring atoms wherein 1 ring atom is N and 0, 1 or 2 further ring atoms are selected from N, S, and O the rest of the ring atoms being C $R^{14}$ is selected from the group consisting of H, $C_{1-6}$-alkyl.

In another suitable embodiment of the present invention and/or embodiments thereof, $R^{12}$ is selected from the group consisting of H, $C_{1-6}$-alkyl, and $C_{1-6}$-alkyl substituted with a substituent from the group consisting of —$SR^8$, —$OR^8$, —C(=O)$OR^8$, —$NR^6R^7$, —$SO_2NR^6R^7$, —$SO_2R^8$.

Suitably in certain embodiments of the present invention and/or embodiments thereof, the substituted $C_{1-6}$-alkyl in $R^{12}$ is substituted with a substituent selected from the group consisting of

—$SR^8$, —$OR^8$, —$NR^6R^7$, —$SO_2NR^6R^7$, —$SO_2R^8$.

In some embodiments of the present invention and/or embodiments thereof, $R^{13}$ is selected from the group consisting of H, $C_{1-6}$-alkyl, —$SR^8$, —$OR^8$, —$NR^6R^7$, —$SO_2R^8$, nitro, —C(=O)$NR^6R^7$, and $C_{1-6}$-alkyl substituted with a substituent selected from the group consisting of $SR^8$, —C(=O)$NR^6R^7$, —$SO_2R^8$, —$SO_2NR^6R^7$, nitro, cyano, —$OR^8$, —C(=O)$OR^8$, —$NR^8C$(=$NR^{14}$)$NR^6R^7$.

Suitably in certain embodiments of the present invention and/or embodiments thereof, the substituted $C_{1-6}$-alkyl in $R^{13}$ is substituted with a substituent selected from the group consisting of $SR^8$, —C(=O)$NR^6R^7$, —$SO_2R^8$, —$SO_2N^6R^7$, nitro, cyano, —$OR^8$, —C(=O)$OR^8$, —$NR^8C$(=$NR^{14}$)$NR^6R^7$.

In some embodiments of the present invention and/or embodiments thereof, the aryl in $R^{13}$ is phenyl or hydroxyphenyl.

Suitably in certain embodiments of the present invention and/or embodiments thereof, $R^{13}$ and $R^2$ together with the N atom which $R^2$ is attached to, form a heterocycle selected from the group consisting of aziridine, azirine, azetidine, dihydroazete, azete, diazetidine, pyrrolidine, pyrroline, pyrrole, pyrazolidine, imidazolidine, pyrrazoline, imidazoline, pyrrazole, imidazole, triazole, oxazole, isoxazole, isothiazole, thiazole, oxadiazole, thiadiazole, piperidine, pyridine, piperazine, pyridazine, pyrimidine, pyrazine, triazine, morpholine, oxazine, thiomorpholine, thiazine Alternatively Suitably $R^1$ is selected from the group consisting of $C(R^{11}R^{12}R^{13})$, wherein $R^{11}$, $R^{12}$, and $R^{13}$ are independently selected from H, $C_{1-6}$-alkyl, $NR^6R^7$ and $OR^8$, wherein $R^6$, $R^7$, and $R^8$ are defined as described herein, under the provision that not more than one of $R^{11}$, $R^{12}$, and $R^{13}$ is $NR^6R^7$ or $OR^8$. More preferably $R^{11}$, $R^{12}$ and $R^{13}$ are independently selected from H, $NR^6R^7$ and $OR^8$, wherein $R^6$, $R^7$, and $R^8$ are H, under the provision that not more than one of $R^{11}$, $R^{12}$, and $R^{13}$ is $NH_2$ or OH.

In another embodiments of the invention and/or embodiments thereof $R^2$ and $R^3$ are independently selected from the group consisting of H, substituted $C_{1-6}$-alkyl, or un-substituted $C_{1-6}$-alkyl. Suitably, $R^2$ and $R^3$ are H.

In embodiments of the invention and/or embodiments thereof $R^4$ is defined as described herein.

Suitably in embodiments of the invention and/or embodiments thereof $R^4$ is selected from the group consisting of H, $C_{1-6}$-alkyl, C(=O)$OR^8$, C(=O)$R^8$. More suitably $R^4$ is selected from the group consisting of H, —$OR^8$. Suitably $R^4$ is —$OR^8$, more suitably $R^4$ is OH.

In embodiments of the invention and/or embodiments thereof $R^5$ is defined as described herein, Suitably in embodiments of the invention and/or embodiments thereof $R^5$ is selected from H and $C_{1-2}$-alky, in particular H.

In embodiments of the invention and/or embodiments thereof $R^6$, $R^7$, $R^8$. $R^9$ and $R^{10}$ are defined as described herein.

The invention is also directed to method for treating an animal with an infection by bacteria comprising administering to the subject in need thereof an effective amount of a compound of the present invention and/or embodiments thereof with a pharmaceutically acceptable carrier, wherein the bacteria are at least one of the bacteria selected from the group of *Pasteurella multocida, Mannheimia haemolytica* and *Histophilus somni, Actinobacillus pleuropneumoniae, Bordetella bronchiseptica* and *Haemophilus parasuis*. Suitably the subject is a mammal and in some embodiments, a ruminant or swine.

In an embodiment the invention is directed to a method for treating a ruminant, preferably bovine, suffering from an infection by bacteria, comprising administering to the subject in need thereof an effective amount of a compound of the present invention and/or embodiments thereof with a pharmaceutically acceptable carrier, wherein the bacteria are at least one of the bacteria selected from the group of *Pasteurella multocida, Mannheimia haemolytica* and *Histophilus somni.*

In another embodiment the invention is directed a to method for treating a swine suffering from an infection by bacteria, comprising administering to the subject in need thereof an effective amount of a compound of the present invention and/or embodiments thereof with a pharmaceutically acceptable carrier, wherein the bacteria are at least one of the bacteria selected from the group of *Pasteurella multocida, Actinobacillus pleuropneumoniae, Bordetella bronchiseptica* and *Haemophilus parasuis.*

In yet another aspect, the invention is directed to a compound according to the present invention and/or embodiments thereof with a pharmaceutically acceptable carrier for use in the treatment of bovine respiratory disease or swine respiratory disease.

The invention provides further a pharmaceutical composition comprising an effective amount of a compound according to the invention and/or embodiments thereof with a pharmaceutically acceptable carrier thereof.

DETAILED DESCRIPTION

It was found that compounds according to formula (I) or the stereoisomer, pharmaceutically acceptable salt, ester, solvate, or prodrug thereof, are useful in the treatment of an infection by a bacteria causing Bovine Respiratory disease, such as *Mannheimia haemolytica Histophilus somni*, and *Pasteurella multocida*, In particular the compounds according to the invention and/or any embodiments thereof are useful in the treatment of an infection by *Mannheimia haemolytica* and/or *Histophilus somni*. Optionally, the compounds according to the invention and/or any embodiments thereof are useful in the treatment of an infection by *Pasteurella multocida*. Advantageously, the compounds according to the invention and/or any embodiments thereof are useful in the treatment of an infection by *Mannheimia haemolytica*, *Histophilus somni* and *Pasteurella multocida*.

It was found that compounds according to formula (I) or the stereoisomer, pharmaceutically acceptable salt, ester, solvate, or prodrug thereof, are useful in the treatment of an infection by bacteria causing Swine Respiratory disease, such as *Pasteurella multocida*, *Actinobacillus pleuropneumoniae*, *Bordetella bronchiseptica* and *Haemophilus parasuis*. In particular, the compounds according to the invention and/or any embodiments thereof are useful in the treatment of an infection by *Pasteurella multocida* and/or, *Actinobacillus pleuropneumoniae*. Optionally, the compounds according to the invention and/or any embodiments thereof are useful in the treatment of an infection by *Bordetella bronchiseptica*. Advantageously, the compounds according to the invention and/or any embodiments thereof are useful in the treatment of an infection by *Pasteurella multocida*, *Actinobacillus pleuropneumoniae*, *Bordetella bronchiseptica* and *Haemophilus parasuis*.

Increasingly there is a fear of multi-resistant bacteria. There is therefore a need for a specific antibiotic that can be used in an infection of a specific bacterium. Advantageously the compound according to the invention and/or any embodiments thereof is effective against *Mannheimia haemolytica*, *Histophilus somni Actinobacillus pleuropneumoniae*, *Bordetella bronchiseptica* and *Haemophilus parasuis* and/or *Pasteurella multocida* but not against other bacteria, such as those that are important in human health, such as *Straphyiococcus* spp. and *Streptrococcus* spp., *Acinetobacter* species, especially *Acinetobacter baumanii*.

Advantageously the compound according to the invention and/or any embodiments thereof is effective against *Mannheimia haemolytica*, *Histophilus somni* and/or *Pasteurella multocida* but not against other bacteria, such as those that are important in human health, such as *Straphyiococcus* spp. and *Streptrococcus* spp., *Acinetobacter* species, especially *Acinetobacter baumanii*.

Advantageously the compound according to the invention and/or any embodiments thereof is effective against *Actinobacillus pleuropneumoniae*, *Bordetella bronchiseptica* and/or *Haemophilus parasuis* but not against other bacteria, such as those that are important in human health, such as *Straphyiococcus* spp. and *Streptrococcus* spp., *Acinetobacter* species, especially *Acinetobacter baumanii*.

The following abbreviations and definitions are used throughout this application:

Generally, reference to a certain element such as hydrogen or H is meant to include all isotopes of that element. For example, if an R group is defined to include hydrogen or H, it also includes deuterium and tritium.

The phrase "alkyl" refers to alkyl groups that do not contain heteroatoms. Thus, the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus, the phrase alkyl groups includes primary alkyl groups, secondary alkyl groups, and tertiary alkyl groups. Preferred alkyl groups include straight and branched chain alkyl groups having 1 to 12 carbon atoms.

The phrase "substituted alkyl" refers to an alkyl group as defined above in which one or more bonds to a carbon (s) or hydrogen (s) are replaced by a bond to non-hydrogen and non-carbon atoms. If not further defined the "substituted alkyl" may be substituted by a group such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon (s) or hydrogen (s) atom is replaced by a higher-order bond (e. g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon (s) or hydrogen (s) atoms is replaced by a bond to an aryl, heterocyclyl group, or cycloalkyl group. Exemplary substituted alkyl groups include, among others, alkyl groups in which one or more bonds to a carbon or hydrogen atom is/are replaced by one or more bonds to fluorine atoms.

Another exemplary substituted alkyl group is the trifluoromethyl group and other alkyl groups that contain the trifluoromethyl group. Other exemplary substituted alkyl groups include those in which one or more bonds to a carbon or hydrogen atom is replaced by a bond to an oxygen atom such that the substituted alkyl group contains a hydroxyl, alkoxy, or aryloxy group. Still other exemplary substituted alkyl groups include alkyl groups that have an amine, or a substituted or unsubstituted alkylamine, dialkylamine, arylamine, (alkyl) (aryl) amine, diarylamine, heterocyclylamine, diheterocyclylamine, (alkyl) (heterocyclyl) amine, or (aryl) (heterocyclyl) amine group.

The phrase "alkenyl" refers to straight and branched chain and cyclic groups such as those described with respect to alkyl groups as defined above, except that at least one double bond exists between two carbon atoms. Examples include, but are not limited to vinyl, —CH=C(H)(CH$_3$), —CH=C (CH$_3$)$_2$, —C(CH$_3$)=C(H)$_2$, —C(CH)=C(H)(CH$_3$), —C(CH$_2$CH$_3$)=CH$_2$, cyclohexenyl, cyclopentenyl, cyclohexadienyl, butadienyl, pentadienyl, and hexadienyl among others.

The phrase "substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to straight and branched chain groups such as those described with respect to alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C (CH$_2$CH$_3$) among others.

The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "cycloalkyl" refers to a non-aromatic monocyclic or polycyclic alkyl group consisting solely of carbon and hydrogen atoms, and which may be saturated or unsaturated. Cycloalkyl may include fused or bridged ring systems, having from three to fifteen carbon atoms, preferably having from three to ten carbon atoms (C$_3$-C$_{10}$-cycloalkyl), and which may be saturated or unsaturated. Monocyclic radicals include, for example, cyclopropyl, cyclobutyl, cyclopentyl, cyclohexyl, cycloheptyl, cyclooctyl, and the like. Polycyclic radicals include, for example, adamantine, norbornane, decalinyl, 7,7-dimethyl-bicyclo[2.2.1]heptanyl, and the like. If not further defined, cycloalkyl may be substituted with substituents as indicated above with substituted alkyl group.

The phrase "heterocyclic ring" refers to both aromatic, "heteroaryl" and nonaromatic, "heterocyclyl", ring compounds including monocyclic, bicyclic, and polycyclic ring compounds such as, but not limited to, quinuclidinyl, containing 3 or more ring members of which one or more is a heteroatom such as, but not limited to, N, O, and S.

Heterocyclyl refers to a 3- to 18-membered non-aromatic ring radical which consists of two to seventeen carbon atoms and from one to ten heteroatoms selected from the group consisting of nitrogen, oxygen and sulfur. Unless stated otherwise specifically in the specification, the heterocyclyl radical may be a monocyclic, bicyclic or polycyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e. g. 4H-1, 2,4-triazolyl, lu-1, 2, 3-triazolyl, 2H-1, 2,3-triazolyl etc.), tetrazolyl, (e. g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e. g. 1,2, 4-oxadiazolyl, 1,3, 4-oxadiazolyl, 1,2, 5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e. g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e. g. 1,2, 3-thiadiazolyl, 1,2, 4-thiadiazolyl, 1,3, 4-thiadiazolyl, 1,2, 5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e. g. 2H-1, 4-benzothiazinyl, etc.), dihydrobenzothiazinyl (e. g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e. g. 1, 3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1, 4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1, 1-dioxide. Exemplary heterocyclyl groups contain 5 or 6 ring members. Other exemplary heterocyclyl groups include morpholine, piperazine, piperidine, pyrrolidine, imidazole, pyrazole, 1,2, 3-triazole, 1,2, 4-triazole, tetrazole, thiomorpholine, thiomorpholine in which the S atom of the thiomorpholine is bonded to one or more 0 atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to a heterocyclyl group as defined above in which one of the ring members is bonded to a non-hydrogen atom such as described herein with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "aryl" refers to aryl groups that do not contain heteroatoms. Thus, the phrase includes, but is not limited to, groups such as phenyl, biphenyl, anthracenyl, naphtenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. An exemplary unsubstituted aryl group is phenyl. Unsubstituted aryl groups may be bonded to one or more carbon atom(s), oxygen atom(s), nitrogen atom(s), and/or sulfur atom (s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e. g. dihydronaphthyl or tetrahydronaphthyl). Thus, the phrase "substituted aryl" includes, but is not limited to tolyl, and hydroxyphenyl among others. If not further defined the "substituted aryl group" may be substituted by a group such as straight and branched chain alkyl groups, —$CH_3$, —$C_2H_5$, —$CH_2OH$, —OH, —$OCH_3$, —$OC_2H_5$, —$OCF_3$, —CN, —$NO_2$, —$CO_2H$, —$CO_2CH_3$, —$CONH_2$, —$NH_2$, —F, —Cl, Br, —$CF_3$, —$N(CH_3)_2$, —$NHSO_2CH_3$, —$NHCOCH_3$.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" as used herein refers to a heteroaryl group as defined herein substituted by independent replacement of one, two or three of the hydrogen atoms thereon. Exemplary substituents may include Cl, Br, F, I, OH, CN, $C_{1-6}$-alkoxy, $C_{1-6}$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

Exemplary substituents include straight and branched chain alkyl groups, —$CH_3$, —$C_2H_5$, —$CH_2OH$, —OH, —$OCH_3$, —$OC_2H_5$, —$OCF_3$, —CN, —$NO_2$, —$CO_2H$, —$CO_2CH_3$, —$CONH_2$, —$NH_2$, —F, —Cl, —Br, —$CF_3$, —$N(CH_3)_2$, —$NHSO_2CH_3$, —$NHCOCH_3$.

The term "biaryl" refers to a group or substituent to which two aryl groups, which are not condensed to each other, are bound. Exemplary biaryl compounds include, for example, phenylbenzene, diphenyldiazene, 4-methylthio-1-phenyl-benzene, phenoxybenzene, (2-phenylethynyl) benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl) phenyl] acetamide, 1,4-diphenylbenzene, N-[4-(2-phenylethynyl) phenyl]-2-[benzylamino] acetamide, 2-amino-N-[4-(2-phenylethynyl) phenyl] propanamide, 2-amino-N-[4-(2-phenylethynyl) phenyl] acetamide, 2-(cyclopropylamino)-N-[4-(2-phenylethynyl) phenyl] acetamide, 2-(ethylamino)-N-[4-(2-phenylethynyl) phenyl] acetamide, 2-[(2-methylpropyl) amino]-N-[4-(2-phenylethynyl) phenyl] acetamide, 5-phenyl-2H-benzo[d]1, 3-dioxolene, 2-chloro-1-methoxy4-phenylbenzene, 2-[(imidazolylmethyl) amino]-N-[4-(2-phenylethynyl) phenyl] acetamide, 4-phenyl-1-phenoxybenzene, N-(2-aminoethyl) [4-(2-phenylethynyl) phenyl] carboxamide, 2-{[(4-fluorophenyl) methyl] amino}-N-[4-(2-phenylethynyl) phenyl] acetamide, 2-{[(4-methylphenyl) methyl] amino}-N-[4-(2-phenylethynyl) phenyl] acetamide, 4-phenyl-1-(trifluoromethyl) benzene, 1-butyl-4-phenylbenzene, 2-(cyclohexylamino)-N-[4-(2-phenylethynyl) phenyl] acetamide, 2-(ethylmethylamino)-N-[4-(2-phenylethynyl) phenyl] acetamide, 2-(butylamino)-N-[4-(2-phenylethynyl) phenyl] acetamide, N-[4-(2-phenylethynyl) phenyl]-2-(4-pyridylamino) acetamide, N-[4-(2-phenylethynyl) phenyl]-2-(quinuclidin-3-ylamino) acetamide, N-[4-(2-phenylethynyl) phenyl] pyrrolidin-2-ylcarboxamide, 2-amino-3-methyl-N-[4-(2-phenylethynyl) phenyl] butanamide, 4-(4-phenylbuta-1, 3-diynyl) phenylamine, 2-(dimethylamino)-N-[4-(4-phenylbuta-1, 3-diynyl) phenyl] acetamide, 2-(ethylamino)-N-[4-(4-phenylbuta-I, 3-diynyl) phenyl] acetamide, 4-ethyl-1-phenylbenzene, 1-[4-(2-phenylethynyl) phenyl] ethan-1-one, N-(1-carbamoyl-2-hydroxypropyl) [4-(4-phenylbuta-1, 3-diynyl) phenyl] carboxamide, N-[4-(2-phenylethynyl) phenyl] propanamide, 4-methoxyphenyl phenyl ketone, phenyl-N-benzamide, (tert-butoxy)-N-[(4-phenylphenyl) methyl] carboxamide, 2-(3-phenylphenoxy) ethanehydroxamic acid, 3-phenylphenyl propanoate, 1-(4-ethoxyphenyl)-4-methoxybenzene, and [4-(2-phenylethynyl) phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl) pyridine, phenylpyrazole, 5-(2-phenylethynyl)-1, 3-dihydropyrimidine-2,4-dione, 4-phenyl-1, 2,3-thiadiazole, 2-(2-phenylethynyl) pyrazine, 2-phenylthiophene, phenylimidazole, 3-(2-piperazinylphenyl)furan, 3-(2, 4-dichlorophenyl)-4-methylpyrrole, and the like. Optionally substituted heteroarylaryl groups include: 5-(2-phenylethynyl) pyrimidine-2-ylamine, 1-methoxy-4-(2-thienyl) benzene, 1-methoxy-3-(2-thienyl) benzene, 5-methyl-2-phenylpyridine, 5-methyl-3-phenylisoxazole, 2-[3-(trifluoromethyl) phenyl] furan, 3-fluoro-5-(2-furyl)-2-methoxy-1-prop-2-enylbenzene, (hydroxyimino) (5-phenyl (2-thienyl)) methane, 5-[(4-methylpiperazinyl) methyl]-2-phenylthiophene, 2-(4-ethylphenyl) thiophene, 4-methylthio-1-(2-thienyl) benzene, 2-(3-nitrophenyl) thiophene, (tert-butoxy)-N-[(5-phenyl (3-pyridyl)) methyl] carboxamide, hydroxy-N-[(5-phenyl (3-pyridyl)) methyl] amide, 2-(phenyhnethylthio) pyridine, and benzylimidazole.

The term "heteroaryl" refers to a biaryl group where both of the aryl groups are heteroaryl groups. Exemplary heteroaryl groups include, for example, 3-pyridylimidazole, 2-imidazolylpyrazine, and the like. Preferred optionally substituted heteroaryl groups include: 2-(4-piperazinyl-3- pyridyl) furan, diethyl (3-pyrazin-2-yl (4-pyridyl)) amine, and dimethyl {2-[2-(5-methylpyrazin-2-yl) ethynyl] (4-pyridyl)} amine.

"Optionally substituted" refers to the optional replacement of hydrogen with one or more monovalent or divalent radicals. Optionally substituted groups include those described herein, for each group in which a distinct definition for substitution is supplied. Additionally, suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

The term "protected" with respect to hydroxyl groups, amine groups, and sulfhydryl groups refers to forms of these functionalities that are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) that can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate.

Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioether such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms.

Representative examples of particular esters include, but are not limited to, formates, acetates, propionates, butyrates, acrylates and ethylsuccinates.

The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable prodrugs" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention.

The term "antibacterial agent" refers to agents synthesized or modified in the laboratory that have either bactericidal or bacteriostatic activity.

An "active" agent in this context will inhibit the growth of *Mannheimia haemolytica, Histophilus somni, Actinobacillus pleuropneumoniae, Bordetella bronchiseptica Haemophilus parasuis* and/or *Pasteurella multocida.*

Alternatively, an "active" agent in this context will inhibit the growth of *Mannheimia haemolytica, Histophilus somni,* and/or *Pasteurella multocida.*

Alternatively, an "active" agent in this context will inhibit the growth of *Actinobacillus pleuropneumoniae, Bordetella bronchiseptica* and/or *Haemophilus parasuis.*

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

The present invention provides compounds that are useful in the treatment of an infection by *Mannheimia haemolytica*, and/or *Histophilus somni* and/or *Pasteurella multocida*, and/or *Actinobacillus* pleuropneumoniae, and/or *Bordetella bronchiseptica* and/or *Haemophilus parasuis*, and pharmaceutical formulations including the compounds and methods of treating an infection caused by *Mannheimia haemolytica* and/or *Histophilus somni* and/or *Pasteurella multocida*, and/or *Actinobacillus pleuropneumoniae*, and/or *Bordetella bronchiseptica* and/or *Haemophilus parasuis.*

The present invention provides compounds that are useful in the treatment of an infection by *Mannheimia haemolytica*, and/or *Histophilus somni* and/or *Pasteurella multocida*, and, pharmaceutical formulations including the compounds and methods of treating an infection caused by *Mannheimia haemolytica* and/or *Histophilus somni* and/or *Pasteurella multocida*.

The present invention provides compounds that are useful in the treatment of an infection by *Actinobacillus pleuropneumoniae*, and/or *Bordetella bronchiseptica* and/or *Haemophilus parasuis*, and pharmaceutical formulations including the compounds and methods of treating an infection caused by *Actinobacillus pleuropneumoniae*, and/or *Bordetella bronchiseptica* and/or *Haemophilus parasuis*.

The invention provides a compound according to the invention and/or embodiments thereof, wherein $R^1$ is selected from the group consisting of $C(R^{11}R^{12}R^{13})$.

In some embodiments of the invention and/or embodiments thereof the compound is a compound according to formula (IV)

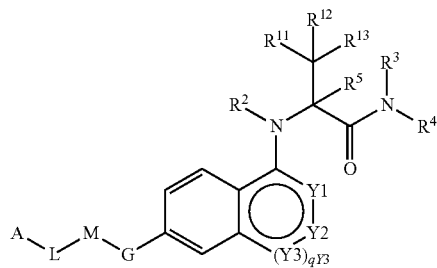

(IV)

or a stereoisomer, pharmaceutically acceptable salt, ester, solvate, or prodrug thereof, wherein A, L, M, G, Y1, Y2, Y3, qY3 $R^2$, $R^3$, $R^4$, $R^5$, $R^{11}$, $R^{12}$ and $R^{13}$ are defined as in any of the embodiments described herein.

In some embodiments of the invention and/or embodiments thereof the compound is a compound according to formula (V)

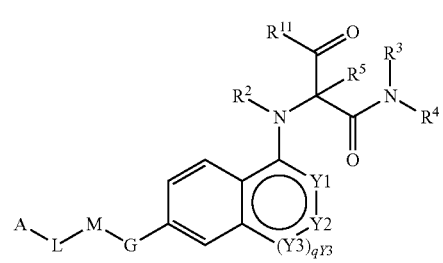

(V)

or a stereoisomer, pharmaceutically acceptable salt, ester, solvate, or prodrug thereof, wherein A, L, M, G, Y1, Y2, Y3, qY3 $R^2$, $R^3$, $R^4$, $R^5$, and $R^{11}$, are defined as in any of the embodiments described herein.

In some embodiments of the invention and/or embodiments thereof the compound is a compound according to formula (VI)

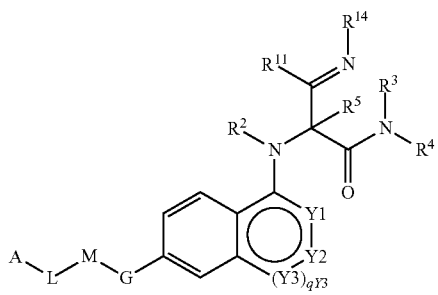

(VI)

or a stereoisomer, pharmaceutically acceptable salt, ester, solvate, or prodrug thereof, wherein A, L, M, G, Y1, Y2, Y3, qY3 $R^2$, $R^3$, $R^4$, $R^5$, $R^{11}$, and $R^{14}$ are defined as in any of the embodiments described herein.

Suitably $R^{11}$ is selected from the group consisting of H, and $C_{1-6}$-alkyl, more suitably $C_{1-6}$-alkyl.

In another suitable embodiment of the present invention and/or embodiments thereof, $R^{12}$ is selected from the group consisting of H, $C_{1-6}$-alkyl, and $C_{1-6}$-alkyl substituted with a substituent from the group consisting of —$SR^8$, —$OR^8$, —C(=O)$OR^8$, —$NR^6R^7$, —$SO_2NR^6R^7$, —$SO_2R^8$.

In another suitable embodiment of the present invention and/or embodiments thereof, $R^{12}$ is selected from the group consisting of H, $C_{1-6}$-alkyl, and $C_{1-6}$-alkyl substituted with a substituent from the group consisting of —$SR^8$, —$OR^8$, —C(=O)$OR^8$, —$NR^6R^7$, —$SO_2NR^6R^7$, —$SO_2R^8$.

Suitably in certain embodiments of the present invention and/or embodiments thereof, the substituted $C_{1-6}$-alkyl in $R^{12}$ is substituted with a substituent selected from the group consisting of —$SR^8$, —$OR^8$, —$NR^6R^7$, —$SO_2NR^8R^7$, —$SO_2R^8$.

Suitably in certain embodiments of the present invention and/or embodiments thereof, the substituted $C_{1-6}$-alkyl in $R^{12}$ is substituted with a substituent selected from the group consisting of —$SCH_3$, —OH, —$NH_2$, —$SO_2CH_3$.

In some embodiments of the present invention and/or embodiments thereof, $R^{13}$ is selected from the group consisting of H, $C_{1-6}$-alkyl, aryl, —$SR^8$, —$OR^8$, —$NR^6R^7$, —$SO_2R^8$, nitro, —C(=O)$NR^6R^7$, and $C_{1-6}$-alkyl substituted with a substituent selected from the group consisting of —$SR^8$, —C(=O)$NR^6R^7$, —$SO_2NR^8R^7$, —$SO_2R^8$, nitro, cyano, —$OR^8$, —C(=O)$OR^8$, —$NR^9C(=NR^{14})$ $NR^6R^7$.

In some embodiments of the present invention and/or embodiments thereof, $R^{13}$ is selected from the group consisting of H, $C_{1-6}$-alkyl, aryl, —$SR^8$, —$SO_2R^8$, nitro, —C(=O) $NR^6R^7$, and $C_{1-6}$-alkyl substituted with a substituent selected from the group consisting of —$SR^8$, —C(=O) $NR^6R^7$, —$SO_2NR^8R^7$, —$SO_2R^8$, nitro, cyano, —$OR^8$, —C(=O)$OR^8$, —$NR^8C(=NR^{14})NR^8R^7$.

In some embodiments of the present invention and/or embodiments thereof, $R^{13}$ is selected from the group consisting of H, $C_{1-6}$-alkyl, —$SR^8$, —$OR^8$, —$NR^6R^7$, —$SO_2R^8$, nitro, —C(=O)$NR^6R^7$, and $C_{1-6}$-alkyl substituted with a substituent selected from the group consisting of —$SR^8$, —C(=O)$NR^6R^7$, —$SO_2NR^8R^7$, —$SO_2R^8$, nitro, cyano, —$OR^8$, —C(=O)$OR^8$, —$NR^8C(=NR^{14})$ $NR^6R^7$.

In some embodiments of the present invention and/or embodiments thereof, $R^{13}$ is selected from the group consisting of H, $C_{1-6}$-alkyl, $-SR^8$, $-SO_2R^8$, nitro, $-C(=O)NR^6R^7$, and $C_{1-6}$-alkyl substituted with a substituent selected from the group consisting of $-SR^8$, $-C(=O)NR^6R^7$, $-SO_2NR^8R^7$, $-SO_2R^8$, nitro, cyano, $-OR^9$, $-C(=O)OR^9$, $-NR^9C(=NR^{14})NR^8R^7$.

In some embodiments of the present invention and/or embodiments thereof, $R^{13}$ is selected from the group consisting of H, $C_{1-6}$-alkyl, $-SR^8$, $-OR^8$, $-NR^6R^7$, $-SO_2R^8$, and $C_{1-6}$-alkyl substituted with a substituent selected from the group consisting of $-SR^8$, $-C(=O)NR^6R^7$, $-SO_2R^8$, $-SO_2NR^8R^7$, nitro, cyano, $-OR^8$, $-C(=O)OR^8$, $-NR^8C(=NR^{14})NR^6R^7$.

In some embodiments of the present invention and/or embodiments thereof, $R^{13}$ is selected from the group consisting of H, $C_{1-6}$-alkyl, $-SR^8$, $-SO_2R^8$, and $C_{1-6}$-alkyl substituted with a substituent selected from the group consisting of $SR^8$, $-C(=O)NR^9R^{10}$, $-SO_2R^8$, $-SO_2NR^6R^7$, nitro, cyano, $-OR^8$, $-C(=O)OR^8$, $-NR^8C(=NR^{14})NR^6R^7$.

In some embodiments of the present invention and/or embodiments thereof, $R^{13}$ is selected from the group consisting of H, $C_{1-6}$-alkyl, $-SR^8$, $-OR^8$, $-NR^6R^7$, $-SO_2R^8$.

In some embodiments of the present invention and/or embodiments thereof, $R^{13}$ is selected from the group consisting of H, $C_{1-6}$-alkyl, $-SR^8$, $-SO_2R^8$.

In some embodiments of the present invention and/or embodiments thereof, $R^{13}$ is selected from the group consisting of $-SR^8$, $-OR^8$, $-NR^6R^7$, $-SO_2R^8$.

In some embodiments of the present invention and/or embodiments thereof, $R^{13}$ is selected from the group consisting of $-SR^8$, $-OR^8$, $-SO_2R^8$.

In some embodiments of the present invention and/or embodiments thereof, $R^{13}$ is selected from the group consisting of $-SR^8$, and $-SO_2R^8$.

In some embodiments of the present invention and/or embodiments thereof, $R^{13}$ is selected from the group consisting of $-SR^8$, and $-SO_2R^8$ and wherein $R^{11}$ and $R^{12}$ are methyl.

In some embodiments of the present invention and/or embodiments thereof, $R^{13}$ is not OH or $NH_2$.

Suitably in certain embodiments of the present invention and/or embodiments thereof, the substituted $C_{1-6}$-alkyl in $R^{13}$ is substituted with a substituent selected from the group consisting of $SR^8$, $-C(=O)NR^6R^7$, $-SO_2R^8$, $-SO_2NR^6R^7$, nitro, cyano, $-OR^8$, $-C(=O)OR^8$, $-NR^8C(=NR^{14})NR^6R^7$.

Suitably in certain embodiments of the present invention and/or embodiments thereof, the substituted $C_{1-6}$-alkyl in $R^{13}$ is substituted with a substituent selected from the group consisting of $SR^8$, $-C(=O)NR^6R^7$, $-SO_2R^8$, $-SO_2NR^6R^7$, nitro, $-OR^8$, $-C(=O)OR^8$.

Suitably in certain embodiments of the present invention and/or embodiments thereof, the substituted $C_{1-6}$-alkyl in $R^{13}$ is substituted with a substituent selected from the group consisting of $SR^8$, $-SO_2NR^6R^7$, $SO_2R^8$, $-OR^8$.

Suitably in certain embodiments of the present invention and/or embodiments thereof, the substituted $C_{1-6}$-alkyl in $R^{13}$ is substituted with a substituent selected from the group consisting of $SCH_3$, $-SO_2CH_3$, $-OH$.

In some embodiments of the present invention and/or embodiments thereof, $R^{13}$ and $R^2$ together with the N atom which $R^2$ is attached to, form a saturated or unsaturated heterocycle having 3 to 6 ring atoms wherein 1 ring atom is N and 0, 1 or 2 further ring atoms are selected from N, S, and O the rest of the ring atoms being C.

Suitably in certain embodiments of the present invention and/or embodiments thereof, $R^{13}$ and $R^2$ together with the N atom which $R^2$ is attached to, form a heterocycle selected from the group consisting of aziridine, azirine, azetidine, dihydroazete, azete, diazetidine, pyrrolidine, pyrroline, pyrrole, pyrazolidine, imidazolidine, pyrrazoline, imidazoline, pyrrazole, imidazole, triazole, oxazole, isoxazole, isothiazole, thiazole, oxadiazole, thiadiazole, piperidine, pyridine, piperazine, pyridazine, pyrimidine, pyrazine, triazine, morpholine, oxazine, thiomorpholine, thiazine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, pyrazolidine, imidazolidine, pyrrazoline, imidazoline, pyrrazole, imidazole, triazole, oxazole, isoxazole, isothiazole, thiazole, oxadiazole, thiadiazole, piperidine, pyridine, piperazine, pyridazine, pyrimidine, pyrazine, triazine, morpholine, oxazine, thiomorpholine, thiazine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, pyrazolidine, imidazolidine, pyrrazoline, imidazoline, pyrrazole, imidazole, triazole, oxazole, isothiazole, thiazole, piperidine, pyridine, piperazine, pyrimidine, pyrazine, morpholine, thiomorpholine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, imidazole, oxazole, thiazole, piperidine, pyridine, piperazine, pyrimidine, morpholine.

Suitably in certain embodiments of the present invention and/or embodiments thereof, $R^{13}$ and $R^2$ together with the N atom which $R^2$ is attached to, form a heterocycle selected from the group consisting of pyrrolidine, imidazoline, oxazole, thiazole, piperidine, pyridine, morpholine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, imidazole, oxazole, isoxazole, isothiazole, thiazole, thiadiazole, piperidine, pyridine, piperazine, pyrimidine, pyrazine, morpholine, thiomorpholine.

Suitably when $R^{13}$ is OH or $NH_2$ and $R^{12}$ is methyl then $R^{11}$ cannot be H.

Suitably when $R^{13}$ is $NH_2$ and $R^{12}$ is methyl $R^{11}$ cannot be methyl.

Suitably when $R^{13}$ is OH and $R^{12}$ is methyl then $R^{11}$ cannot be methyl.

Suitably when $R^{13}$ is $NH_2$ and $R^{12}$ is H then $R^{11}$ cannot be H.

Suitably when $R^{13}$ is OH and $R^{12}$ is H then $R^{11}$ cannot be H.

Suitably when $R^{13}$ is $CH_3$ and $R^{12}$ is $CH_3$ then $R^{11}$ cannot be H.

Suitably in certain embodiments of the present invention and/or embodiments thereof, $R^{14}$ is selected from the group consisting of H, $C_{1-6}$-alkyl, —$OR^9$. Suitably in certain embodiments of the present invention and/or embodiments thereof, $R^{14}$ is selected from the group consisting of H, $C_{1-6}$-alkyl, —OH.

In an embodiment $R^1$ is selected from —CCH(CH$_3$)OH and —C(CH$_3$)$_2$NH$_2$.

Optionally, in an embodiment of the invention and/or embodiments thereof A is selected from the group consisting of $NR^{41}R^{42}$ and $NO_2$, wherein
- $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl and $C_1$-$C_6$-alkyl substituted with heterocyclyl, or wherein
- $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S and O;
- wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$—, carbonyl, —C(=O)—$OR^{45}$—, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{45}$—, —$SO_2R^{45}$—, —$SO_2NR^{43}R^{44}$, —C(=O)$NR^{43}R^{44}$—, $C_{1-6}$-alkyl substituted with hydroxy; wherein $R^{43}$, $R^{44}$, $R^{45}$ are independently chosen from H or $C_{1-6}$-alkyl.

Optionally, in an embodiment of the invention and/or embodiments thereof A is selected from the group consisting of $NR^{41}R^{42}$ and $NO_2$, wherein
- $R^{41}$ and $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$, $C_1$-$C_6$-alkyl substituted with aryl, $C_1$-$C_6$-alkyl substituted with heteroaryl, $C_1$-$C_6$-alkyl substituted with heterocyclyl, or wherein
- $R^{41}$ and $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by wherein $R^{41}$ and $R^{42}$ together with the N atom to which they are attached is optionally substituted with a substituent selected from the group consisting of $C_{1-6}$-alkyl, $C_{3-8}$-cycloalky, carbonyl halogen, $C_{1-6}$-alkyl substituted with halo, aryl, heteroaryl, $C_1$-$C_6$-alkyl substituted with aryl, cyano, hydroxy, —$SR^{45}$—, —$SO_2R^{45}$—, $SO_2NR^{43}R^{44}$, —C(=O)$NR^{43}R^{44}$—, $C_{1-6}$-alkyl substituted with hydroxy, wherein $R^{43}$, $R^{44}$, $R^{45}$, are independently chosen from H or $C_{1-6}$-alkyl.

Optionally, in an embodiment of the invention and/or embodiments thereof A is selected from the group consisting of $NR^{41}R^{42}$ and $NO_2$, wherein
- $R^{41}$ and $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$, $C_1$-$C_6$-alkyl substituted with aryl, $C_1$-$C_6$-alkyl substituted with heteroaryl, $C_1$-$C_6$-alkyl substituted with heterocyclyl, or wherein
- $R^{41}$ and $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by wherein $R^{41}$ and $R^{42}$ together with the N atom to which they are attached is optionally substituted with a substituent selected from the group consisting of $C_{1-6}$-alkyl, —$NR^{43}R^{44}$—, carbonyl, halogen, cyano, hydroxy, —$SR^{45}$, —$SO_2NR^{45}$, $SO_2NR^{43}R^{44}$, —C(=O)$NR^{43}R^{44}$—, wherein $R^{43}$, $R^{44}$, $R^{45}$ are independently chosen from H or $C_{1-6}$-alkyl Optionally, in an embodiment of the invention and/or embodiments thereof A is selected from the group consisting of $NR^{41}R^{42}$ and $NO_2$, wherein
- $R^{41}$ and $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$, $C_1$-$C_6$-alkyl substituted with aryl, $C_1$-$C_6$-alkyl substituted with heteroaryl, $C_1$-$C_6$-alkyl substituted with heterocyclyl, or wherein
- $R^{41}$ and $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by $R^{41}$ and $R^{42}$ together with the N atom to which they are attached is optionally substituted with a substituent selected from the group consisting of $C_{1-6}$-alkyl, carbonyl, amino, halogen, cyano, and hydroxy.

Optionally, in an embodiment of the invention and/or embodiments thereof A is selected from the group consisting of $NR^{41}R^{42}$ and $NO_2$, wherein
- $R^{41}$ and $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$, $C_1$-$C_6$-alkyl substituted with aryl, $C_1$-$C_6$-alkyl substituted with heteroaryl, $C_1$-$C_6$-alkyl substituted with heterocyclyl, or wherein
- wherein $R^{41}$ and $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O.

$R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S and O;

wherein the alkyl, alkenyl, alkynyl, cycloalkyl, aryl, heterocyclyl, heteroaryl, alkyloxy or the heterocyclic ring formed by $R^{A1}$ and $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$—, carbonyl, —C(=O)—$OR^{A5}$—, halogen atom, $C_{1-6}$-alkyl substituted with halo, $C_{1-6}$-alkyloxy-$C_1$-$C_6$-, aryl, heteroaryl, $C_1$-$C_6$-alkyl substituted with aryl, cyano, hydroxy, —$SR^{A5}$—, —$SO_2R^{A5}$—, $SO_2NR^{A3}R^{A4}$, —C(=O)$NR^{A3}R^{A4}$—, $C_{1-6}$-alkyl substituted with hydroxy; wherein $R^{A3}$, $R^{A4}$, $R^{A5}$ are independently chosen from H or $C_{1-6}$-alkyl.

In yet another embodiment of the invention and/or embodiments thereof, $R^{A1}$ and $R^{A2}$ together with the N atom to which they are attached can form a saturated or unsaturated heterocyclic ring having 3 to 10 ring atoms, wherein 1 ring atom is N and wherein 0, 1, 2, or 3 further ring atoms are selected from N, S, and O.

In yet another embodiment of the invention and/or embodiments thereof, $R^{A1}$ and $R^{A2}$ together with the N atom to which they are attached can form a saturated or unsaturated heterocyclic ring having 3 to 8 ring atoms, wherein 1 ring atom is N and wherein 0, 1, 2, or 3 further ring atoms are selected from N, S, and O.

In yet another embodiment of the invention and/or embodiments thereof, $R^{A1}$ and $R^{A2}$ together with the N atom to which they are attached can form a saturated or unsaturated heterocyclic ring selected from the group consisting of azetidinyl, azetyl, diazetidinyl, pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolyl, isoxazolyl, isothiazolyl, thiazolyl, oxoadiazolyl, thiadiazolyl, oxazolidonyl, piperidinyl, pyridinyl, piperazinyl, pyridazinyl, pyrimidinyl, pyrazinyl, triazinyl, morpholinyl, oxazinyl, thiomorpholinyl, thiazinyl, thiomorpholinyl dioxide, indolyl, indolinyl, isoindolyl, benzimidazolyl, azaindolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$ and $R^{A2}$ together with the N atom to which they are attached can form a saturated or unsaturated heterocyclic ring selected from the group consisting of pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolyl, isoxazolyl, isothiazolyl, thiazolyl, thiadiazolyl, oxazolidonyl, piperidinyl, pyridinyl, piperazinyl, pyridazinyl, pyrimidinyl, pyrazinyl, triazinyl, morpholinyl, thiomorpholinyl, thiazinyl, thiomorpholinyl dioxide, indolyl, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$ and $R^{A2}$ together with the N atom to which they are attached can form a saturated or unsaturated heterocyclic ring selected from the group consisting of pyrrolidinyl, pyrrolinyl, pyrrolyl, imidazolidinyl, pyrazolinyl, imidazolinyl, pyrazolyl, imidazolyl, oxazolyl, isoxazolyl, thiazolyl, thiadiazolyl, piperidinyl, pyridinyl, piperazinyl, pyrimidinyl, pyrazinyl, morpholinyl, thiomorpholinyl, thiomorpholinyl dioxide, indolyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$ and $R^{A2}$ together with the N atom to which they are attached can form a saturated or unsaturated heterocyclic ring selected from the group consisting of pyrrolidinyl, pyrrolinyl, pyrrolyl, imidazolidinyl, pyrazolinyl, imidazolinyl, pyrazolyl, imidazolyl, oxazolyl, isoxazolyl, thiazolyl, thiadiazolyl, piperidinyl, pyridinyl, piperazinyl, pyrimidinyl, pyrazinyl, morpholinyl, thiomorpholinyl, thiomorpholinyl dioxide, indolyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$ and $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl, Suitably, in an embodiment of the invention and/or embodiments thereof —$NR^{A1}R^{A2}$ is selected from the group consisting of

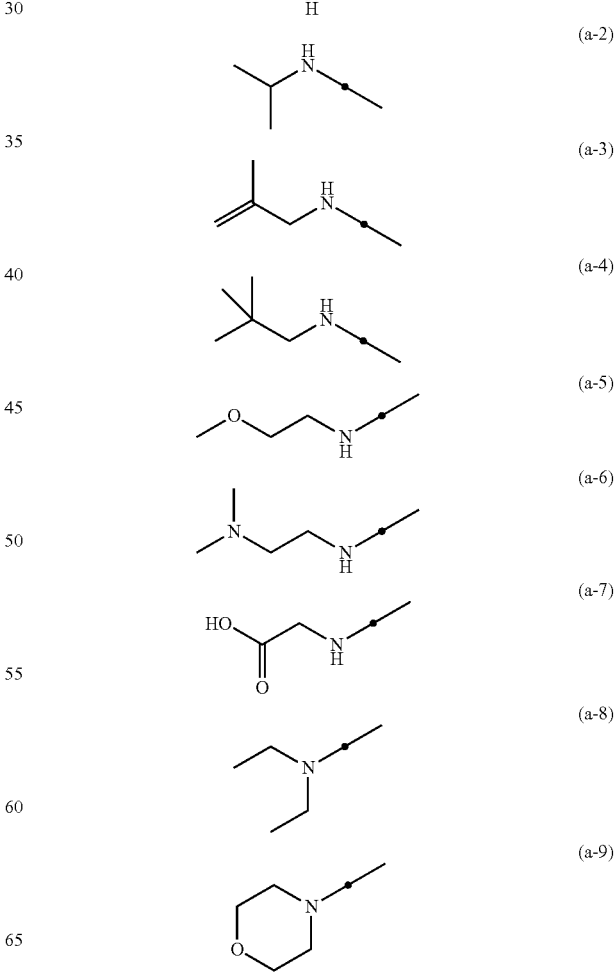

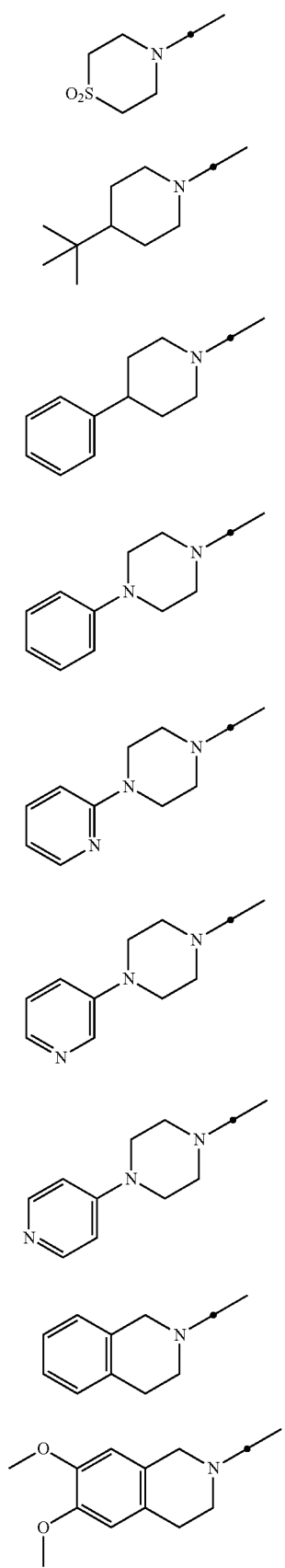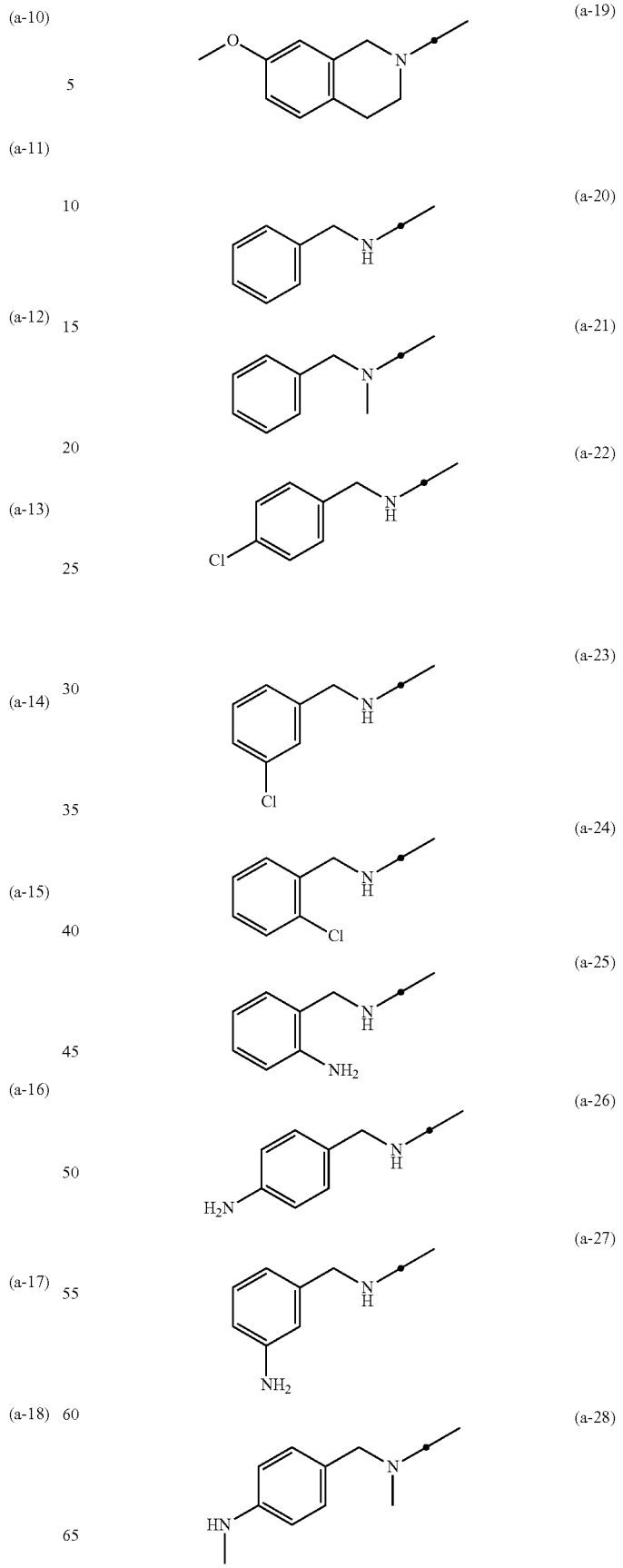

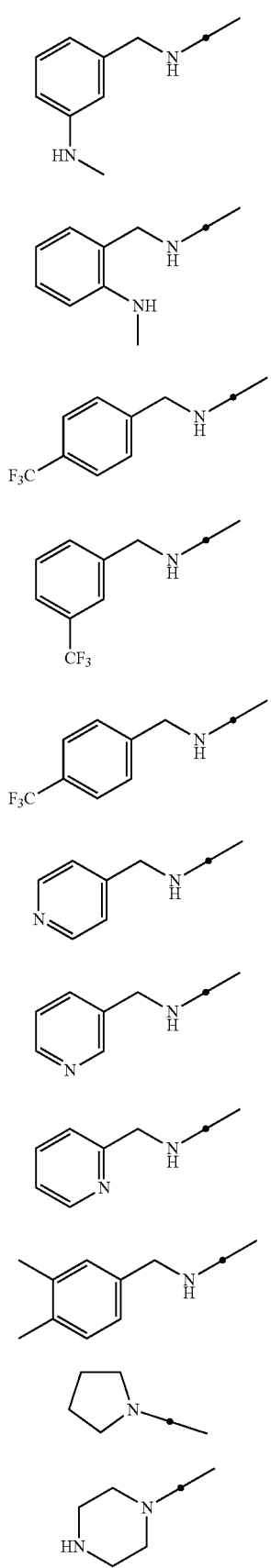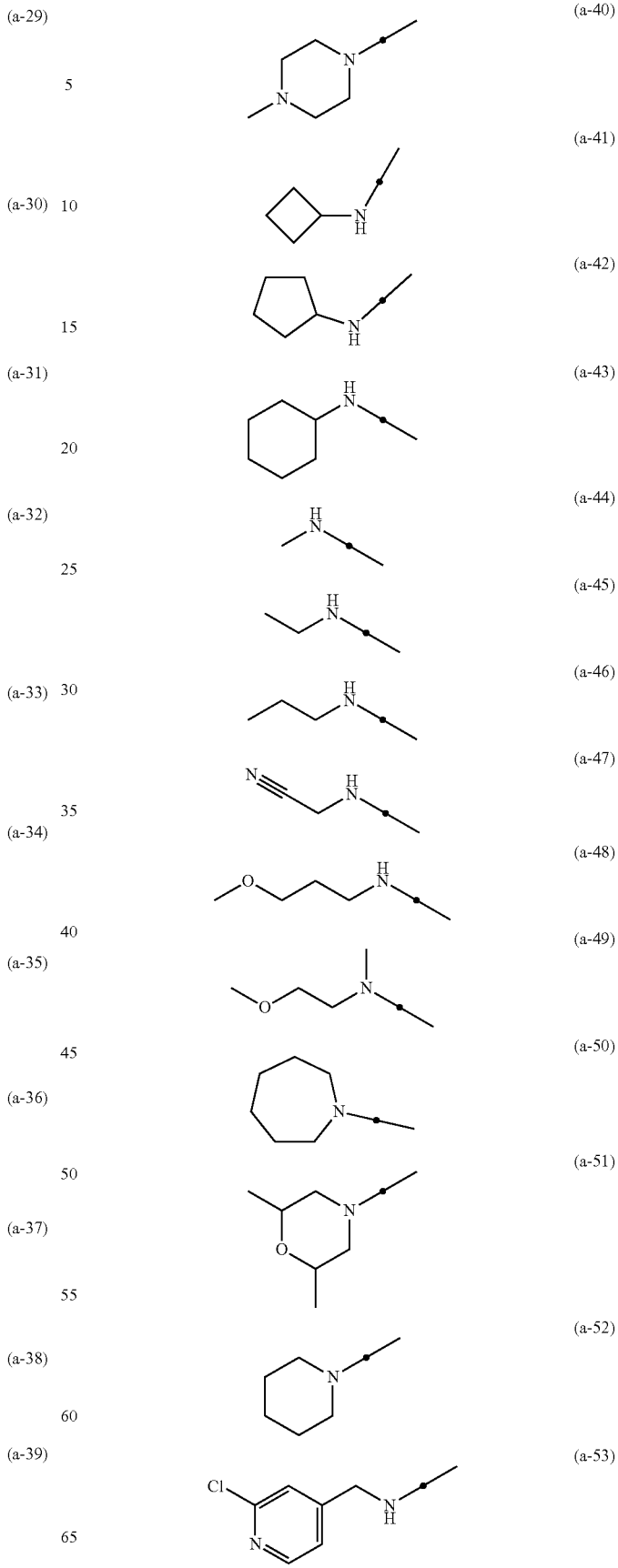

-continued
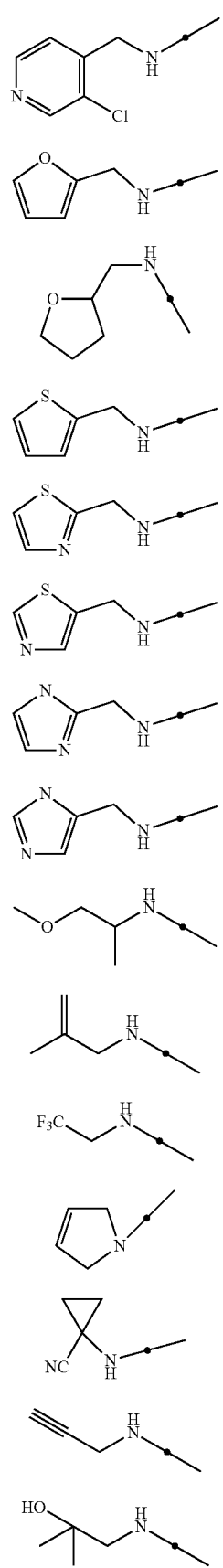
(a-54)
(a-55)
(a-56)
(a-57)
(a-58)
(a-59)
(a-60)
(a-61)
(a-62)
(a-63)
(a-64)
(a-65)
(a-66)
(a-67)
(a-68)
-continued
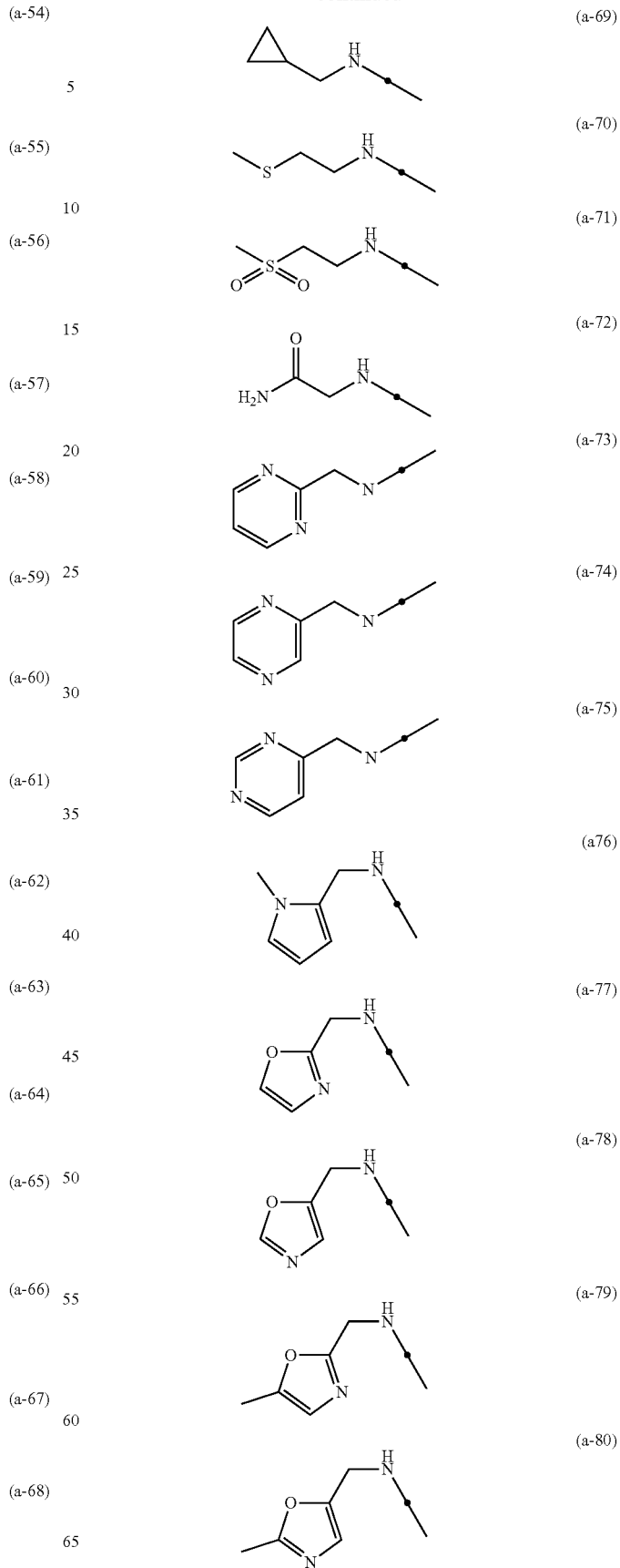
(a-69)
(a-70)
(a-71)
(a-72)
(a-73)
(a-74)
(a-75)
(a76)
(a-77)
(a-78)
(a-79)
(a-80)

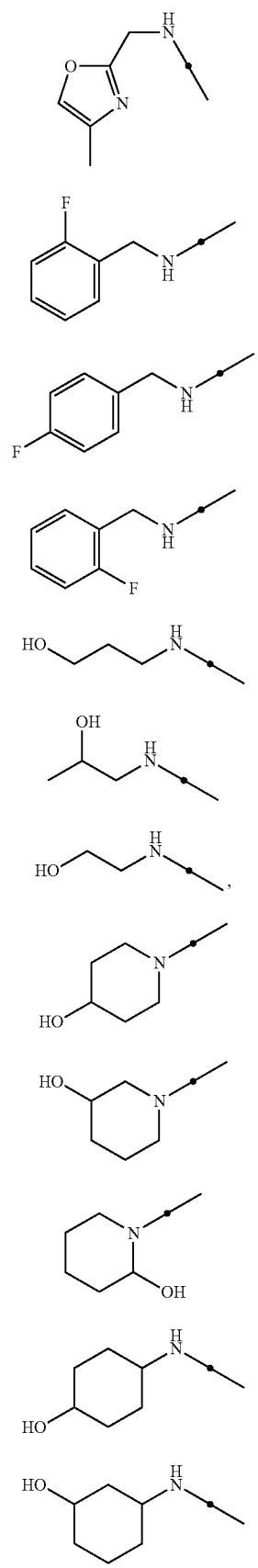
(a-81)
(a-82)
(a-83)
(a-84)
(a-85)
(a-86)
(a-87)
(a-88)
(a-89)
(a-90)
(a-91)
(a-92)
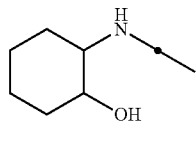
(a-93)
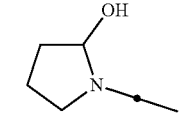
(a-94)
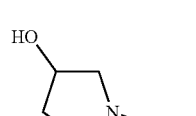
(a-95)
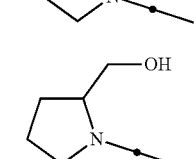
(a-96)
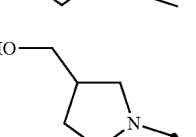
(a-97)
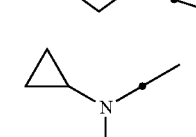
(a-98)
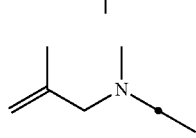
(a-99)
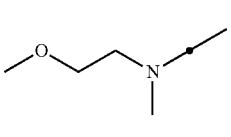
(a-100)
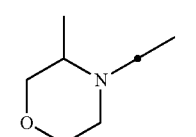
(a-101)
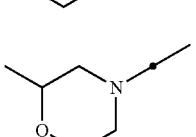
(a-102)
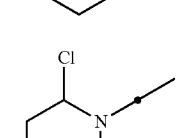
(a-103)
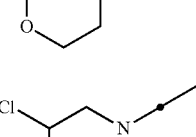
(a-104)

-continued (a-105) (a-106) (a-107) (a-108) (a-109) (a-110) (a-111) (a-112) (a-113) (a-114) (a-115) (a-116)

(a-117) (a-118) (a-119) (a-120) (a-121) (a-122) (a-123) (a-124) (a-125) (a-126) (a-127) (a-128)

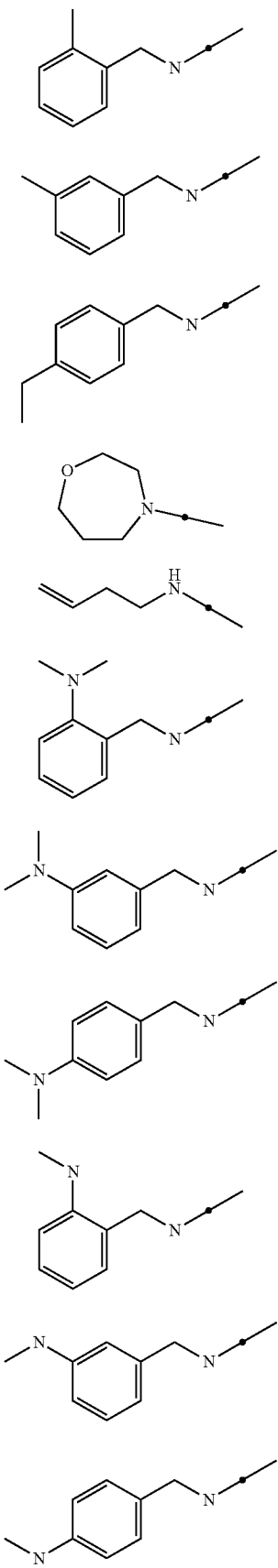
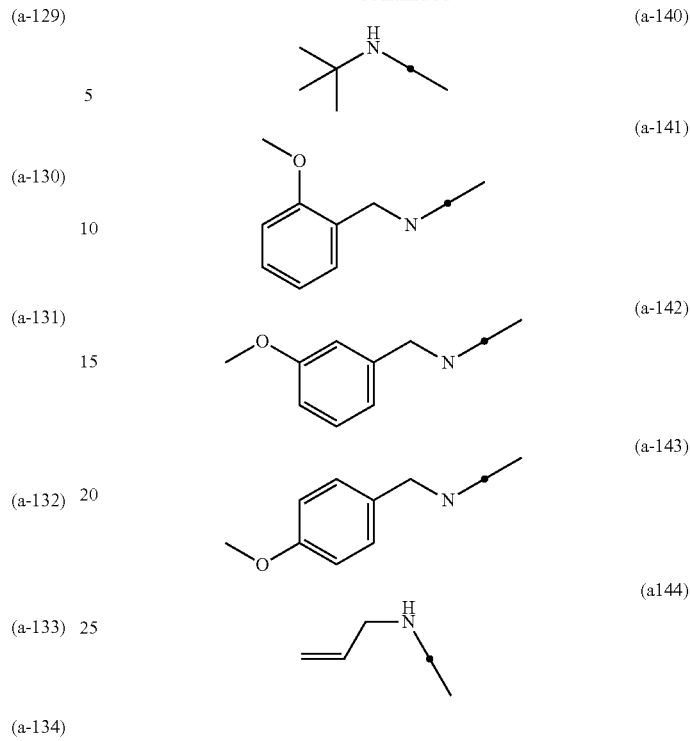

Suitably, in an embodiment of the invention and/or embodiments thereof —$NR^{A1}R^{A2}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), (a-131) and (a-144).

Suitably, in an embodiment of the invention and/or embodiments thereof —$NR^{A1}R^{A2}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), (a-128) and (a-144).

Suitably, in an embodiment of the invention and/or embodiments thereof —$NR^{A1}R^{A2}$ is selected from the group consisting of (a-1), (a-3), (a-5), (a-9), (a-20), (a-34), (a-35), (a-36), (a-42), (a-46), (a-55), (a-64), (a-65) and (a-144).

Suitably, in an embodiment of the invention and/or embodiments thereof —$NR^{A1}R^{A2}$ is selected from the group consisting of (a-1), (a-3), (a-5), (a-20), (a-34), (a-35), (a-36), (a-46), (a-55), (a-64), (a-65) and (a-144).

Suitably in an embodiment of the invention and/or embodiments thereof, when $R^{A1}$ is H then $R^{A2}$ is not H.

In a preferred embodiment A is selected from morpholine, $CH_2=CHCH_2NH$, $CH_3O(CH_2)_2NH$, benzylamine, cyclopropylamine and $CF_3CH_2NH$.

In embodiments, L is selected from the group consisting of $C_{1-6}$-alkyl, $C_{2-6}$-alkenyl, $C_{2-6}$-alkynyl, $C_{3-10}$-cycloalkyl, aryl, heterocyclyl, heteroaryl, $-(NR^{L3})_{0-1}-(CH_2)_{0-4}-NR^{L3}-(CH_2)_{0-4}-$, $-(NR^{L3})_{0-4}-(CR^{L1}R^{L2})_{0-4}-NR^{L3}-(CR^{L1}R^{L2})-$, $-(CR^{L1}R^{L2})_{0-4}-O-(CR^{L1}R^{L2})-$, $-(CH_2)_{0-4}-NR^{L3}-(CR^{L1}R^{L2})-C$ (=O)NH—(CH$_2$)$_{0-4}$—, —C(=O)—(CR$^{L1}$R$^{L2}$)NR$^{L3}$C(=O)—, —C(=O)NR$^{L3}$—, —NR$^{L3}$C(=O)—, NR$^{L3}$—C(=O)—NR$^{L3}$— wherein

R$^{L1}$, R$^{L2}$, R$^{L3}$, are independently selected from the group consisting of H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of

C$_{1-6}$-alkyl, C$_{2-6}$-alkenyl, C$_{2-6}$-alkynyl, C$_{3-10}$-cycloalkyl, —(NR$^{L3}$)$_{0-1}$—(CH$_2$)$_{0-4}$—NR$^{L3}$—(CH$_2$)$_{0-4}$—, (CR$^{L1}$R$^{L2}$)$_{0-4}$—NR$^{L3}$—(CR$^{L1}$R$^{L2}$)—, —(CR$^{L1}$R$^{L2}$)$_{0-4}$—O—(CR$^{L1}$R$^{L2}$)—, —(CH$_2$)$_{0-4}$—NR$^{L3}$—(CR$^{L1}$R$^{L2}$)—C(=O)NH—(CH$_2$)$_{0-4}$—, —C(=O)—(CR$^{L1}$R$^{L2}$)—NR$^{L3}$C(=O)—, —C(=O)NR$^{L3}$—, —NR$^{L3}$C(=O)—, —SO$_2$NR$^{L3}$—, NR$^{L3}$—C(=O)—NR$^{L3}$— wherein

R$^{L1}$, R$^{L2}$, R$^{L3}$, are independently selected from the group consisting of H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of

C$_{1-6}$-alkyl, C$_{2-6}$-alkenyl, C$_{2-6}$-alkynyl, C$_{3-10}$-cycloalkyl, —(NR$^{L3}$)$_{0-1}$—(CH$_2$)$_{0-4}$—NR$^{L3}$—(CH$_2$)$_{0-4}$—, —(NR$^{L3}$)$_{0-1}$—(CR$^{L1}$R$^{L2}$)$_{0-4}$—NR$^{L3}$—(CR$^{L1}$R$^{L2}$)—, —(CR$^{L1}$R$^{L2}$)$_{0-4}$—O—(CR$^{L1}$R$^{L2}$)—, —NR$^{L3}$—, —SO$_2$NR$^{L3}$—, wherein R$^{L1}$, R$^{L2}$, R$^{L3}$, are independently selected from the group consisting of H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of C$_{1-6}$-alkyl, C$_{2-6}$-alkenyl, C$_{2-6}$-alkynyl, C$_{3-10}$-cycloalkyl, wherein R$^{L3}$, is selected from the group consisting of H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl.

Suitably L is selected from the group consisting of C$_{1-6}$-alkyl, or C$_{2-6}$-alkenyl.

Suitably L is C$_{1-6}$-alkyl. Suitably L is —CH$_2$—, —CH$_2$CH$_2$—, —CH$_2$CH$_2$CH$_2$—, or —CH$_2$CH$_2$CH$_2$CH$_2$—. Suitably L is —CH$_2$—, —CH$_2$CH$_2$—, or —CH$_2$CH$_2$CH$_2$—. Suitably L is —CH$_2$—, or —CH$_2$CH$_2$—.

In some embodiments of the invention and/or embodiments thereof the compounds are compounds according to formula (VII)

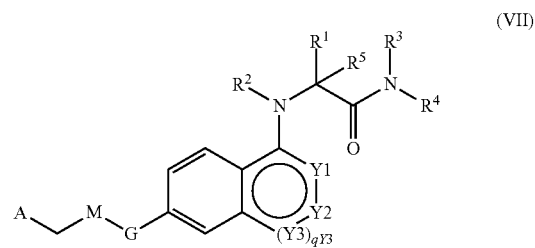

(VII)

or a stereoisomer, pharmaceutically acceptable salt, ester, solvate, or prodrug thereof, wherein A M, G, Y1; Y2; Y3, qY3, R$^1$, R$^2$, R$^3$, R$^4$, and R$^5$ are defined as in any of the embodiments described herein.

In some embodiments, M is selected from the group consisting of

C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—, wherein each cycloalkyl, aryl, heterocyclyl, or heteroaryl is optionally substituted with a substituent selected from the group consisting of C$_{1-6}$-alkyl, C$_{3-8}$-cycloalky, C$_{1-6}$-alkyloxy, NR$^{M2}$R$^{M3}$, carbonyl, —C(=O)—OR$^{M2}$, halo, halo-C$_{1-6}$-alkyl, C$_{1-6}$-alkyloxy-C$_1$-C$_6$, aryl, heteroaryl, C$_1$-C$_6$-alkyl substituted with aryl, cyano, hydroxy, —SR$^M$, —SO$_2$R$^{M4}$, —OSO$_2$R$^{M4}$, —SO$_2$NR$^{M2}$R$^{M3}$, —C(=O)NR$^{M2}$R$^{M3}$—, hydroxy-C$_{1-6}$-alkyl;

wherein R$^{M1}$ is selected from the group consisting of H, C$_{1-6}$-alkyl, halo, hydroxyl, and amino;

wherein R$^{M2}$, R$^{M3}$ are independently selected from the group consisting of H, and C$_{1-6}$-alkyl;

wherein R$^{M4}$ is selected from the group consisting of H, C$_{1-6}$-alkyl, and amino.

In some embodiments, M is selected from the group consisting of

C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—.

Suitably M is selected from the group consisting of aryl, heterocyclyl, heteroaryl, —C(R$^{M1}$)=C(R$^{M1}$)—C≡C—, —C(R$^{M1}$)=C(R$^{M1}$)—.

Suitably M is selected from the group consisting of aryl, heteroaryl, —C(R$^{M1}$)=C(R$^{M1}$)—C≡C—, —C(R$^{M1}$)=C(R$^{M1}$)—.

Suitably M is selected from the group consisting of aryl, and heteroaryl.

Suitably M is selected from the group consisting of phenyl, thiazolyl, pyridinyl, pyrimidinyl, thiophenyl, furanyl, pyrrolyl, imidazolyl, oxazolyl, pyrazinyl, pyranyl, thiopyranyl, oxazinyl, thiazynyl, —C(R$^{M1}$)=C(R$^{M1}$)—C≡C—, —C(R$^{M1}$)=C(R$^{M1}$)—.

Suitably M is selected from the group consisting of phenyl, thiazolyl, pyridinyl, pyrimidinyl, thiophenyl, furanyl, pyrrolyl, imidazolyl, oxazolyl, pyrazinyl, —C(R$^{M1}$)=C(R$^{M1}$)—C≡C—, —C(R$^{M1}$)=C(R$^{M1}$)—.

Suitably M is selected from the group consisting of phenyl, thiazolyl, pyridinyl, pyrimidinyl, thiophenyl, furanyl, —C(R$^{M1}$)=C(R$^{M1}$)—C≡C—, —C(R$^{M1}$)=C(R$^{M1}$)—.

Suitably M is selected from the group consisting of phenyl, thiazolyl, pyridinyl, pyrimidinyl, thiophenyl, furanyl, —C(H)=C(H)—C≡C—, —C(H)=C(H)—.

Suitably the cycloalkyl, aryl, heterocyclyl, or heteroaryl of M is optionally substituted with a substituent selected from the group consisting of $C_{1-6}$-alkyl, $C_{1-6}$-alkyloxy, $NR^{M2}R^{M3}$, carbonyl, —C(=O)—$OR^{M2}$, halo, halo-$C_{1-6}$-alkyl, $C_{1-6}$-alkyloxy-$C_1$-$C_6$, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, —C(=O)$NR^{M2}R^{M3}$—, hydroxy-$C_{1-6}$-alkyl.

Suitably the cycloalkyl, aryl, heterocyclyl, or heteroaryl of M is optionally substituted with a substituent selected from the group consisting of $C_{1-6}$-alkyl, $C_{1-6}$-alkyloxy, $NR^{M2}R^{M3}$, carbonyl, —C(=O)—$OR^{M2}$, halo, halo-$C_{1-6}$-alkyl, $C_{1-6}$-alkyloxy-$C_1$-$C_6$, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, —C(=O)$NR^{M2}R^{M3}$—, hydroxy-$C_{1-6}$-alkyl.

Suitably the cycloalkyl, aryl, heterocyclyl, or heteroaryl of M is optionally substituted with a substituent selected from the group consisting of $C_{1-6}$-alkyl, halo, amino, halo-$C_{1-6}$-alkyl, $C_{1-6}$-alkyloxy-$C_1$-$C_6$, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, hydroxy-$C_{1-6}$-alkyl.

Suitably the cycloalkyl, aryl, heterocyclyl, or heteroaryl of M is optionally substituted with a substituent selected from the group consisting of $C_{1-6}$-alkyl, halo, halo-$C_{1-6}$-alkyl, hydroxy-$C_{1-6}$-alkyl.

Suitably $R^{M1}$ is selected from the group consisting of H, $C_{1-6}$-alkyl, halo, hydroxyl, and amino. Suitably RM1 is selected from the group consisting of H, $C_{1-6}$-alkyl, and halo. Suitably $R^{M1}$ is selected from the group consisting of H, and $C_{1-6}$-alkyl.

Suitably, $R^{M2}$, $R^{M3}$ are independently selected from the group consisting of H, and $C_{1-6}$-alkyl.

Suitably $R^{M4}$ is selected from the group consisting of H, $C_{1-6}$-alkyl, and amino. Suitably $R^{M4}$ is selected from the group consisting of H, and $C_{1-6}$-alkyl.

Particular suitable groups of M are selected from the group consisting of

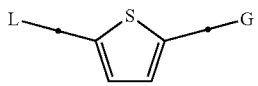 (m-1)

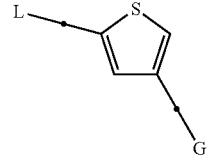 (m-2)

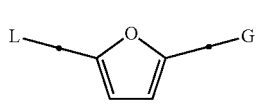 (m-3)

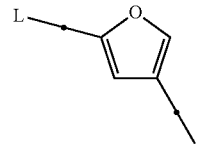 (m-4)

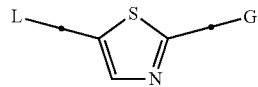 (m-5)

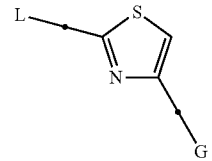 (m-6)

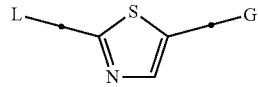 (m-7)

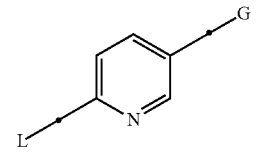 (m-8)

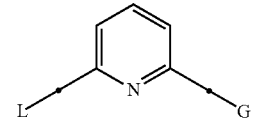 (m-9)

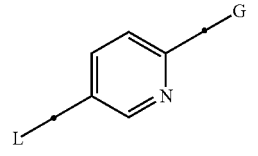 (m-10)

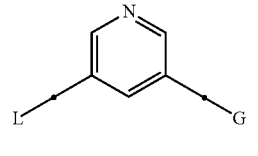 (m-11)

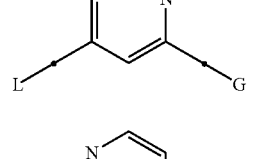 (m-12)

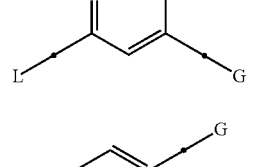 (m-13)

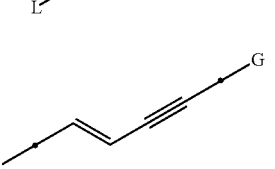 (m-14)

(m-15)

-continued

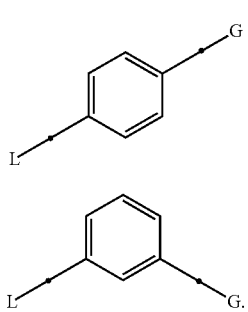

(m-16)

(m-17)

Particular suitable groups of M are selected from the group consisting of
(m-1), (m-3), (m-5), (m-8), (m-14), (m-15), (m-16), (m-17).

Particular suitable groups of M are selected from the group consisting of
(m-1), (m-8), (m-16).

In another embodiment of the invention and/or embodiments thereof G is selected from the group consisting of
—(C(R$^{G2}$R$^{G3}$)$_{0-4}$—O—(C(R$^{G2}$R$^{G3}$)$_{0-4}$—, —(C(R$^{G2}$R$^{G3}$)$_{0-4}$—S—(C(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—, —NR$^{G1}$C(=O)—, —C(=O)NR$^{G1}$—, —(C(R$^{G2}$R$^{G3}$)$_{0-4}$—NR$^{G1}$—C(R$^{G2}$R$^{G3}$)—C(=O)NR$^{G1}$—,
—CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—SO$_2$—, —S(=O)—, —S(=O)C(R$^{G2}$R$^{G3}$)—, —(C(R$^{G2}$R$^{G3}$)S(=O)—, —C(R$^{G2}$R$^{G3}$)—SO$_2$—, —SO$_2$C(R$^{G2}$R$^{G3}$)—;
wherein
R$^{G1}$ is H or C$_{1-6}$-alkyl
each R$^{G2}$, R$^{G3}$ is independently selected from the group consisting of
H, halogen atom, or C$_{1-6}$-alkyl.

In suitable embodiments, G is selected from the group consisting of —(C(R$^{G2}$R$^{G3}$)$_{0-4}$—O—(C(R$^{G2}$R$^{G3}$)$_{0-4}$—, —(C(R$^{G2}$R$^{G3}$)$_{0-4}$—S—(C(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—, —NR$^{G1}$C(=O)—, —C(=O)NR$^{G1}$—, —(C(R$^{G2}$R$^{G3}$)$_{0-4}$—NR$^{G1}$—C(R$^{G2}$R$^{G3}$)—C(=O)NR$^{G1}$—, —CR$^{G2}$=CR$^{G2}$—, —C≡C—, —C≡C—C≡C—, —C≡C—C(=O)—SO$_2$—, —S(=O)—, —S(=O)C(R$^{G2}$R$^{G3}$)—, —C(R$^{G2}$R$^{G3}$)S(=O)—, —C(R$^{G2}$R$^{G3}$)—SO$_2$—, —SO$_2$C(R$^{G2}$R$^{G3}$)—;
wherein
R$^{G1}$ is H or C$_{1-6}$-alkyl
each R$^{G2}$, R$^{G3}$ is independently selected from the group consisting of
H, halogen atom, or C$_{1-6}$-alkyl.

Suitably G is selected from the group consisting of CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—, wherein R$^{G2}$ is selected from the group consisting of H, halogen atom, or C$_{1-6}$-alkyl.

In suitable embodiments, G is selected from the group consisting of —C≡C—, —C≡C—C≡C—, —CR$^{G2}$=CR$^{G2}$—C≡C—, —C≡C—CR$^{G2}$=CR$^{G2}$, wherein R$^{G2}$ is selected from the group consisting of H, halogen atom, or C$_{1-6}$-alkyl.

In another suitable embodiments, G is selected from the group consisting of CR$^{G2}$=CR$^{G2}$—, —C≡C—, —C≡C—C≡C—, —C≡C—C(=O)—.
wherein
R$^{G2}$ is selected from the group consisting of
H, halogen atom, or C$_{1-6}$-alkyl.

In another suitable embodiments, G is selected from the group consisting of —C≡C—, —C≡C—C≡C—.

In another suitable embodiments, G is —C≡C—.

In some embodiments of the invention and/or embodiments thereof the compound is a compound according to formula (II)

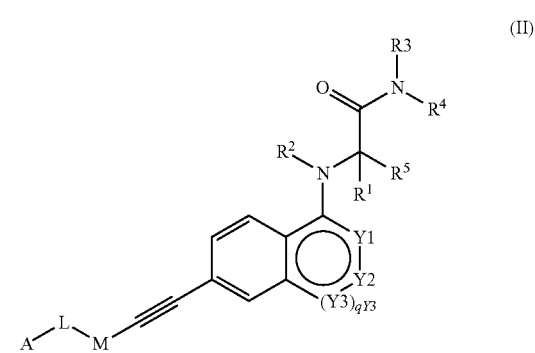

(II)

or a stereoisomer, pharmaceutically acceptable salt, ester, solvate, or prodrug thereof, wherein A, L, M, Y1, Y2, Y3 qY3, R$^1$, R$^2$, R$^3$, R$^4$, and R$^5$ are defined as in any of the embodiments described herein.

In some embodiments of the invention and/or embodiments thereof the compound is a compound according to formula (VIII)

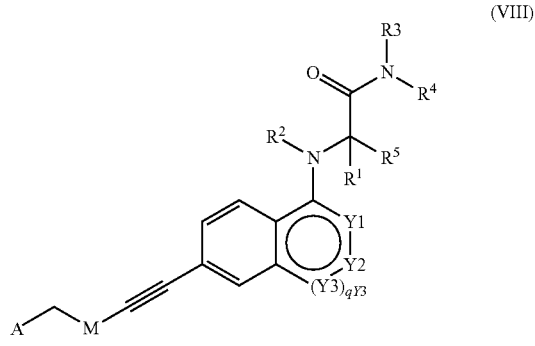

(VIII)

or a stereoisomer, pharmaceutically acceptable salt, ester, solvate, or prodrug thereof, wherein A, M Y1, Y2, Y3, qY3, R$^1$, R$^2$, R$^3$, R$^4$, and R$^5$ are defined as in any of the embodiments described herein.

In another embodiment of the invention and/or embodiments thereof, Y1, Y2 and Y3 and qY3 are defined as in the embodiment described above.

In a suitable embodiment Y1 is CR$^{10}$, N, O or S, wherein R$^{10}$ is selected from the group consisting of
H, C$_{1-6}$-alkyl, C$_{2-6}$-alkenyl, C$_{2-6}$-alkynyl, C$_{3-10}$-cycloalkyl, —OR$^8$, C(=O)OR$^8$, C(=O)R$^8$, aryl, heterocyclyl, heteroaryl, C$_1$-C$_6$-alkyl substituted with aryl, C$_1$-C$_6$-alkyl substituted with heteroaryl, and C$_1$-C$_6$-alkyl substituted with heterocyclyl;

wherein each alkyl, alkenyl, alkynyl, cycloalkyl, aryl, heterocyclyl, heteroaryl, is optionally substituted with a substituent selected from the group consisting of $C_{1-6}$-alkyl, $C_{3-8}$-cycloalky, $C_{1-6}$-alkyloxy, $NR^6R^7$, carbonyl, nitro, $C(=O)OR^8$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, and —$C(=O)NR^6R^7$; and In more suitable embodiments Y1 is $CR^{10}$ N, O, or S, wherein $R^{10}$ is H or $C_{1-6}$-alkyl. More preferably Y1 is $CR^{10}$ or N, wherein $R^{10}$ is H or $C_{1-6}$-alkyl. Even more preferably Y1 is $CR^{10}$ or N, wherein $R^{10}$ is H. In a particularly preferred embodiment Y1 is N.

In some embodiments of the invention and/or embodiments thereof the compound is a compound according to formula (IX)

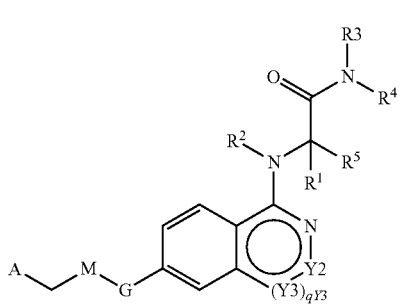

(IX)

or a stereoisomer, pharmaceutically acceptable salt, ester, solvate, or prodrug thereof, wherein A, M, G, Y2, Y3, qY3, $R^1$, $R^2$, $R^3$, $R^4$, and $R^5$ are defined as in any of the embodiments described herein.

In some embodiments of the invention and/or embodiments thereof the compound is a compound according to formula (X)

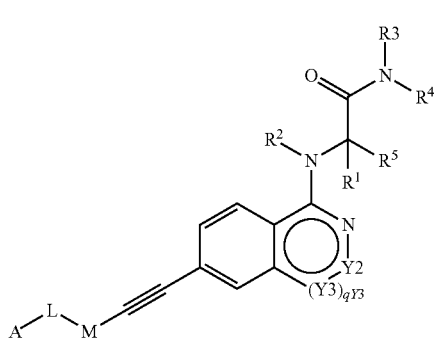

(X)

or a stereoisomer, pharmaceutically acceptable salt, solvate, or prodrug thereof, wherein A, L, M, Y2, Y3, qY3, $R^1$, $R^2$, $R^3$, $R^4$, and $R^5$ are defined as in any of the embodiments described herein.

In some embodiments Y2 is $CR^{10}$, N, O, or S, wherein $R^{10}$ is defined as in the embodiments described herein.

In some embodiment when qY3 is 0, Y2 is $CR^{10}$, N, O, or S, wherein $R^{10}$ is selected from the group consisting of H, $C_{1-6}$-alkyl, $OR^8$,
wherein each alkyl is optionally substituted with a substituent selected from the group consisting of $C_{1-6}$-alkyl, $NR^6R^7$, halogen, cyano, hydroxy, and —$C(=O)NR^6R^7$ In some embodiment, when qY3 is 0, Y2 is CH, N or S, preferably CH or S.

In some embodiments of the invention and/or embodiments thereof the compound is a compound according to formula (XI)

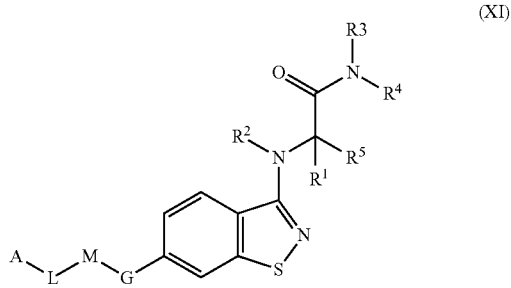

(XI)

or a stereoisomer, pharmaceutically acceptable salt, ester, solvate, or prodrug thereof, wherein A, L, M, G, $R^1$, $R^2$, $R^3$, $R^4$, and $R^5$ are defined as in any of the embodiments described herein and wherein qY3 is 0.

In somebody embodiment qY3 is 1.

In some embodiment when qY3 is 1, Y2 is $CR^{10}$, N, O, or S, wherein $R^{10}$ is selected from the group consisting of H, $C_{1-6}$-alkyl, $OR^8$,
wherein each alkyl is optionally substituted with a substituent selected from the group consisting of $C_{1-6}$-alkyl, $NR^6R^7$, halogen, cyano, hydroxy, and —$C(=O)NR^6R^7$.

In some embodiment, when qY3 is 1, Y2 is N or $CR^{10}$, wherein $R^{10}$ is selected from the group consisting of H, $C_{1-6}$-alkyl, $OR^8$,
wherein each alkyl is optionally substituted with a substituent selected from the group consisting of $C_{1-6}$-alkyl, $NR^6R^7$, halogen, cyano, hydroxy, and —$C(=O)NR^6R^7$, preferably CH or N.

In a particularly preferred embodiment, when qY3 is 1, Y2 is $CR^{10}$, especially CH.

In an alternative, particularly preferred embodiment, when qY3 is 1, Y2 is N.

In some embodiment Y3 is $CR^{10}$, N, O, or S, wherein $R^{10}$ is selected from the group consisting of
H, $C_{1-6}$-alkyl, $OR^8$,
wherein each alkyl is optionally substituted with a substituent selected from the group consisting of
$C_{1-6}$-alkyl, $NR^6R^7$, halogen, cyano, hydroxy, and —$C(=O)NR^6R^7$ In some embodiment, Y3 is N or $CR^{10}$, wherein $R^{10}$ is selected from the group consisting of
H, $C_{1-6}$-alkyl, $OR^8$,
wherein each alkyl is optionally substituted with a substituent selected from the group consisting of $C_{1-6}$-alkyl, $NR^6R^7$, halogen, cyano, hydroxy, and —$C(=O)NR^6R^7$, preferably CH or N.

In a particularly preferred embodiment, Y3 is $CR^{10}$, especially CH.

In an alternative, particularly preferred embodiment, Y3 is N.

In a particularly preferred embodiment, when qY3 is 1, Y2 is CH and Y3 is N.

In some embodiments of the invention and/or embodiments thereof the compound is a compound according to formula (XII)

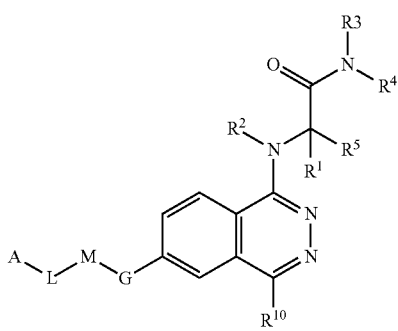

(XII)

or a stereoisomer, pharmaceutically acceptable salt, ester, solvate, or prodrug thereof, wherein A, L, M, G, R$^1$, R$^2$, R$^3$, R$^4$, R$^5$, and R$^{10}$ are defined as in any of the embodiments described herein.

In some embodiments of the invention and/or embodiments thereof the compound is a compound according to formula (XIII)

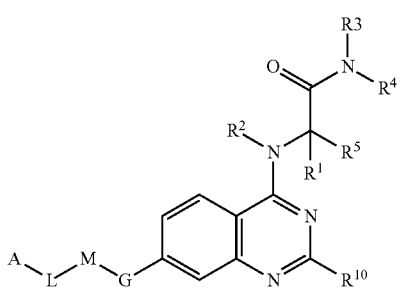

(XIII)

or a stereoisomer, pharmaceutically acceptable salt, ester, solvate, or prodrug thereof, wherein A, L, M, G, R$^1$, R$^2$, R$^3$, R$^4$, R$^5$, and R$^{10}$ are defined as in any of the embodiments described herein.

In suitable embodiments of the invention and/or embodiments thereof R$^5$ is selected from the group consisting of H, and C$_{1-6}$-alkyl. Suitably R$^5$ is H.

In some embodiments of the invention and/or embodiments thereof the compounds are compounds according to formula (XIV)

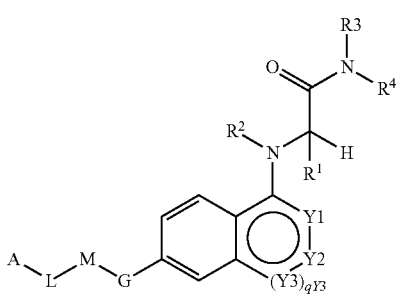

(XIV)

or a stereoisomer, pharmaceutically acceptable salt, ester, solvate, or prodrug thereof, wherein A, L, M, G, Y1, Y2, Y3, qY3, R$^1$, R$^2$, R$^3$, and R$^4$ are defined as in any of the embodiments described herein.

In embodiments of the invention and/or embodiments thereof R$^1$ is defined as described herein.

In some embodiments of the invention and/or embodiments thereof the compounds are compounds according to formula (XV)

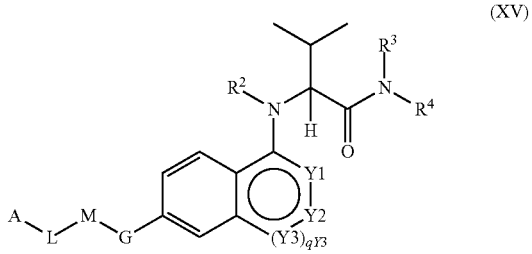

(XV)

or a stereoisomer, pharmaceutically acceptable salt, ester, solvate, or prodrug thereof, wherein A, L, M, G, Y1, Y2, Y3, qY3, R$^2$, R$^3$, and R$^4$ are defined as in any of the embodiments described herein.

In some embodiments of the invention and/or embodiments thereof the compounds are compounds according to formula (XVI)

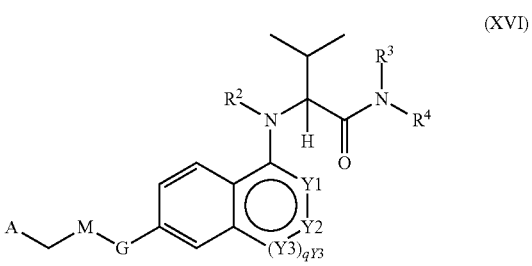

(XVI)

or a stereoisomer, pharmaceutically acceptable salt, ester, solvate, or prodrug thereof, wherein A, M, G, Y1, Y2, Y3, qY3, R$^2$, R$^3$, and R$^4$ are defined as in any of the embodiments described herein.

In some embodiments of the invention and/or embodiments thereof the compounds are compounds according to formula (XVII)

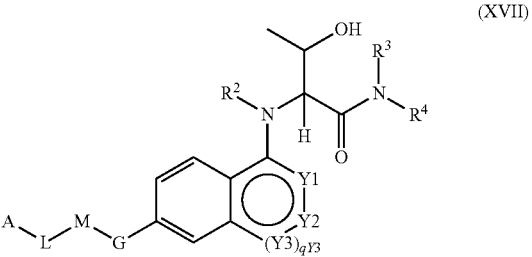

(XVII)

or a stereoisomer, pharmaceutically acceptable salt, ester, solvate, or prodrug thereof, wherein A, L, M, G, Y1, Y2, Y3, qY3, R$^2$, R$^3$, and R$^4$ are defined as in any of the embodiments described herein.

In some embodiments of the invention and/or embodiments thereof the compounds are compounds according to formula (XVIII)

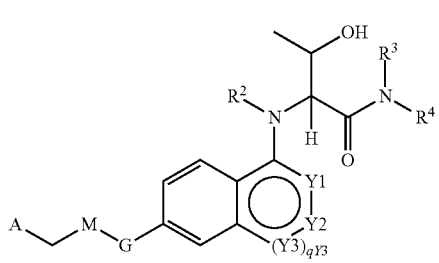

(XVIII)

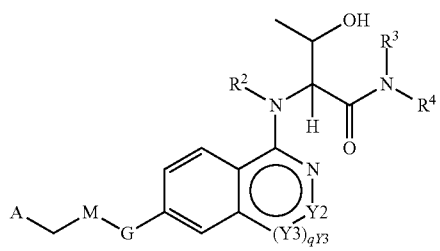

(XXI)

or a stereoisomer, pharmaceutically acceptable salt, ester, solvate, or prodrug thereof, wherein A, M, G, Y1, Y2, Y3 qY3, $R^2$, $R^3$, and $R^4$, are defined as in any of the embodiments described herein.

In some embodiments of the invention and/or embodiments thereof the compounds are compounds according to formula (XIX)

or a stereoisomer, pharmaceutically acceptable salt, ester, solvate, or prodrug thereof, wherein A, M, G, Y2, Y3; qY3, $R^2$, $R^3$, and $R^4$, are defined as in any of the embodiments described herein.

In some embodiments of the invention and/or embodiments thereof the compounds are compounds according to formula (XXII)

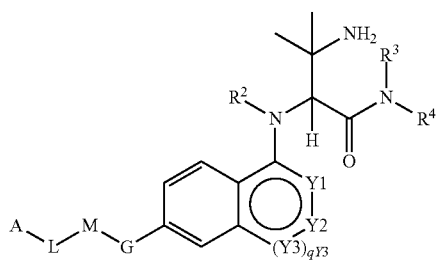

(XIX)

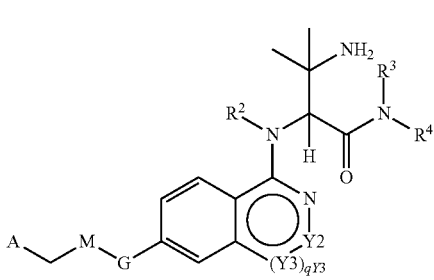

(XXII)

or a stereoisomer, pharmaceutically acceptable salt, ester, solvate, or prodrug thereof, wherein A, L, M, G, Y1, Y2, Y3, qY3 $R^2$, $R^3$, and $R^4$ are defined as in any of the embodiments described herein.

In some embodiments of the invention and/or embodiments thereof the compounds are compounds according to formula (XX)

or a stereoisomer, pharmaceutically acceptable salt, ester, solvate, or prodrug thereof, wherein A, M, G, Y2, Y3, qY3, $R^2$, $R^3$, and $R^4$, are defined as in any of the embodiments described herein.

In some embodiments of the invention and/or embodiments thereof the compounds are compounds according to formula (XXIII)

(XX)

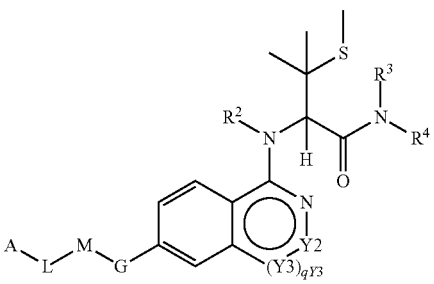

(XXIII)

or a stereoisomer, pharmaceutically acceptable salt, ester, solvate, or prodrug thereof, wherein A, M, G, Y1, Y2, Y3; qY3, $R^2$, $R^3$, and $R^4$, are defined as in any of the embodiments described herein.

In some embodiments of the invention and/or embodiments thereof the compounds are compounds according to formula (XXI)

or a stereoisomer, pharmaceutically acceptable salt, ester, solvate, or prodrug thereof, wherein A L, M, G, Y2, Y3, qY3, $R^2$, $R^3$, and $R^4$ are defined as in any of the embodiments described herein.

In some embodiments of the invention and/or embodiments thereof the compounds are compounds according to formula (XXIV)

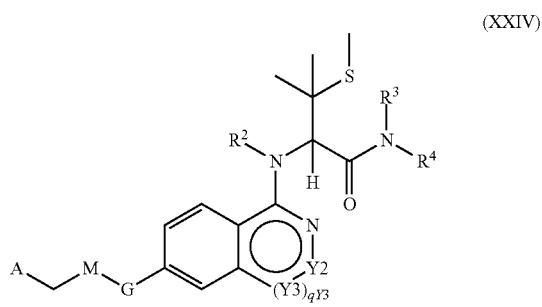

(XXIV)

or a stereoisomer, pharmaceutically acceptable salt, ester, solvate, or prodrug thereof, wherein A, M, G, Y2, Y3, qY3, R², R³, and R⁴, are defined as in any of the embodiments described herein.

In some embodiments of the invention and/or embodiments thereof the compounds are compounds according to formula (XXV)

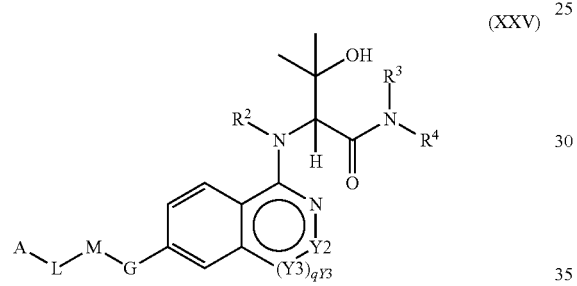

(XXV)

or a stereoisomer, pharmaceutically acceptable salt, ester, solvate, or prodrug thereof, wherein L, M, G, Y2, Y3, qY3, R², R³, and R⁴ are defined as in any of the embodiments described herein.

In some embodiments of the invention and/or embodiments thereof the compounds are compounds according to formula (XXVI)

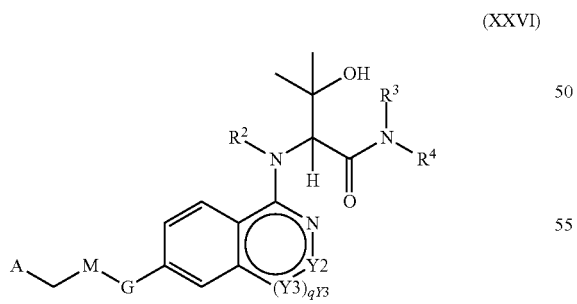

(XXVI)

or a stereoisomer, pharmaceutically acceptable salt, ester, solvate, or prodrug thereof, wherein A L, M, G, Y2, Y3, qY3, R², R³, and R⁴ are defined as in any of the embodiments described herein.

In some embodiments of the invention and/or embodiments thereof the compounds are compounds according to formula (XXVII)

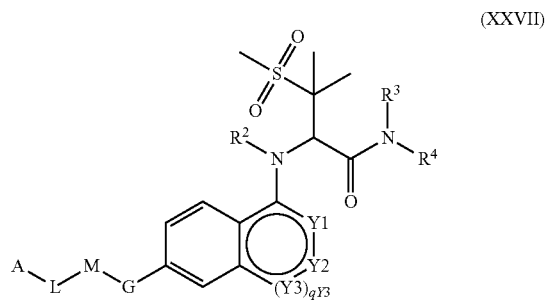

(XXVII)

or a stereoisomer, pharmaceutically acceptable salt, ester, solvate, or prodrug thereof, wherein A, L, M, G, Y1, Y2, Y3, qY3, R², R³ and R⁴ are defined as in any of the embodiments described herein.

In some embodiments of the invention and/or embodiments thereof the compounds are compounds according to formula (XXVIII)

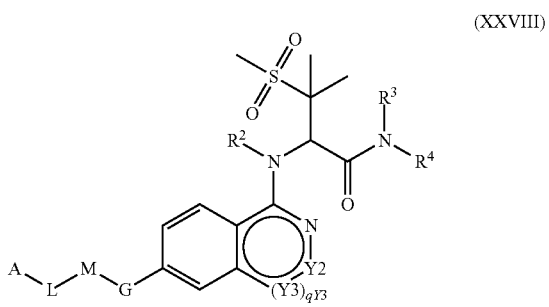

(XXVIII)

or a stereoisomer, pharmaceutically acceptable salt, ester, solvate, or prodrug thereof, wherein A, L, M, G, Y2, Y3, qY3, R², R³, and R⁴, are defined as in any of the embodiments described herein.

In some embodiments of the invention and/or embodiments thereof the compounds are compounds according to formula (XXIX)

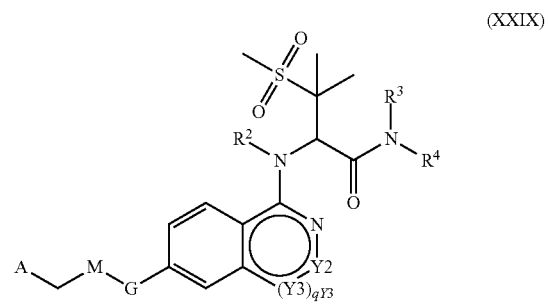

(XXIX)

or a stereoisomer, pharmaceutically acceptable salt, ester, solvate, or prodrug thereof, wherein M wherein A, M, G, Y2, Y3, qY3, R², R³, and R⁴, are defined as in any of the embodiments described herein.

In some embodiments of the invention and/or embodiments thereof the compounds are compounds according to formula (XXX)

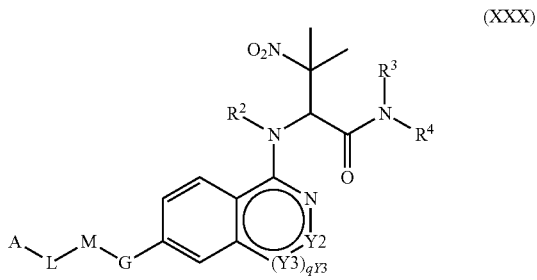

(XXX)

or a stereoisomer, pharmaceutically acceptable salt, solvate, or prodrug thereof, wherein A, L, M, G, Y1, Y2, Y3, qY3, $R^2$, $R^3$, and $R^4$, are defined as in any of the embodiments described herein.

In some embodiments of the invention and/or embodiments thereof the compounds are compounds according to formula (XXXI)

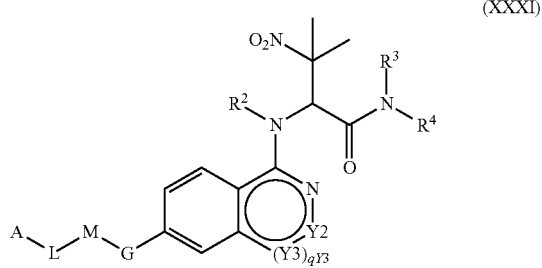

(XXXI)

or a stereoisomer, pharmaceutically acceptable salt, ester, solvate, or prodrug thereof, wherein A L, M, G, Y2, Y3, qY3, $R^2$, $R^3$, and $R^4$ are defined as in any of the embodiments described herein.

In some embodiments of the invention and/or embodiments thereof the compounds are compounds according to formula (XXXII)

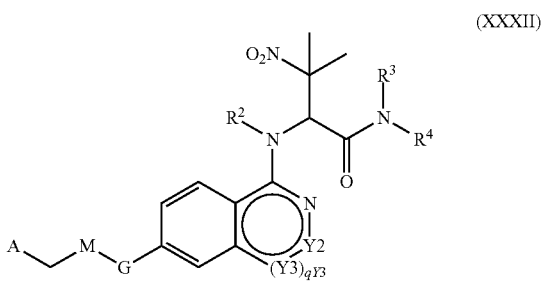

(XXXII)

or a stereoisomer, pharmaceutically acceptable salt, ester, solvate, or prodrug thereof, wherein A, M, G, Y2, Y3, qY3, $R^2$, $R^3$, and $R^4$ are defined as in any of the embodiments described herein.

In some embodiments of the invention and/or embodiments thereof the compounds are compounds according to formula (XXXIII)

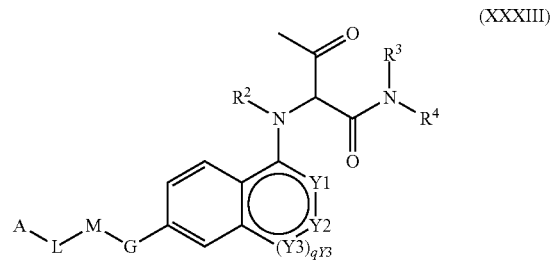

(XXXIII)

or a stereoisomer, pharmaceutically acceptable salt, ester, solvate, or prodrug thereof, wherein A, L, M, G, Y1, Y2, Y3, qY3, $R^2$, $R^3$, and $R^4$ are defined as in any of the embodiments described herein.

In some embodiments of the invention and/or embodiments thereof the compounds are compounds according to formula (XXXIV)

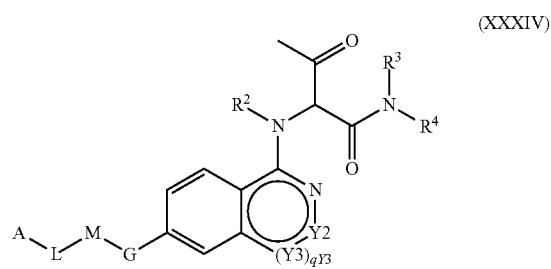

(XXXIV)

or a stereoisomer, pharmaceutically acceptable salt, ester, solvate, or prodrug thereof, wherein A L, M, G, Y2, Y3, qY3, $R^2$, $R^3$, and $R^4$ are defined as in any of the embodiments described herein.

In some embodiments of the invention and/or embodiments thereof the compounds are compounds according to formula (XXXV)

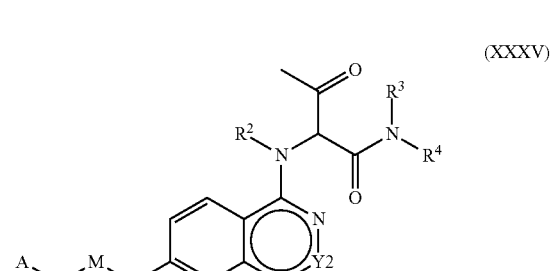

(XXXV)

or a stereoisomer, pharmaceutically acceptable salt, ester, solvate, or prodrug thereof, wherein A, M, G, Y2, Y3, qY3, $R^2$, $R^3$, and $R^4$ are defined as in any of the embodiments described herein.

In some embodiments of the invention and/or embodiments thereof the compounds are compounds according to formula (XXXVI)

(XXXVI)

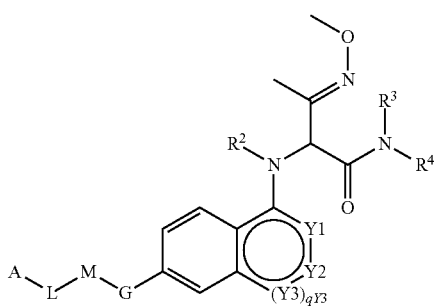

or a stereoisomer, pharmaceutically acceptable salt, ester, solvate, or prodrug thereof, wherein A, L, M, G, Y1, Y2, Y3, qY3, R², R³, and R⁴ are defined as in any of the embodiments described herein.

In some embodiments of the invention and/or embodiments thereof the compounds are compounds according to formula (XXXVII)

(XXXVII)

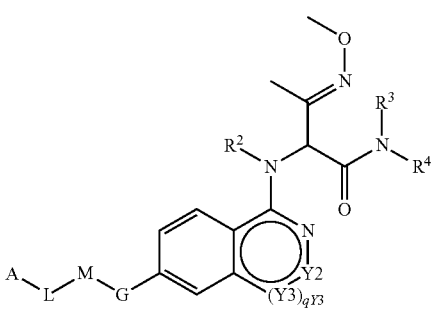

or a stereoisomer, pharmaceutically acceptable salt, ester, solvate, or prodrug thereof, wherein A L, M, G, Y2, Y3, qY3, R², R³, and R⁴ are defined as in any of the embodiments described herein.

In some embodiments of the invention and/or embodiments thereof the compounds are compounds according to formula (XXXVIII)

(XXXVIII)

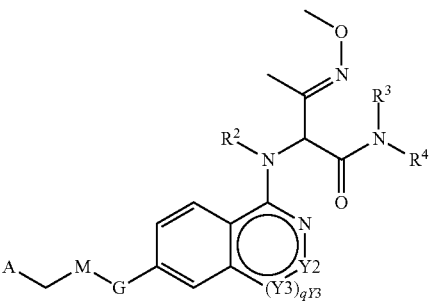

or a stereoisomer, pharmaceutically acceptable salt, ester, solvate, or prodrug thereof, wherein A L, M, G, Y2, Y3, qY3, R², R³, and R⁴ are defined as in any of the embodiments described herein.

In embodiments of the invention and/or embodiments thereof $R^2$, $R^3$ is independently selected from the group consisting of H, substituted $C_{1-6}$-alkyl, or un-substituted $C_{1-6}$-alkyl;

wherein the substituents on the substituted $C_{1-6}$-alkyl may be selected from the group consisting of halogen, hydroxyl, alkoxy, aryloxy, ester, thiol, $C_{1-6}$-alkyl, carbonyl, —SR⁸, —SO₂R⁸, —SO₂NR⁶R⁷, —C(=O) NR⁶R⁷, cyano, —NR⁶R⁷, —C(=O)—OR⁸, aryl, heteroaryl, heterocycle, $C_{3-8}$-cycloalkyl.

Suitably $R^2$, $R^3$ is independently selected from the group consisting of H, substituted $C_{1-6}$-alkyl, or un-substituted $C_{1-6}$-alkyl. Suitably $R^2$ and $R^3$ are H.

In some embodiment, the substituents on the substituted $C_{1-6}$-alkyl of $R^2$ and/or $R^3$ may be selected from the group consisting of hydroxyl, alkoxy, aryloxy, ester, thiol, $C_{1-6}$-alkyl, carbonyl, —SR⁸, —SO₂R⁸, —SO₂NR⁶R⁷, —C(=O) NR⁶R⁷, cyano, —NR⁶R⁷, —C(=O)—OR⁸, aryl, heteroaryl, heterocycle, $C_{3-8}$-cycloalkyl.

In some embodiment, the substituents on the substituted $C_{1-6}$-alkyl of $R^2$ and/or $R^3$ may be selected from the group consisting of hydroxyl, $C_{1-6}$-alkyl, carbonyl, —SR⁸, —SO₂NR⁶R⁷, —SO₂R⁸, —C(=O)NR⁶R⁷, cyano, —NR⁶R⁷, —C(=O)—OR⁸.

$R^6$ and $R^7$ are independently selected from the group consisting of H, and $C_{1-6}$-alkyl.

$R^8$ is selected from the group consisting of H, $C_{1-6}$-alkyl.

In some embodiment, the substituents on the substituted $C_{1-6}$-alkyl of $R^2$ and/or $R^3$ may be selected from the group consisting of hydroxyl, $C_{1-6}$-alkyl, —NR⁶R⁷.

In embodiments of the invention and/or embodiments thereof $R^4$ is selected from the group consisting of H, $C_{1-6}$-alkyl, $C_{2-6}$-alkenyl, $C_{2-6}$-alkynyl, $C_{3-10}$-cycloalkyl, C(=O)OR⁸, C(=O)R⁸, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl wherein each alkyl, alkenyl, alkynyl, cycloalkyl, aryl, heterocyclyl, heteroaryl, is optionally substituted with a substituent selected from the group consisting of $C_{1-6}$-alkyl, $C_{3-8}$-cycloalky, $C_{1-6}$-alkyloxy, NR⁶R⁷, carbonyl, nitro, C(=O)OR⁸, halogen, halo-$C_{1-6}$-alkyl, $C_{1-6}$-alkyloxy-$C_1$-$C_6$, cyano, hydroxy, SR⁸, —SO₂R⁸, —SO₂NR⁶R⁷, —C(=O)NR⁶R⁷.

In embodiments of the invention and/or embodiments thereof $R^4$ is selected from the group consisting of H, $C_{1-6}$-alkyl, $C_{2-6}$-alkenyl, $C_{2-6}$-alkynyl, C(=O)OR⁸, C(=O)R⁸, $C_1$-$C_6$-alkyl substituted with aryl, $C_1$-$C_6$-alkyl substituted with heteroaryl, $C_1$-$C_6$-alkyl substituted with heterocyclyl.

In embodiments of the invention and/or embodiments thereof $R^4$ is selected from the group consisting of H, $C_{1-6}$-alkyl, OR⁸, C(=O)OR⁸, C(=O)R⁸.

In embodiments of the invention and/or embodiments thereof $R^4$ is selected from the group consisting of H, —OR⁸. Suitably $R^4$ is OR⁸, more suitably $R^4$ is OH.

In some embodiments of the invention and/or embodiments thereof the compounds are compounds according to formula (XXXIX)

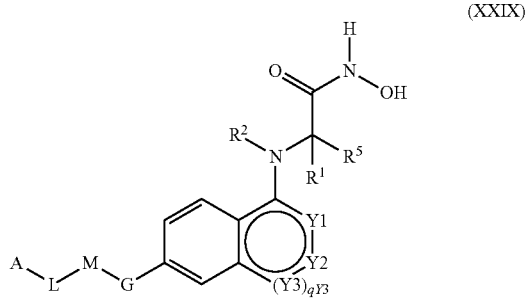

(XXIX)

or a stereoisomer, pharmaceutically acceptable salt, solvate, or prodrug thereof, wherein A L, M, G, Y1, Y2, Y3 qY3, $R^1$ $R^2$, and $R^5$ are defined as in any of the embodiments described herein.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $C_{3-8}$-cycloalky, $C_{1-6}$-alkyloxy, $NR^6R^7$, carbonyl, nitro, $C(=O)OR^8$, halogen, halo-$C_{1-6}$-alkyl, $C_{1-6}$-alkyloxy-$C_1$-$C_6$, cyano, hydroxy, —$SR^8$, —$SO_2R^8$, —$SO_2NR^6R^7$, —$C(=O)NR^6R^7$.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $C_{3-8}$-cycloalky, $NR^6R^7$, carbonyl, nitro, halogen, halo-$C_{1-6}$-alkyl, $C_{1-6}$-alkyloxy-$C_1$-$C_6$, cyano, hydroxy.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $NR^6R^7$, halogen, cyano, hydroxy.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $NR^6R^7$, halogen.

In embodiments of the invention and/or embodiments thereof $R^8$ is selected from the group consisting of H, $C_{1-6}$-alkyl. Suitably $R^8$ is H. Suitable $R^8$ is $C_{1-6}$-alkyl.

In embodiments of the invention and/or embodiments thereof $R^9$, $R^{10}$ as defined above.

In some embodiments of the invention and/or embodiments thereof the compounds are compounds according to formula XL

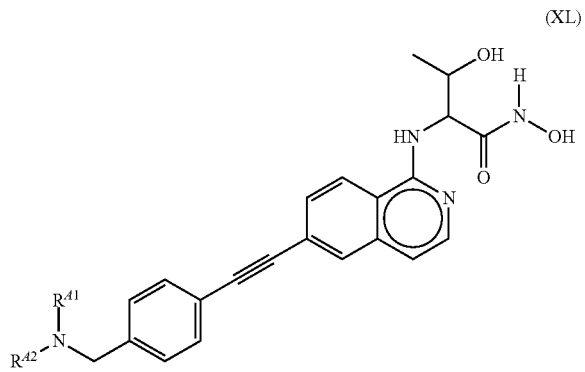

(XL)

or a stereoisomer, pharmaceutically acceptable salt, ester, solvate, or prodrug thereof, wherein $R^{41}$ and $R^{42}$ are defined as in any of the embodiments described herein.

In some embodiments of the invention and/or embodiments thereof the compounds are compounds according to formula (XLI)

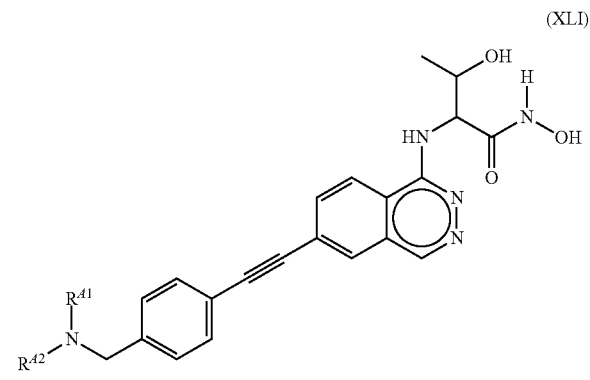

(XLI)

or a stereoisomer, pharmaceutically acceptable salt, ester, solvate, or prodrug thereof, wherein $R^{41}$ and $R^{42}$ are defined as in any of the embodiments described herein.

In some embodiments of the invention the compounds are compounds according to formula (XLII)

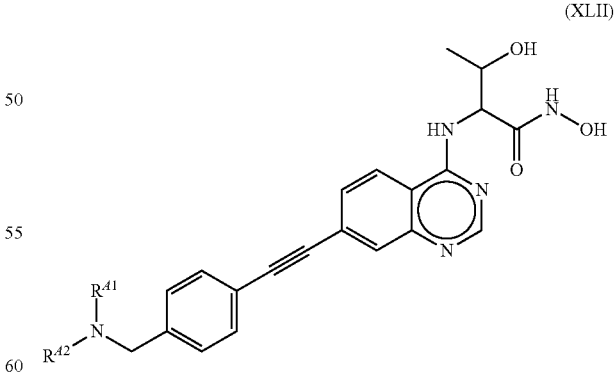

(XLII)

or a stereoisomer, pharmaceutically acceptable salt, ester, solvate, or prodrug thereof, wherein $R^{41}$ and $R^{42}$ are defined as in any of the embodiments described herein.

In some embodiments of the invention and/or embodiments thereof the compounds are compounds according to formula (XLIII)

(XLIII)

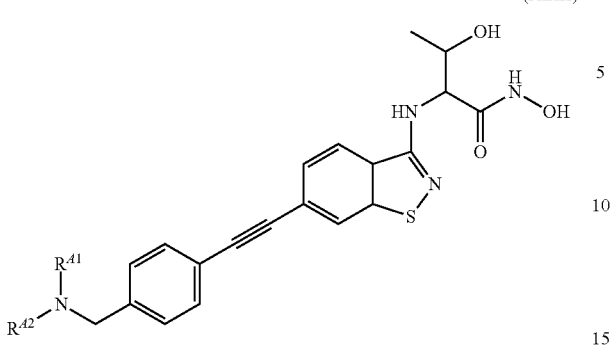

or a stereoisomer, pharmaceutically acceptable salt, ester, solvate, or prodrug thereof, wherein $R^{41}$ and $R^{42}$ are defined as in any of the embodiments described herein.

In some embodiments of the invention and/or embodiments thereof the compounds are compounds according to formula (XLIV)

(XLIV)

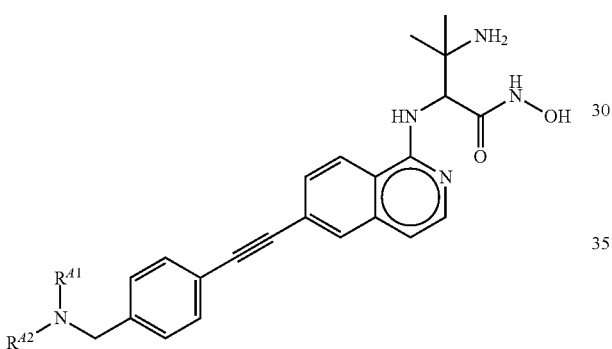

or a stereoisomer, pharmaceutically acceptable salt, ester, solvate, or prodrug thereof, wherein $R^{41}$ and $R^{42}$ are defined as in any of the embodiments described herein.

In some embodiments of the invention and/or embodiments thereof the compounds are compounds according to formula (XLV)

(XLV)

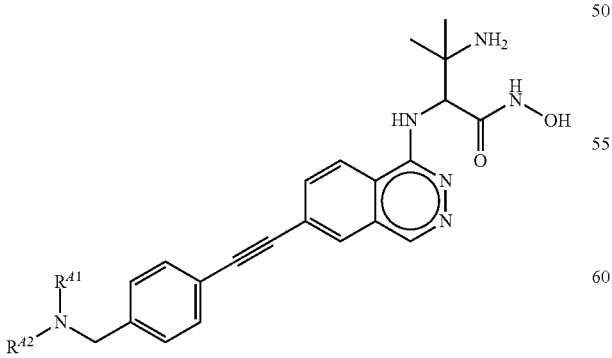

or a stereoisomer, pharmaceutically acceptable salt, ester, solvate, or prodrug thereof, wherein $R^{41}$ and $R^{42}$ are defined as in any of the embodiments described herein.

In some embodiments of the invention the compounds are compounds according to formula (XLVI)

(XLVI)

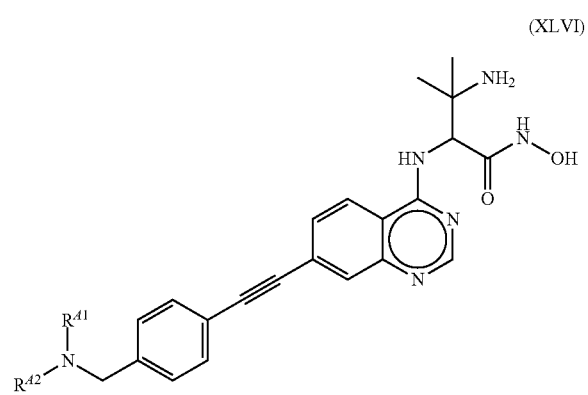

or a stereoisomer, pharmaceutically acceptable salt, ester, solvate, or prodrug thereof, wherein $R^{41}$ and $R^{42}$ are defined as in any of the embodiments described herein.

In some embodiments of the invention and/or embodiments thereof the compounds are compounds according to formula (XLVII)

(XLVII)

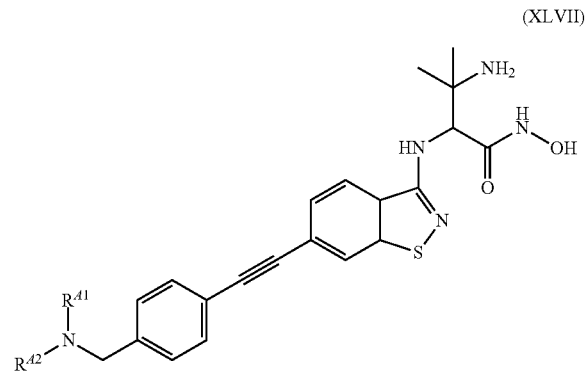

or a stereoisomer, pharmaceutically acceptable salt, ester, solvate, or prodrug thereof, wherein $R^{41}$ and $R^{42}$ are defined as in any of the embodiments described herein.

In some embodiments of the invention and/or embodiments thereof the compounds are compounds according to formula (XLVIII)

(XLVIII)

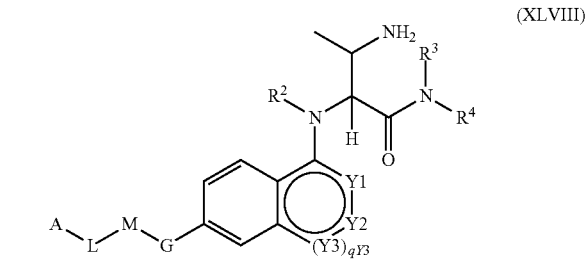

or a stereoisomer, pharmaceutically acceptable salt, ester, solvate, or prodrug thereof, wherein A, L, M, G, Y1, Y2, Y3, qY3 $R^2$, $R^3$, and $R^4$ are defined as in any of the embodiments described herein.

In some embodiments of the invention and/or embodiments thereof the compounds are compounds according to formula (XLIX)

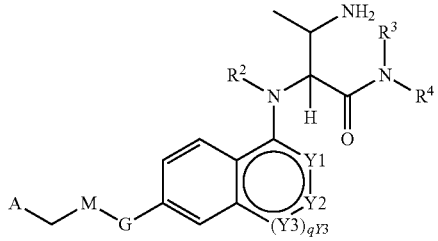

(XLIX)

or a stereoisomer, pharmaceutically acceptable salt, ester, solvate, or prodrug thereof, wherein A, M, G, Y1, Y2, Y3, qY3 $R^2$, $R^3$, and $R^4$ are defined as in any of the embodiments described herein.

In some embodiments of the invention and/or embodiments thereof the compounds are compounds according to formula (L)

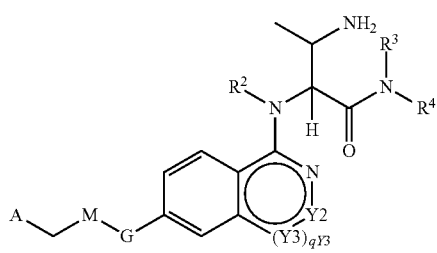

(L)

or a stereoisomer, pharmaceutically acceptable salt, ester, solvate, or prodrug thereof, wherein A, M, G, Y2, Y3, qY3 $R^2$, $R^3$, and $R^4$ are defined as in any of the embodiments described herein.

In some embodiments of the invention and/or embodiments thereof the compounds are compounds according to formula (LI)

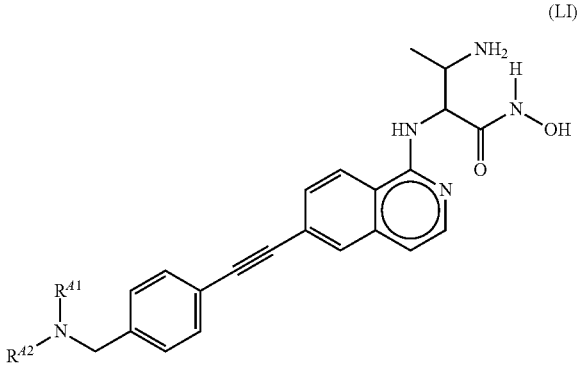

(LI)

or a stereoisomer, pharmaceutically acceptable salt, ester, solvate, or prodrug thereof, wherein $R^{41}$, $R^{42}$, are defined as in any of the embodiments described herein.

In some embodiments of the invention and/or embodiments thereof the compounds are compounds according to formula (LII)

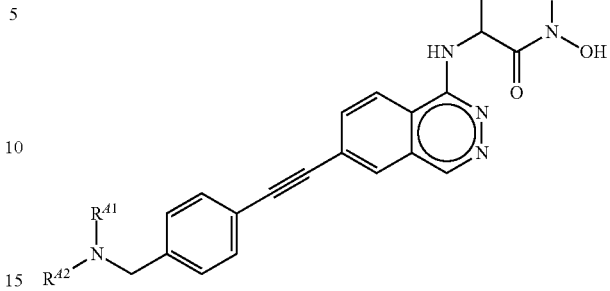

(LII)

or a stereoisomer, pharmaceutically acceptable salt, ester, solvate, or prodrug thereof, wherein $R^{41}$, $R^{42}$, are defined as in any of the embodiments described herein.

The invention is also directed to method for treating an animal with an infection by bacteria comprising administering to the subject in need thereof an effective amount of a compound of the present invention and/or embodiments thereof with a pharmaceutically acceptable carrier, wherein the bacteria are at least one of the bacteria selected from the group *Mannheimia haemolytica* and *Histophilus somni*. Suitably the subject is a mammal and in some embodiments, a ruminant or swine.

Further the invention is directed to a compound according to the present invention and/or embodiments thereof with a pharmaceutically acceptable carrier for use in the treatment of a infection by a bacteria in a subject, wherein the bacteria are at least one of the bacteria selected from the group *Mannheimia haemolytica* and *Histophilus somni*. Suitably the subject is a mammal and in some embodiments, a ruminant or swine.

The invention provides further a pharmaceutical composition comprising an effective amount of a compound according to the invention and/or embodiments thereof with a pharmaceutically acceptable carrier thereof.

Suitably the compound of the present invention and/or embodiments thereof, is co-administered with other therapeutic agents that are selected for their particular usefulness against the condition that is being treated.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The compound of the present invention and/or embodiments thereof may also be used in the treatment of Bovine Respiratory Disease and/or Swine Respiratory disease.

Pharmaceutical Compositions

Pharmaceutical compositions of the present invention and/or embodiments thereof comprise a therapeutically effective amount of a compound of the present invention and/or embodiments thereof formulated together with one or more pharmaceutically acceptable carriers.

As used herein, the term "pharmaceutically acceptable carrier" means a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringers solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention and/or embodiments thereof can be administered to animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

The term "pharmaceutically acceptable salt" includes a salt with an inorganic base, organic base, inorganic acid, organic acid, or basic or acidic amino acid.

Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt. In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as C1-C6-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

As salts of basic amino acids, the instant invention includes, for example, arginine, lysine and ornithine. Acidic amino acids include, for example, aspartic acid and glutamic acid.

The term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "antibacterial agent" refers to agents synthesized or modified in the laboratory that have either bactericidal or bacteriostatic activity. An "active" agent in this context will inhibit the growth of P. aeruginosa and other gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly (anhydrides). Depot injectable formulations may also be prepared by entrapping the drug in liposomes or microemulsions that are compatible with body tissues.

Compositions for rectal or vaginal administration can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e. g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli.

Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 pm.

Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 um. Predominantly in this application means that at least 70% but preferably more than 90% of all generated aerosol particles are 1 to 5 pm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances.

Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin.

The rate can be controlled by either providing a rate controlling membrane or by dispersing the compound in a polymer matrix or gel.

According to the treatment by the compounds of the present invention and/or embodiments thereof, bacterial infections are treated or prevented in an animal by administering to the animal a therapeutically effective amount of a compound of the invention, in such amounts and for such time as is necessary to achieve the desired result.

By a "therapeutically effective amount" of a compound of the invention and/or embodiments thereof is meant a sufficient amount of the compound to treat bacterial infections, at a reasonable benefit/risk ratio applicable to any medical treatment. It will be understood, however, that the total daily usage of the compounds and compositions of the present invention will be decided by the attending physician or veterinary doctor within the scope of sound medical judgment. The specific therapeutically effective dose level for any particular animal will depend upon a variety of factors including the disorder being treated and the severity of the disorder; the activity of the specific compound employed; the specific composition employed; the age, body weight, general health, sex and diet of the animal; the time of administration, route of administration, and rate of excretion of the specific compound employed; the duration of the treatment; drugs used in combination or coincidental with the specific compound employed; and like factors well known in the medical arts.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

A "kit" as used in the instant application includes a container for containing the pharmaceutical compositions and may also include divided containers such as a divided bottle or a divided foil packet.

The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule.

The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Compositions of the present compounds may also be used in combination with other known antibacterial agents of similar spectrum to (1) synergistically enhance treatment of severe Gram-negative infections covered by the spectrum of this compound or (2) add coverage in severe infections in which multiple organisms are suspected in which another agent of a different spectrum may be required in addition to this compound. Potential agents include members of the aminoglycosides, penicillins, cephalosporins, fluoroquinolones, macrolides, glycopeptides, lipopeptides and oxazolidinones. The treatment can involve administering a composition having both active agents or administration of the inventive compounds followed by or preceded by administration of an additional active antibacterial agent.

Types of animals that may benefit from the practice of the invention include any that are susceptible to infection by an etiological agent of Bovine respiratory Disease (BRD) or alternatively, swine respiratory disease (SRD).

Exemplary animals include but are not limited to: members of the biological subfamily Bovinae which includes medium- to large-sized ungulates such as domestic dairy and beef cattle, bison, African buffalo, the water buffalo, etc. The animals may be so-called livestock raised in an agricultural setting for the production of dairy products or meat; or may be raised to perform work; or may be in another setting, e.g. in a zoo, animal reserve, etc., or raised for some other reason, e.g. as pets, show animals, for breeding purposes, etc.

Especially preferred is the use of the compounds of the current invention in beef cattle. Beef cattle are cattle raised for meat production (as distinguished from dairy cattle, used for milk production). There are three main stages in beef production: cow-calf operations, backgrounding, and feedlot operations.

Especially preferred is the use of the compounds of the current invention in feedlot operations. The compounds of the invention can be used in beef (and dairy) cattle of every age, in calf, heifers, steer, cows. The compound of the invention can be used in animals of different weight, including heavy animals of a weight higher than 350 kg.

Other exemplary animals that can be treated with the compounds and compositions of the current invention are small ruminants, such a sheep or goats or pseudoruminants, such as e.g. camels or lamas. In one embodiment the compounds of the current invention is used to treat respiratory diseases such as enzootic pneumonia of lambs and/or adult sheep (ewes, rams) that are kept for meat or as breeding stock. Enzootic pneumonia is an acute infectious disease of sheep characterised by fever, nasal discharge, pneumonitis and pleuritis.

The compounds of the current invention can be alternatively used to treat Swine respiratory disease (SRD), that is a disease of animals of the family Suidae. Suidae are commonly called pigs, swine, hogs, or boars. The compounds of the current invention can be administered in general to all swine animals; to sucker, weaner, boars, barrows, gilts or sows. It can be used in one or more of the phases of swine farming for meat: suckling pigs, feeder pigs, grower, and finisher pigs or in backfatter pigs. Alternatively it can be used in breeding stocks, i.e. in breeding sows, gilts or boars or the offspring of such animal as replacement breeding stock.

In one embodiment, the animal that is treated is a bovine animal and the disease that is treated is BRD. In another embodiment the animal is a suidae (porcine) animal and the disease that is treated is SRD. The compounds of the current invention can be used to treat diseased animals that display clinical symptoms of Bovine Respiratory disease or Swine respiratory disease.

The compounds of the current invention can additionally or alternatively be used to treat animals with subclinical infections with *Pasteurella* spp., *Mannheimia* spp., and *Histophilus* spp. infections. A subclinical infection is nearly or completely asymptomatic (no disease signs or symptoms). Therefore identifying affected animals early in the course of BRD or SRD is difficult and subclinical infection is mainly detected at the slaughterhouse when checking the lungs for lesions. However, subclinical BRD or SRD infection result in lower average daily gains (ADG).

In addition to treatment purposes, the compositions and methods of the invention are also suitable for metaphylactic use. For example, in case of an outbreak of Bovine Respiratory disease or Swine respiratory disease, administration of the compounds of the current invention to non-affected (or subclinical infected) animals, especially those which are in close contact with those showing clinical signs of disease, could prevent the spread of the infection.

In addition, prophylactic treatment might be undertaken in bovines considered to be vulnerable to infection and/or in whom infection could have grave consequences, e.g. calves, show cattle, pregnant females, prize bulls or boars, etc., whether or not an outbreak of the disease is known to have occurred. Another option is the prophylactic administration of compounds according to the current invention in animals before shipping and other stress inducing events to prevent outbreak of the disease in such animals.

The same concept of prophylactic or metaphylactic treatment, as described in the herein applies to swine animals at risk for SRD.

In some embodiments, one or more, preferably one compound according to this invention is used to treat an infection by a pathogen that is resistant to one or more other antibacterial agents. In some embodiments, the compound according to this invention is active against a pathogen, that is resistant to one or more of the following antibacterials: macrolide antibiotics, aminoglycosides, fluoroquinolones, or cephalosporins, especially one or more selected from the group of tylosin, erythromycin, tildipirosin, timicosin, tulathromycin, gamithromycin, gentamicin, neomycin, enrofloxacin, ciprofloxacindanafloxaxin, oxytetracycline, chlortetracycline, cefquinome, ceftiofur or florfenicol, sulfonamides or penicillin.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

Dosage forms useful in the current invention can be liquid, semi-solid or solid dosage forms. Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is mixed and reconstituted with a diluent (e.g. water) as a solution, or as a suspension immediately prior to injection. The principal advantage of this dosage form is that it overcomes the problem of instability in solution or suspension.

One dosage route (administration route) is the parenteral, especially injection administration (e.g. subcutaneous injection, intravenous injection, intramuscular injection, etc.). Parenteral formulations and delivery systems for non-oral routes comprise liquids (e.g. solutions, suspensions, emulsions, and dry powders for reconstitution), semi-solids and solids (e.g. implants). The majority of implants, that are used in veterinary medicine, are compressed tablets or dispersed matrix systems in which the drug is uniformly dispersed within a nondegradable polymer or alternatively extrusion products. In one embodiment the compounds of the current invention are administered subcutaneously.

Another possible dosage route is the oral dosage route, wherein the compound according to this invention is administered via the mouth. Oral dosage forms suitable for oral administration comprise liquids (e.g. injectable, drench, in-feed or drinking water formulations), semi-solids (e.g. pastes, gels), and solids (e.g. tablets, capsules, powders, granules, chewable treats, premixes and medicated blocks). A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a small amount of a liquid or solid carrier. This "premix" is, in turn, dispersed in the animal's regular feed using, for example, a conventional mixer.

Several modified-release delivery systems have been developed, that take advantage of the unique anatomy of the ruminant forestomach, i.e. for intra-ruminal administration. An intraluminal bolus is a specific formulation for ruminants and pseudo-ruminants (cattle, sheep, goats, buffalos, camelids, deer etc.). It is a veterinary delayed release delivery system which remains in the rumeno-reticular sac of a ruminant animal over an extended period of time and in which the therapeutically active substance has a predictable and delayed release pattern. Such intraluminal boluses are usually administered using a balling gun or another suitable device.

It is contemplated that the compounds according to the current invention may alternatively be administered topically (e.g., transdermal via a spot-on, pour-on or spray, or alternatively as a nasal spray or by inhalation).

For instance the compounds according to this invention may be administered topically using a transdermal formulation (i.e. a formulation that passes through the skin). Alternatively the compounds according to this invention may be administered topically via the mucosa, e.g. as nasal spray. Further aspects regarding formulation of drugs and various excipients are found in, for example, Gennaro, A. R., et al., eds., Remington: The Science and Practice of Pharmacy (Lippincott Williams & Wilkins, 20th Ed., 2000).

In carrying out the method of this invention, a specified compound according to the invention is preferably administered parenterally to an infected or susceptible animal.

In another embodiment the compound is administered orally (especially in case of SRD).

When the compound according to this invention is administered orally or parenterally by subcutaneous injection, the total dose is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For BRD or SRD, for example, the dose is generally from about 0.5 to about 15 mg/kg, from about 1 to about 10 mg/kg. The same dose range may be suitable for other dosage routes. The desired dose, however, may be less in some instances where the compound according to this invention is administered intravenously.

The dose used to control *Pasteurella multocida*, *Mannheimia haemolytica* or *Histophilus somni* infections or especially BRD will vary with the compound, the severity of the infection, and the age, weight, and condition of the animal. The total dose required for several days protection will generally, however, be in the range of from about 1 to about 40 mg/kg bodyweight, and preferably will be in the range of from about 2.5 to about 35 mg/kg. Similar dosages are administered to pigs to treat SRD. Protection for up to about seven days can be provided by a single injection; the length of protection will depend upon the dose given. The total dose can also be divided into smaller doses given at intervals, such as once daily for two to seven days. Obviously, other suitable dosage regimens can be constructed.

A single administration of a composition comprising a compound according to this invention can be sufficient to treat an infection and to clinically and/or bacteriologically cure BRD or SRD, or at least diminish the clinical symptoms in diseased animals; this is called "one shot" administration. Although the administration of such a "one-shot" single dose is very suitable, it is contemplated that multiple doses can be used, e.g. two administrations 12-24 hours apart or alternatively, two administrations, 48-72 hours apart.

Factors affecting the preferred dosage may include, for example, infection to be treated, the type (e.g., species and breed), age, size, sex, diet, activity, and condition of the of the infected animal; the dosage route; pharmacological considerations, such as the activity, efficacy, pharmacokinetic, and toxicology profiles of the particular compound of the invention and the composition administered; and whether the compound according to this invention being administered as part of a combination of active ingredients.

Thus, the preferred amount of the compound according to this invention can vary, and, therefore, can deviate from the typical dosages set forth above. Determining such dosage adjustments is generally within the skill of those in the art. The effective dosage will vary; for example, for prophylactic treatment relatively low doses would be administered over an extended time.

The compounds of this invention may be formulated for parenteral administration by methods recognized in the veterinary pharmaceutical art. Effective injectable compositions containing these compounds may be in either suspension or solution form. In the preparation of suitable formulations, it will be recognized that, in general, the water solubility of the acid addition salts is greater than that of the corresponding free bases. Similarly, the free bases are more soluble in dilute acids or in acidic solutions than in neutral or basic solutions.

In the solution form a compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate.

Injectable suspension compositions employ a liquid suspending medium, with or without adjuvants, as a vehicle. The suspending medium can be, aqueous or non-aqueous, e.g. water, polyethylene glycol, benzyl alcohol, N methyl pyrrolidone, triacetin, inert oils such as vegetable oils or highly refined mineral oils.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents. Many substances which affect the hydrophilicity, density, and surface tension of the liquid suspending medium can assist in making injectable suspensions in individual cases. For example, silicone antifoams, sorbitol, and sugars can be useful suspending agents. Other conventional ingredients such as preservatives, buffers, surfactants, or thickeners can be present in the injectable formulation.

The compounds of this invention exhibit unexpectedly high antibacterial activity against *Mannheimia haemolytica* and *Pasteurella multocida*. For example, representative compounds were tested against *Mannheimia haemolytica* and *Pasteurella multocida*, using the conventional broth-dilution assay. The minimal inhibitory concentrations (MIC's) of representative compounds against these species are summarized in Table C.

The concentration of the compounds according to this invention in the applied dosage form may vary widely depending on, for example, the dosage route. In general, the concentration for injectable or oral administration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

Preferred concentration in drinking water are from 0.01 to 0.05% weight by volume, particularly 0.01 to 0.025%, and in-feed from 100 to 400 ppm (g/metric ton), particularly 100 to 200 ppm.

In another aspect the present invention thus provides the administration of a pharmaceutical composition comprising an antibacterial effective amount of one or more, preferably one compound according to this invention and one or more pharmaceutically acceptable excipients to an animal, especially a bovine animal or alternatively a porcine animal, especially for the treatment of BRD or SRD.

The formulation type chosen for a dosage form in any instance will depend upon the particular purpose envisaged and the physical, chemical and biological properties of the compound according to this invention.

If the compound according to this invention is administered parentally via an injection, the concentration of the compound according to this invention in the composition/formulation/dosage form preferably is sufficient to provide the desired therapeutically effective amount of the compound according to this invention in a volume that is acceptable for parenteral (subcutaneous) administration and allows an injection volume of less than 20 ml/per injection site.

In one embodiment the composition of a compound according to the invention is administered in a non-edible tissue of the animal that is removed at slaughter and does not enter the human food chain, e.g. in the ear or at the base of the ear (at the junction of the pinna with the cranium), or behind the ear, e.g. as described in WO1998041207 or WO2003079923, the content of which is incorporated by reference. Injection in alternative animal tissues of food producing animals, that do not enter the (human) food chain after slaughtering of the animal are also envisaged.

Examples of Contemplated Combination Therapies

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different diseases or conditions.

Contemplated active ingredient(s) that may be administered in combination with the compounds of the current invention include, for example, antibacterials, anti-inflammatories, pharmaceutically acceptable anthelmintics, insecticides and acaricides, insect growth regulators, hormones, immunostimulats, dermatological preparations (e.g. antiseptics and disinfectants), and immunobiologicals (e.g., vaccines and antisera) for disease prevention.

Therefore, this invention is also directed to the use as a medicament of combinations comprising a) one or more compounds according to this invention with b) one or more pharmaceutically acceptable active compounds which differ in structure from component a). The active compounds b) are preferably anti-inflammatory compounds, more preferably selected from the group consisting of non-steroidal anti-inflammatory agents (NSAID's), such as e.g. flunixin meglumine, meloxicam, carprofen, ketoprofen, phenylbutazone, or Aspirin. In one embodiment one compound according to the invention is combined with flunixin. In another embodiment one compound of the invention is combined with meloxicam. Preferably such combination is used to treat BRD in cattle.

Combination means that a compound of the current invention is administered in a common formulation with the one or more pharmaceutically acceptable active compounds which differ in structure. Alternatively the compound according to the invention is administered to the animal in parallel (not more than approximately 30 minutes apart) from one or more pharmaceutically acceptable active compounds which differ in structure.

In another embodiment the one or more pharmaceutically acceptable active compounds which differ in structure b) are antibacterials especially one or more selected grom the group of tylosin, erythromycin, tildipirosin, timicosin, tulathromycin, gamithromycin, gentamicin, neomycin, enrofloxacin, ciprofloxacin, danofloxaxin, oxytetracycline, chlortetracycline, cefquinome, ceftiofur or florfenicol, sulfonamides or penicillin.

Veterinary formulations for use in the present invention may be prepared by mixing the ingredients in the required proportions. The formulation is then packaged into an appropriate container containing single or multiple doses ready for administration (ready to use RTU) or alternatively, can be mixed with a diluent before administration.

Features of the invention have been described in embodiments in the present application; however, for brevity not all combinations of the features are literally described. Combinations of features as described herein are however expressly considered to be part of the invention.

The invention will now be further described by the following, non-limiting, examples:

Example 1 (Synthesis Examples)

Procedure for the Synthesis of Aldehyde Containing Resins Bearing a Pyrimidine Core Structure:

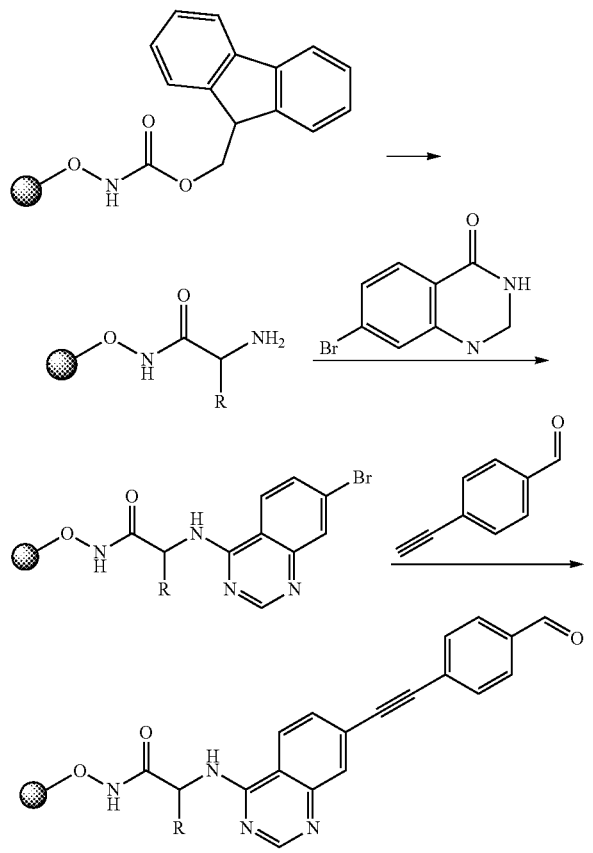

To a mixture of 2-chlorotrityl resin (3 g, 3 mmol) and (9H-fluoren-9-yl)methyl hydroxycarbamate (0.77 g, 3 mmol) in dichloromethane (10 mL) was added DIEA (1.55 g, 12 mmol) at 25° C. and the mixture was purged with a stream of nitrogen for 16 hours. To the mixture was then added methanol (3 mL) and mixing was continued for 30 minutes. The resin was then collected by filtration and washed with DMF (3×20 mL) and treated with 20% v/v piperidine in DMF (20 mL) for 30 minutes. After collection by filtration, the resin was washed with DMF (5×20 mL) and drained completely. To the resin was then added the N-Fmoc-protected amino acid (9 mmol) and DIEA (2.3 g, 18 mmol) in DMF (10 mL) followed by HATU (3.25 g, 8.55 mmol) and mixing was continued for 1 hour when the resin was collected by filtration and washed with DMF (3×20 mL). The resin was then treated with 20% v/v piperidine in DMF (20 mL) for 30 minutes and collected by filtration again followed by washing with DMF (5×20 mL). A solution of 7-bromoquinazolin-4(3H)-one (2.02 g, 9 mmol) and (benzotriazol-1-yloxy)tris(dimethylamino) phosphonium hexafluorophosphate (BOP, 3.98 g, 9 mmol) in DMF (5 mL) was then treated with DBU (3 eq, 9 mmol) at 0° C. and after stirring for 10 minutes at 0° C., the mixture was then added to a mixture of the resin and DBU (3 eq, 9 mmol) in DMF (10 mL). Mixing at 25° C. was continued for 2 hours, the resin collected by filtration and washed with dichloromethane (3×20 mL), methanol (3×20 mL) and finally DMF (20 mL). The resin was then mixed with DMF (20 mL) and DIEA (3.88 g, 30 mmol) followed by the addition of 4-ethynylbenzaldehyde (0.78 g, 6 mmol), CuI (0.29 g, 1.5 mmol) and Pd(PPh$_3$)$_2$Cl$_2$ (0.42 g, 0.6 mmol) and agitated by introduction of a stream of nitrogen for 16 hours at 25° C. The resin was drained, washed with DMF (3×20 mL) and methanol (3×20 mL) and dried in vacuo to give the aldehyde containing resin which was used in the next steps without further purification.

Using this procedure, the corresponding amino acid-containing aldehyde resins were obtained using Fmoc-N-Thr($^t$Bu)-OH and Fmoc-N-3-NHBoc-Val-OH.

Procedure for the Synthesis of an Aldehyde Containing Resin Bearing a 1,2-Benzothiazole Core Structure:

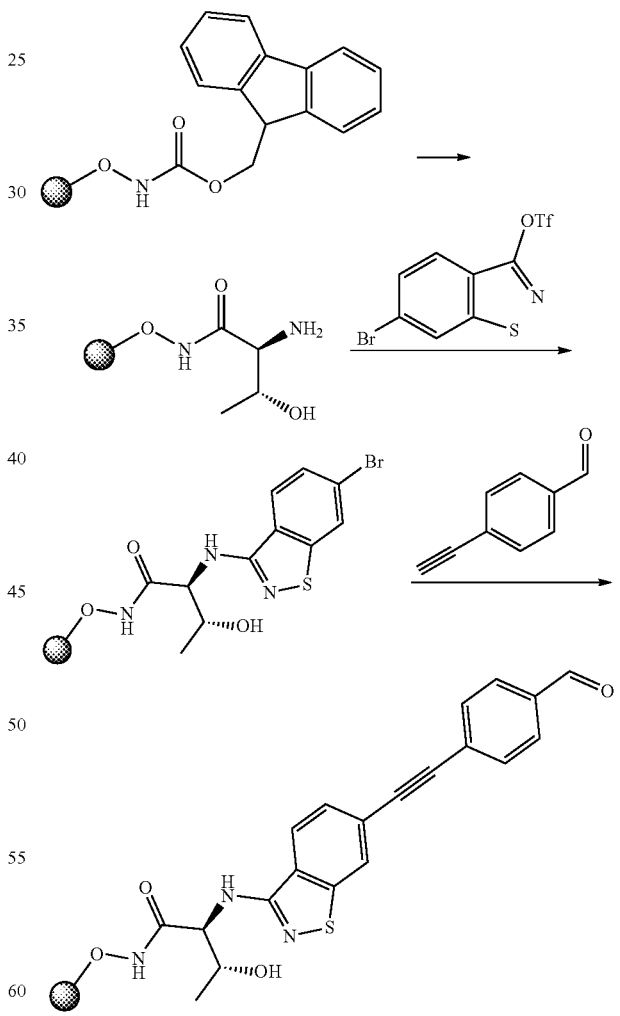

To a mixture of 2-chlorotrityl resin (3 g, 3 mmol) and (9H-fluoren-9-yl)methyl hydroxycarbamate (0.77 g, 3 mmol) in dichloromethane (10 mL) was added DIEA (1.55 g, 12 mmol) at 25° C. and the mixture was purged with a stream of nitrogen for 16 hours. To the mixture was then added methanol (3 mL) and mixing was continued for 30 minutes. The resin was then collected by filtration and washed with DMF (3×20 mL) and treated with 20% v/v piperidine in DMF (20 mL) for 30 minutes. After collection by filtration, the resin was washed with DMF (5×20 mL) and drained completely. To the resin was then added Fmoc-N-Thr($^t$Bu)-OH (3.58 g, 9 mmol) and DIEA (2.3 g, 18 mmol) in DMF (10 mL) followed by HATU (3.25 g, 8.55 mmol) and mixing was continued for 1 hour when the resin was collected by filtration and washed with DMF (3×20 mL). The resin was then treated with 20% v/v piperidine in DMF (20 mL) for 30 minutes and collected by filtration again followed by washing with DMF (5×20 mL). A solution of (6-bromo-1,2-benzothiazol-3-yl) trifluoromethanesulfonate (2.173 g, 6 mmol) in DMF (10 mL) was then added to the resin followed by the addition of DIEA (1.53 g, 12 mmol) and mixing was continued. After 16 hours at room temperature, the resin was collected by filtration and washed with DMF (3×20 mL). It was then mixed with DMF (20 mL) and DIEA (3.88 g, 30 mmol) followed by the addition of 4-ethynylbenzaldehyde (0.78 g, 6 mmol), CuI (0.29 g, 1.5 mmol) and Pd(PPh$_3$)$_2$Cl$_2$ (0.42 g, 0.6 mmol) and agitated by introduction of a stream of nitrogen for 16 hours. The resin was drained, washed with DMF (3×20 mL) and methanol (3×20 mL) and dried in vacuo to give the aldehyde containing resin which was used in the next steps without further purification.

General Procedure for the Reductive Amination of the Aldehyde-Containing Resins with Amines:

A solution of the respective amine (3 mmol) and trimethyl orthoformate (359 µL, 3.25 mmol) in THF (10 mL) was added to a vial containing the resin-bound aldehyde (0.5 mmol) from the previous steps. An atmosphere of nitrogen was established and after mixing for 5 minutes, acetic acid (0.35 mL, 6.15 mmol) was added followed by NaCNBH$_3$ (141 mg, 2.25 mmol). Mixing was continued for 16 hours after which the resin was filtered, drained and washed with DMF (2×10 mL) and methanol (3×10 mL), drained again and dried in vacuo. Cleavage from the resin was achieved by treatment with 1% v/v of trifluoroacetic acid in dichloromethane (5 mL) for 30 minutes. The mixture was filtered and the filtrate treated with diisopropyl ether to form a yellow precipitate which was purified by preparative HPLC using a, e.g., Gilson GX-281 semi-preparative HPLC system equipped with a Luna 200×25 mm (C18, 10µ) or a Gemini 150×30 mm (C18, 5µ) column applying a gradient consisting of 0.1% v/v of trifluoroacetic acid/water and acetonitrile.

The product containing fractions were collected, concentrated by freeze-drying and the residual trifluoroacetic acid was removed by another reverse-phase chromatography using a gradient consisting of aqueous ammonium hydrogencarbonate (7.5 mmol/L) and acetonitrile.

Using this procedure, the following compounds can be synthesized: Compound No.: 1-6, 10-15 and 16-21.

Synthesis of 3-(tert-butoxycarbonylamino)-2-(9H-fluoren-9-ylmethoxycarbonylamino)-3-methyl-butanoic acid

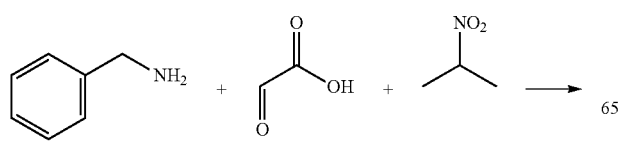

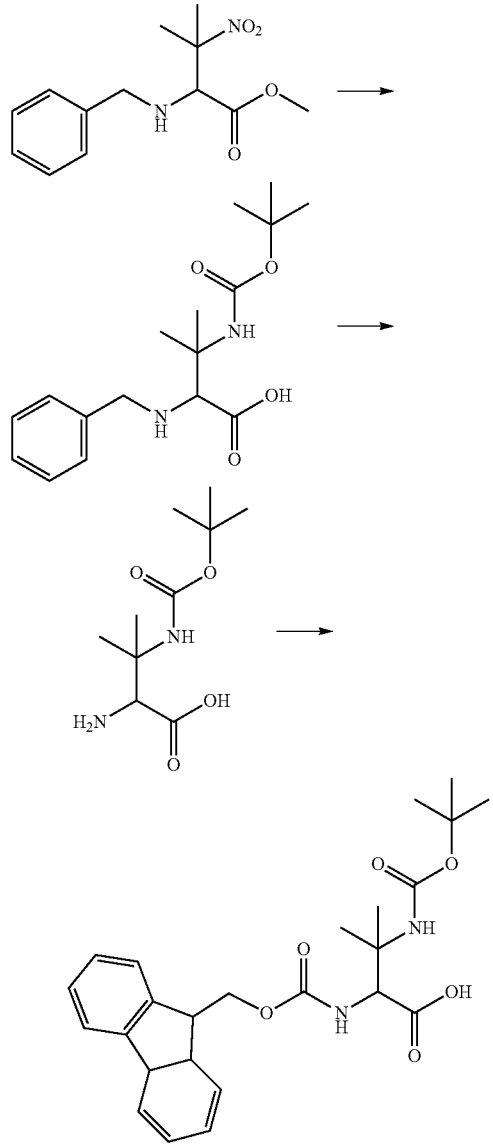

Step 1: 2-(Benzylamino)-3-methyl-3-nitrobutanoic acid

2-Nitropropane (292 mL, 3250 mmol) was added to a cooled (10° C.) solution of potassium hydroxide (219 g, 3900 mmol) in water (750 mL). The reaction mixture was kept between 0-10° C. and benzylamine (355 ml, 3250 mmol) was added dropwise. To this mixture a solution of 2-oxoacetic acid (370 ml, 3250 mmol) in water (1.1 L) was added over a period of 90 minutes and stirring at room temperature was continued for 20 hours. The reaction mixture was diluted with water (8 L) and concentrated hydrochloric acid was added until pH 2 was reached. The resulting precipitate was collected by filtration, washed with water (10 L) and dried at 40° C. under reduced pressure to give the desired compound.

Step 2: Methyl 2-(benzylamino)-3-methyl-3-nitrobutanoate

Two identical batches were prepared in parallel in which iodomethane (34.8 ml, 556 mmol) was added dropwise to a mixture of 2-(benzylamino)-3-methyl-3-nitrobutanoic acid (146 g, 506 mmol) and cesium carbonate (181 g, 556 mmol) in DMF (1530 ml) at −78° C. After the addition was complete, the mixture was allowed to stir without further cooling for 2.5 hours. Both batches were combined, diluted with ethyl acetate (2.1 L) and 1M hydrochloric acid (556 mL). The layers were separated and the organic phase washed with water (900 mL) and the aqueous phase was extracted with ethyl acetate (300 mL). The combined organic phases were washed with 500 mL of saturated aqueous NaHCO$_3$ and dried over Na$_2$SO$_4$. After filtration and evaporation of all volatiles, the desired compound was obtained as an oil.

Step 3: Methyl 3-amino-2-(benzylamino)-3-methylbutanoate

Acetic acid (654 mL) was added to a mixture of zinc (187 g, 2854 mmol), ethanol (1.1 L) and water (100 mL) and stirred at −20° C. Methyl 2-(benzylamino)-3-methyl-3-nitrobutanoate (152 g, 571 mmol) dissolved in ethanol (1.1 L) was then added dropwise over a period of 60 minutes. The mixture was stirred without further cooling overnight, filtered through celite and concentrated in vacuo. The residue was taken up in a mixture of ethyl acetate (1000 mL) and water (1000 mL). Under ice cooling, 5 M NaOH was added until the mixture reached pH 9. The mixture was then filtered through celite, the layers were separated and the aqueous phase extracted with ethyl acetate (300 mL). The combined organic layers were dried over Na$_2$SO$_4$, filtered and the solvent was evaporated under reduced pressure to give the desired compound as an oil.

Step 4: Methyl 2-(benzylamino)-3-((tert-butoxycarbonyl)amino)-3-methylbutanoate

Di-tert-butyl dicarbonate (230 g, 1054 mmol) was added to a stirred mixture of methyl 3-amino-2-(benzylamino)-3-methylbutanoate (83 g, 351 mmol) and Na$_2$CO$_3$ (112 g, 1054 mmol) in dioxane (830 mL). Stirring at room temperature was continued for 18 hours. The reaction mixture was diluted with water (800 mL) and dichloromethane (800 mL) and the layers separated. The aqueous phase was extracted with dichloromethane (500 mL) and the combined organic fractions were dried over Na$_2$SO$_4$, filtered and concentration to dryness provided 250 g of a yellow oil. This was taken up in n-pentane (500 mL) and stirred at room temperature overnight. The mixture was then stirred at 0° C. for 1 hour and the precipitate was collected by filtration and washed with cold n-pentane (200 mL). The filtrate was concentrated in vacuo and purified by column chromatography on silica gel using n-pentane/ethyl acetate as the eluent. The product containing fractions were combined, concentrated to dryness and combined with the filter residue to yield the desired compound.

Step 5: 2-(Benzylamino)-3-((tert-butoxycarbonyl)amino)-3-methylbutanoic acid

Methyl 2-(benzylamino)-3-((tert-butoxycarbonyl)amino)-3-methylbutanoate (145 g, 431 mmol) was added to a mixture of NaOH (138 g, 3448 mmol) in methanol (150 mL) and water (150 mL) at room temperature. The reaction mixture was stirred at 70° C. for 2 hours. After cooling to room temperature, the reaction mixture was concentrated under reduced pressure. The resulting mixture was cooled with an ice bath and acidified with 1.0 M HCl until pH 5.4 was reached. The resulting white precipitate was collected by filtration, washed with cold water and dried in vacuo to give the crude product which was used in the next step without further purification.

Step 6: 2-Amino-3-((tert-butoxycarbonyl)amino)-3-methylbutanoic acid 2-(Benzylamino)-3-((tert-butoxycarbonyl)amino)-3-methylbutanoic acid (120 g, 372 mmol) was added to a suspension of palladium hydroxide on carbon (25 g, 35.6 mmol) in methanol (500 mL) and the mixture was stirred for 16 hours at 25° C. under an atmosphere of hydrogen (P=48 psi). The reaction mixture was filtered, the filter residue was washed with methanol several times and the combined filtrates were evaporated under reduced pressure to give the desired product.

Step 7: 3-(tert-Butoxycarbonylamino)-2-(9H-fluoren-9-ylmethoxycarbonylamino)-3-methyl-butanoic acid (9H-Fluoren-9-yl)-methyl-(2,5-dioxopyrrolidin-1-yl) carbonate (142 g, 420 mmol) was added to a stirred mixture of 2-amino-3-((tert-butoxycarbonyl)amino)-3-methylbutanoic acid (65 g, 280 mmol) and NaHCO$_3$ (47 g, 560 mmol) in acetone (780 mL) and water (520 mL) and stirred at room temperature for 3 hours. The reaction mixture was concentrated under reduced pressure and the resulting mixture was cooled with an ice bath. Hydrochloric acid (1 M) was added until pH 6 was reached and the mixture was then extracted with ethyl acetate (3×500 mL). The combined organic fractions were dried, evaporated to dryness and submitted to column chromatography on silica gel (ethyl acetate/petroleum ether) to provide a solid. MS: 355 (M-Boc+1). $^1$H NMR (400 MHz, CDCl$_3$): δ 7.76 (d, J=7.6 Hz, 2H), 7.5-7.6 (m, 2H), 7.3-7.4 (m, 4H), 4.59 (b, 1H), 4.4-4.5 (m, 2H), 4.24 (t, J=6.8 Hz, 1H), 1.3-1.5 (b, 15H).

Synthesis of (6-bromo-1,2-benzothiazol-3-yl) trifluoromethanesulfonate

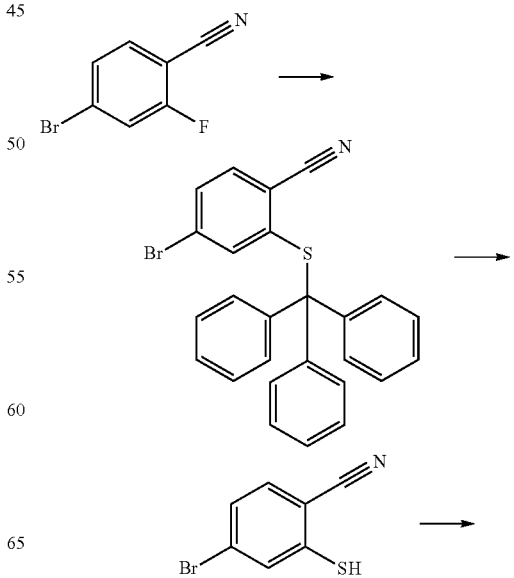

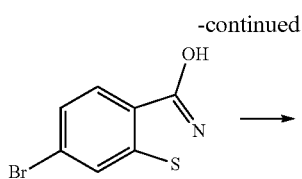

Step 1: 4-Bromo-2-tritylthio-benzonitrile

To a solution of triphenylmethanethiol (41.5 g, 150 mmol) in tetrahydrofuran (100 mL) under an atmosphere of nitrogen was added sodium hydride (3.6 g, 150 mmol) and the mixture was stirred at 25° C. for 1 hour. After cooling to 0° C., a solution of 4-bromo-2-fluorobenzonitrile (20 g, 100 mmol) in tetrahydrofuran (50 mL) was added dropwise. The reaction mixture was allowed to attain room temperature and stirring was continued for 16 hours. The mixture was then diluted with saturated aqueous ammonium chloride solution at 0° C. Then the mixture was extracted with dichloromethane (200 mL) and the organic layer separated and concentrated to dryness to provide the desired compound which was used in the next step without further purification.

Step 2: 4-Bromo-2-mercaptobenzonitrile

To 4-bromo-2-tritylthio-benzonitrile (5 g, 10.96 mmol) was added a pre-cooled (0° C.) mixture of trifluoroacetic acid (30 mL), triisopropyl silane (3 mL) and dichloromethane (17 mL) in one portion. The reaction mixture was then stirred at 25° C. for 1 hour and evaporated to dryness and submitted to column chromatography on silica gel (dichloromethane/methanol) to provide the desired compound.

Step 3: 6-Bromo-1,2-benzothiazol-3-ol

To 4-bromo-2-mercaptobenzonitrile (5 g, 23.36 mmol) was added sulfuric acid (30 mL) at 25° C. The reaction mixture was then stirred at 100° C. for 4 hours, allowed to attain room temperature and then diluted with saturated aqueous NaHCO$_3$ solution until pH 8 was reached. A yellow precipitate was collected by filtration and dried to provide the title compound which was used in the next step without further purification.

Step 4: (6-Bromo-1,2-benzothiazol-3-yl) trifluoromethanesulfonate

To 6-bromo-1,2-benzothiazol-3-ol (2.5 g, 10.87 mmol) in dichloromethane (8 mL) at 0° C. was added dropwise a solution of trifluoromethanesulfonic anhydride (3.68 g, 13.04 mmol) in dichloromethane (2 mL). The reaction mixture was allowed to stir at 25° C. for 30 minutes and was then extracted with 1N HCl followed by brine. The organic layer was separated, dried over Na$_2$SO$_4$, evaporated to dryness and submitted to column chromatography on silica gel (dichloromethane/methanol) to provide the title compound. $^1$H NMR (400 MHz, CDCl$_3$): δ 8.03 (s, 1H), 7.75 (d, J=8.8 Hz, 1H), 7.61 (dd, J=8.8 Hz, J=1.2 Hz, 1H).

Synthesis of (2S,3R)—N,3-di-tert-butoxy-2-[[6-[2-(4-formylphenyl)ethynyl]-1-isoquinolyl]amino]butanamide

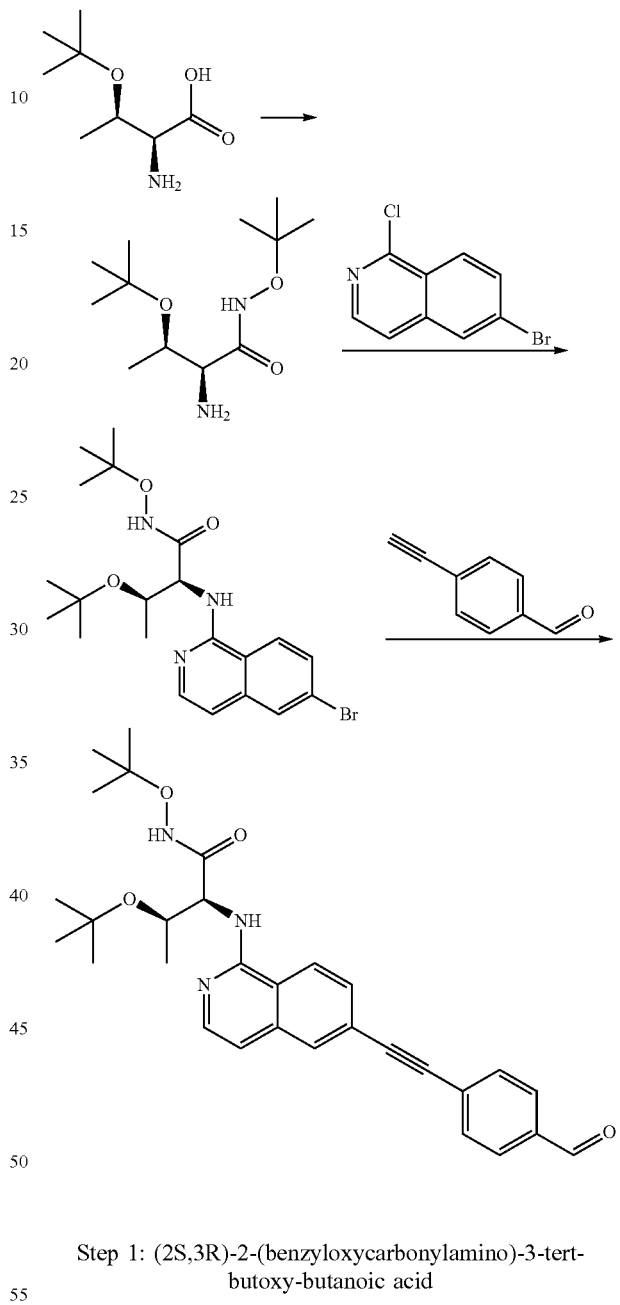

Step 1: (2S,3R)-2-(benzyloxycarbonylamino)-3-tert-butoxy-butanoic acid

To (2S,3R)-2-amino-3-(tert-butoxy)butanoic acid (20 g, 114 mmol) in THF (170 mL) and saturated NaHCO$_3$ (200 mL) was added a solution of benzyl carbonochloridate (23.37 g, 137 mmol) in THF (30 mL) dropwise at 0° C. The mixture was allowed to react for 1 hour and was then diluted at 0° C. with 3 M HCl until pH 1 was reached. The mixture was then extracted with ethyl acetate (200 mL) and the organic layer was washed with 3 M HCl (300 mL) and brine (2×), dried over Na$_2$SO$_4$ and concentrated to dryness to provide the desired compound which was used without further purification in the next step.

Step 2: Benzyl N-[(1S,2R)-2-tert-butoxy-1-(tert-butoxycarbamoyl)propyl]carbamate To a solution of (2S,3R)-2-(benzyloxycarbonylamino)-3-tert-butoxy-butanoic acid (24 g, 78 mmol) and O-(tert-butyphydroxylamine (8.33 g, 93 mmol) in DMF (200 mL) was added DIEA (20.16 g, 156 mmol) and HATU (35.5 g, 78 mmol) at 0° C. in one portion. The mixture was allowed to react at 25° C. for 2 hours and then partitioned between 1 M HCl (200 mL) and ethyl acetate (400 mL). The organic layer was separated and washed with 1M HCl (2×200 mL) followed by saturated aqueous NaHCO$_3$ (3×200 ml) and brine (2×200 mL). After drying over Na$_2$SO$_4$, the organic layer was concentrated and purified by column chromatography on silica gel (petroleum ether/ethyl acetate) to provide the desired compound.

Step 3: (2S,3R)-2-amino-N,3-di-tert-butoxy-butanamide

To a mixture of benzyl N-[(1S,2R)-2-tert-butoxy-1-(tert-butoxycarbamoyl)propyl]carbamate (10 g, 26.3 mmol) in methanol (100 mL) was added palladium on carbon (1 g, 26.3 mmol) and the mixture was allowed to react in the presence of hydrogen (P=50 psi) at 25° C. for 2 hours. Then the reaction mixture was filtered and concentrated under reduced pressure to provide the title compound which was used in the next step without further purification.

Step 4: (2S,3R)-2-[(6-bromo-1-isoquinolyl)amino]-N,3-di-tert-butoxy-butanamide A mixture of (2S,3R)-2-amino-N,3-di-tert-butoxy-butanamide (2 g, 8.1 mmol), 6-bromo-1-chloroisoquinoline (1.97 g, 8.1 mmol) and K$_2$CO$_3$ (2.47 g, 17.8 mmol) in DMSO (6 mL) was heated at 100° C. for 3 days. The reaction mixture was then allowed to attain room temperature and partitioned between water (100 mL) and ethyl acetate (200 mL). The organic layer was separated and extracted with brine (5×100 mL), dried over Na$_2$SO$_4$, concentrated under reduce pressure and purified by column chromatography on silica gel (petroleum ether/ethyl acetate) to provide the desired compound.

Step 5: (2S,3R)—N,3-di-tert-butoxy-2-[[6-[2-(4-formylphenyl)ethynyl]-1-isoquinolyl]amino] butanamide To a mixture of copper(I) iodide (0.22 g, 1.15 mmol) and Pd(PPh$_3$)$_2$Cl$_2$ (0.4 g, 0.58 mmol) under an atmosphere of nitrogen was added tetrahydrofuran (8 mL) followed by diisopropylamine (8 mL), (2S,3R)-(2S,3R)-2-[(6-bromo-1-isoquinolyl)amino]-N,3-di-tert-butoxy-butanamide (1.3 g, 2.87 mmol) and 4-ethynylbenzaldehyde (1.1 g, 8.62 mmol). The reaction mixture was stirred at 70° C. for 16 hours and allowed to attain to room temperature. All volatiles were then removed in vacuo and the residue was purified by column chromatography on silica gel (petroleum ether/ethyl acetate) to provide the title compound. MS: 502 (M+1).

General Procedure for the Reductive Amination of (2S,3R)—N,3-di-tert-butoxy-2-[[6-[2-(4-formylphenyl)ethynyl]-1-isoquinolyl]amino] butanamide with Primary Amines To the solution of (2S,3R)—N,3-di-tert-butoxy-2-((6-((4-formylphenyl)ethynyl)isoquinolin-1-yl)amino)butanamide (100 mg, 0.2 mmol) in THF (1 mL) was added the respective amine (5 eq, 1.0 mmol) and acetic acid (12 mg, 0.2 mmol) in one portion at 25° C. The mixture was stirred at 25° C. for 10 minutes and then solid NaBH$_3$CN (25 mg, 0.4 mmol) was added. The reaction mixture was then stirred for 4 hours and partitioned between ethyl acetate (50 mL) and saturated aqueous NH$_4$Cl (50 mL). The organic layer was separated and extracted with brine (3×50 mL), dried over Na$_2$SO$_4$, concentrated in vacuo and then purified by column chromatography on silica gel (petroleum ether/ether acetate) to provide the respective secondary amine products.

General Procedure for the Removal of the Tert-Butyl Protecting Groups.

To a solution of the product from the previous reductive amination step (1 eq, 0.13 mmol) in dichloromethane (0.5 mL) was added TiCl$_4$ (98 mg, 0.52 mmol) in one portion at 0° C. The mixture was stirred at 0° C. for 4 hours when saturated aqueous NaHCO$_3$ (50 mL, pre-cooled at 0° C.) was added. The reaction mixture was allowed to attain room temperature and was then centrifuged. The supernatant was removed and the remaining solid was purified by preparative HPLC using a e.g. Gilson GX-281 semi-preparative HPLC system equipped with a Luna 200×25 mm (C18, 10µ) or a Gemini 150×30 mm (C18, 5µ) column applying a gradient consisting of 0.05% NH$_4$HCO$_3$/water and acetonitrile.

Using this procedure, the following compounds can be synthesized: Compound No.: 7-9.

Specific Compounds

Table A provides for each of the exemplified compounds the structure according to Formula A below. Compounds of Formula A:

Formula A

The residue A in Table A is described either in form of a molecular formula or in form of a chemical name, in this latter case A is an amine which is linked with its nitrogen atom to the remainder of the molecule. Stereo denotes the absolute configuration wherein the first assignment relates to the atom a to the hydroxamate-carbonyl group; the second assignment relates to the R1 moiety.

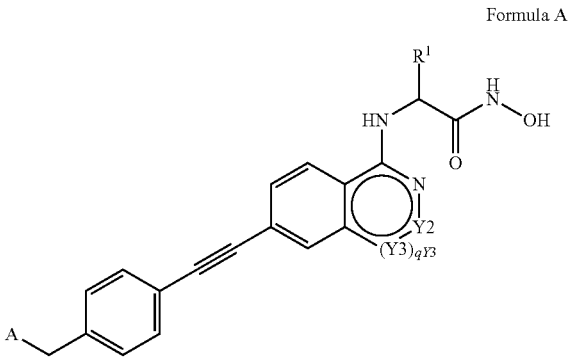

Formula A

TABLE A

| No | A | R1 | Stereo | Y2 | Y3 |
|---|---|---|---|---|---|
| 1 | morpholine | CH(CH3)OH | S, R | CH | N |
| 2 | cyclopropylamine | CH(CH3)OH | S, R | CH | N |
| 3 | CH3O(CH2)2NH— | CH(CH3)OH | S, R | CH | N |
| 4 | CH2=CHCH2NH— | CH(CH3)OH | S, R | CH | Z |
| 5 | benzylamine | CH(CH3)OH | S, R | CH | Z |
| 6 | CF3CH2NH— | CH(CH3)OH | S, R | CH | N |
| 7 | cyclopropylamine | CH(CH3)OH | S, R | CH | CH |

TABLE A-continued

| No | A | R1 | Stereo | Y2 | Y3 |
|---|---|---|---|---|---|
| 8 | CH2=CHCH2NH— | CH(CH3)OH | S, R | CH | CH |
| 9 | CH3O(CH2)2NH— | CH(CH3)OH | S, R | CH | CH |
| 10 | cyclopropylamine | CH(CH3)OH | S, R | —S— | qY3=0 |
| 11 | CH2=CHCH2NH— | CH(CH3)OH | S, R | —S— | qY3=0 |
| 12 | CH3O(CH2)2NH— | CH(CH3)OH | S, R | —S— | qY3=0 |
| 13 | morpholine | CH(CH3)OH | S, R | —S— | qY3=0 |
| 14 | benzylamine | CH(CH3)OH | S, R | —S— | qY3=0 |
| 15 | CF3CH2NH— | CH(CH3)OH | S, R | —S— | qY3=0 |
| 16 | cyclopropylamine | C(CH3)2NH2 | racemate | CH | N |
| 17 | CH2=CHCH2NH— | C(CH3)2NH2 | racemate | CH | N |
| 18 | CH3O(CH2)2NH— | C(CH3)2NH2 | racemate | CH | N |
| 19 | morpholine | C(CH3)2NH2 | racemate | CH | N |
| 20 | benzylamine | C(CH3)2NH2 | racemate | CH | N |
| 21 | CF3CH2NH— | C(CH3)2NH2 | racemate | CH | N |

Example 2: Analytics—HPLC Methods

Chromatographic System:
  Column: Phenomenex Jupiter Proteo C18 90A, 4.6×50 mm, 4p
  Oven: 30° C.
  Eluents: Solvent A: water/TFA (0.1%); Solvent B: acetonitrile/TFA (0.1%)
  Flow: 1.0 ml/min
  Gradient:

| Time [min] | Solvent A [%] | Solvent B [%] |
|---|---|---|
| 0.0 | 98 | 2 |
| 3.0 | 0 | 100 |
| 4.0 | 0 | 100 |
| 4.5 | 98 | 2 |
| 5 | 98 | 2 |

Run time: 5 min

Table B provides for each of the exemplified compounds of Table A the calculated molecular weight (MW), the observed mass signal (m/z), the HPLC retention time (Rt) in minutes and the number of the HPLC method as described herein ("HPLC methods").

TABLE B

| No | Rt | m/z | MW |
|---|---|---|---|
| 1 | 1.93 | 462.2 | 461.5 |
| 2 | 1.97 | 432.1 | 431.5 |
| 3 | 1.96 | 450.2 | 449.5 |
| 4 | 1.98 | 432.2 | 431.5 |
| 5 | 2.20 | 482.2 | 481.5 |
| 6 | 2.03 | 474.1 | 473.4 |
| 7 | 1.60 | 431.2 | 430.5 |
| 8 | 1.56 | 431.2 | 430.5 |
| 9 | 1.44 | 449.2 | 448.5 |
| 10 | 2.31 | 437.1 | 436.5 |
| 11 | 2.33 | 437.1 | 436.5 |
| 12 | 2.30 | 455.1 | 454.5 |
| 13 | 2.27 | 467.1 | 466.6 |
| 14 | 2.54 | 487.1 | 486.6 |
| 15 | 2.41 | 479.1 | 478.5 |
| 16 | 1.92 | 445.2 | 444.5 |
| 17 | 1.94 | 445.2 | 444.5 |
| 18 | 1.90 | 463.2 | 462.5 |
| 19 | 1.88 | 475.2 | 474.6 |
| 20 | 2.14 | 495.2 | 494.6 |
| 21 | 1.97 | 487.1 | 486.5 |

Example 3 (Biological Examples)

In-Vitro Susceptibility Testing of Representative Compounds

The Minimum inhibitory concentrations (MIC) of compounds according to the invention for a number of veterinary bacterial pathogens were determined by the broth-microdilution method according to CLSI document VET01-A4.

Microdilution trays containing a doubling dilution series of the test compound were used for the tests. The MIC results were interpreted according to the CLSI documents VET01-S3. The lowest concentration of compound at which no visible growth (i.e. no turbidity) detected by the unaided eye was recorded as the MIC.

Results

MIC Data in µM for representative compounds is shown in Table C below.

TABLE C

| No | MH 6357 | MH 6374 | MH 10720 | MH 12587 | MH 13093 | PM 6267 | PM 6391 | PM 10775 | PM 12080 |
|---|---|---|---|---|---|---|---|---|---|
| 1 | 1.6 | 3.1 | 0.2 | 3.1 | 3.1 | 1.6 | 0.2 | ≤0.1 | ≤0.1 |
| 2 | 0.8 | 1.6 | ≤0.1 | 3.1 | 3.1 | 1.6 | 0.2 | ≤0.1 | ≤0.1 |
| 3 | 6.3 | 6.3 | 6.3 | 12.5 | 6.3 | 0.2 | 0.4 | ≤0.1 | 3.1 |
| 4 | 1.6 | 3.1 | 1.6 | 6.3 | 3.1 | 0.2 | 0.4 | ≤0.1 | 1.6 |
| 5 | 0.8 | 0.8 | 0.8 | 3.1 | 1.6 | ≤0.1 | 0.2 | ≤0.1 | 0.8 |
| 6 | 0.8 | 0.8 | 0.4 | 1.6 | 0.8 | ≤0.1 | ≤0.1 | ≤0.1 | 0.4 |
| 10 | 0.2 | 0.4 | ≤0.1 | 0.8 | 0.4 | ≤0.1 | >100 | ≤0.1 | ≤0.1 |
| 11 | 0.4 | 0.4 | ≤0.1 | 1.6 | 0.8 | ≤0.1 | 0.2 | ≤0.1 | 0.4 |
| 12 | 0.8 | 0.8 | 0.2 | 3.1 | 1.6 | ≤0.1 | >100 | ≤0.1 | 0.8 |
| 13 | 3.1 | 6.3 | 1.6 | 6.3 | 3.1 | ≤0.1 | 100 | ≤0.1 | 1.6 |
| 14 | 0.8 | 0.8 | ≤0.1 | 1.6 | 0.8 | ≤0.1 | 100 | ≤0.1 | 0.2 |
| 15 | 1.6 | 1.6 | ≤0.1 | 3.1 | 1.6 | ≤0.1 | >100 | ≤0.1 | 0.4 |
| 18 | 25 | 25 | 6.3 | 50 | 25 | 3.1 | 6.3 | 0.8 | 12.5 |

The following pathogens/strains were tested:

| ID | Species | Ext. RefNo. | Remarks |
|---|---|---|---|
| MH 6357 | *Mannheimia haemolytica* | M7/2 | Reference strain (cattle infection strain) |
| MH 6374 | *Mannheimia haemolytica* | ATCC 33396 | Reference strain |
| MH 10720 | *Mannheimia haemolytica* | 154 | BRD field isolate |
| MH 12587 | *Mannheimia haemolytica* | 1071 | BRD field isolate, macrolide-resistance: erm+, E+ |
| MH 13093 | *Mannheimia haemolytica* | XB0472-6014.1 | BRD field isolate |
| PM 6267 | *Pasteurella multocida* | P 2225 (L386) | Reference strain (mouse infection strain) |
| PM 6391 | *Pasteurella multocida* | ATCC 43137 | Reference strain |
| PM 10775 | *Pasteurella multocida* | 080130003051 | BRD field isolate |
| PM 12080 | *Pasteurella multocida* | IV102277-0093 | BRD field isolate |

The invention claimed is:

1. A compound of Formula A

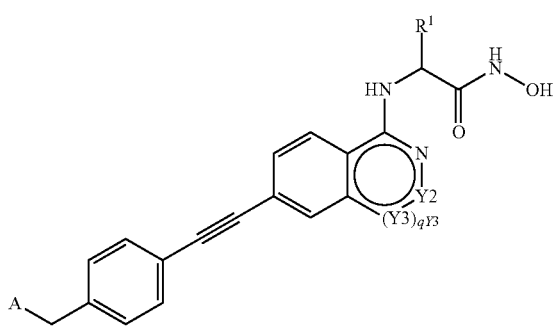

wherein
A is cyclopropylamine,
$R^1$ is $CH(CH_3)OH$,
Y2 is S, and
qY3 is 0.

2. A compound of Formula A

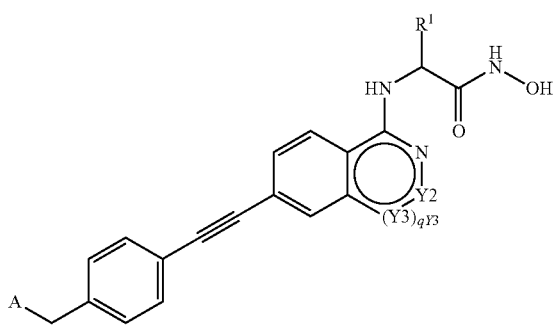

wherein A, R1, Y2 and Y3 are defined as in Table A,

TABLE A

| No | A | R1 | Stereo | Y2 | Y3 |
|---|---|---|---|---|---|
| 1 | morpholine | CH(CH3)OH | S, R | CH | N |
| 2 | cyclopropylamine | CH(CH3)OH | S, R | CH | N |
| 3 | CH3O(CH2)2NH— | CH(CH3)OH | S, R | CH | N |

TABLE A-continued

| No | A | R1 | Stereo | Y2 | Y3 |
|---|---|---|---|---|---|
| 4 | CH2=CHCH2NH— | CH(CH3)OH | S, R | CH | N |
| 5 | benzylamine | CH(CH3)OH | S, R | CH | N |
| 6 | CF3CH2NH- | CH(CH3)OH | S, R | CH | N |
| 7 | cyclopropylamine | CH(CH3)OH | S, R | CH | CH |
| 8 | CH2=CHCH2NH— | CH(CH3)OH | S, R | CH | CH |
| 9 | CH3O(CH2)2NH— | CH(CH3)OH | S, R | CH | CH |
| 10 | cyclopropylamine | CH(CH3)OH | S, R | —S— | qY3 = 0 |
| 11 | CH2=CHCH2NH— | CH(CH3)OH | S, R | —S— | qY3 = 0 |
| 12 | CH3O(CH2)2NH— | CH(CH3)OH | S, R | —S— | qY3 = 0 |
| 13 | morpholine | CH(CH3)OH | S, R | —S— | qY3 = 0 |
| 14 | benzylamine | CH(CH3)OH | S, R | —S— | qY3 = 0 |
| 15 | CF3CH2NH- | CH(CH3)OH | S, R | —S— | qY3 = 0 |
| 16 | cyclopropylamine | C(CH3)2NH2 | racemate | CH | N |
| 17 | CH2=CHCH2NH— | C(CH3)2NH2 | racemate | CH | N |
| 18 | CH3O(CH2)2NH— | C(CH3)2NH2 | racemate | CH | N |
| 19 | morpholine | C(CH3)2NH2 | racemate | CH | N |
| 20 | benzylamine | C(CH3)2NH2 | racemate | CH | N |
| 21 | CF3CH2NH— | C(CH3)2NH2 | racemate | CH | N | and wherein Stereo denotes the absolute configuration wherein the first assignment relates to the atom α to the hydroxamate-carbonyl group; the second assignment relates to the R1 moiety, qY3 is 1 for compounds 1-9 and 16-21.

3. A pharmaceutical composition comprising a compound according to claim 2 and a pharmaceutical acceptable carrier.

4. A method of treating bovine respiratory disease or swine respiratory disease comprising administering an effective amount of a compound according to claim 2 to an animal in need thereof.

5. A method of treating an infection caused by bacteria in an animal wherein the bacteria are at least one of the bacteria selected from the group *Pasteurella multocida, Mannheimia haemolytica* and *Histophilus somni* comprising administering an effective amount of a compound according to claim 2 to an animal in need thereof.

* * * * *